United States Patent
Maruvka et al.

(10) Patent No.: US 11,608,533 B1
(45) Date of Patent: Mar. 21, 2023

(54) COMPOSITIONS AND METHODS FOR CLASSIFYING TUMORS WITH MICROSATELLITE INSTABILITY

(71) Applicant: THE GENERAL HOSPITAL CORPORATION, Boston, MA (US)

(72) Inventors: Yosef E. Maruvka, Boston, MA (US); Gad Getz, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 575 days.

(21) Appl. No.: 16/640,349

(22) PCT Filed: Aug. 21, 2018

(86) PCT No.: PCT/US2018/047398
§ 371 (c)(1),
(2) Date: Feb. 20, 2020

(87) PCT Pub. No.: WO2019/083594
PCT Pub. Date: May 2, 2019

Related U.S. Application Data

(60) Provisional application No. 62/548,138, filed on Aug. 21, 2017.

(51) Int. Cl.
*G16B 20/00* (2019.01)
*C12Q 1/6886* (2018.01)
(Continued)

(52) U.S. Cl.
CPC ........... *C12Q 1/6886* (2013.01); *G16B 20/00* (2019.02); *G16B 40/20* (2019.02); *G16B 50/00* (2019.02);
(Continued)

(58) Field of Classification Search
CPC ........ G16B 40/20; G16B 20/20; G16B 50/20; C12Q 1/6886
See application file for complete search history.

(56) References Cited

U.S. PATENT DOCUMENTS

| 6,482,795 | B1* | 11/2002 | Steck ............... | G01N 33/57434 514/19.2 |
| 2011/0020320 | A1* | 1/2011 | Gudmundsson ..... | C12Q 1/6886 702/19 |

(Continued)

OTHER PUBLICATIONS

International Search Report dated Apr. 1, 2019 for related Application PCT/US2018/047398.
(Continued)

*Primary Examiner* — Eliyah S. Harper
(74) *Attorney, Agent, or Firm* — Withers Bergman LLP; Christopher R. Cowles

(57) ABSTRACT

The present disclosure relates to detecting microsatellite indels in cancer patients and those at high risk for cancer, and is useful for early detection of specific types of cancer and early onset of relapse. More particularly, the present disclosure relates to compositions, methods, and kits for classifying and treating neoplasia and tumors with microsatellite instability. The instant classifier identifies preferred therapeutic options, including combination therapies, for MSI tumor or cancer, and is particularly useful for patient stratification so that patients who would be treatable by immunotherapy drugs may be identified at a very low cost.

14 Claims, 26 Drawing Sheets
Specification includes a Sequence Listing.

(51) Int. Cl.
*G16B 40/20* (2019.01)
*G16B 50/00* (2019.01)

(52) U.S. Cl.
CPC . *C12Q 2600/106* (2013.01); *C12Q 2600/156* (2013.01)

(56) References Cited

U.S. PATENT DOCUMENTS

| | | | | |
|---|---|---|---|---|
| 2015/0337388 | A1* | 11/2015 | Garner, Jr. | G16B 35/00 506/8 |
| 2016/0108380 | A1* | 4/2016 | Iavarone | C07K 16/40 536/23.2 |
| 2017/0107576 | A1* | 4/2017 | Babiarz | C12Q 1/6869 |
| 2017/0233806 | A1* | 8/2017 | Maxwell | G16B 20/20 435/6.11 |
| 2018/0127829 | A1* | 5/2018 | Katz | G01N 33/57488 |

OTHER PUBLICATIONS

The Cancer Genome Atlas Network. Comprehensive Molecular Characterization of Human Colon and Rectal Cancer. Nature. Jul. 18, 2012, 487(7407); pp. 330-337.
Cortes-Ciriano, I, et al. A Molecular Portrait of Microsatellite Instability Across Multiple Cancers. Nature Communications. Jun. 6, 2017, vol. 8:15180.
Chapal-Ilani, N, et al. Comparing Algorithms That Reconstruct Cell Lineage Trees Utilizing Information on Microsatellite Mutations. PLOS Computational Biology. Nov. 14, 2013, vol. 9, No. 11.
Kamburov, A, et al. Comprehensive Assessment of Cancer Missense Mutation Clustering in Protein Structures. PNAS Early Edition. Sep. 21, 2015.
Yoshihara, K, et al. Inferring Tumour Purity and Stromal and Immune Cell Admixture from Expression Data. Nature Communications. Oct. 11, 2013, vol. 4, No. 2612.
International Search Report dated Mar. 5, 2020 for related Application PCT/US2018/047398.

* cited by examiner

COMPOSITIONS AND METHODS FOR CLASSIFYING TUMORS WITH MICROSATELLITE INSTABILITY

CROSS-REFERENCE TO RELATED APPLICATION

This application is a national stage application, filed under 35 U.S.C. § 371, of International Application No. PCT/US18/47398, filed Aug. 21, 2018, which claims the benefit of U.S. Provisional Application No. 62/548,138, filed Aug. 21, 2017, including the four associated mega tables filed as 46783.00.2163 Supplementary Table S1.txt (863 bytes), 46783.00.2163 Supplementary Table S2.txt (725,312 bytes), 46783.00.2163 Supplementary Table S3.txt (9,441 bytes), and 46783.00.2163 Supplementary Table S4.txt (936 bytes), the entire contents of which are incorporated herein by reference.

STATEMENT REGARDING FEDERALLY SPONSORED RESEARCH

This disclosure was made with government support under Grant No. U24CA143845 awarded by the National Institutes of Health. The government has certain rights in the disclosure.

FIELD OF THE DISCLOSURE

The present application relates generally to systems and methods for identifying significantly mutated genes as well as methods for diagnosing and treating cancer.

BACKGROUND OF THE DISCLOSURE

Microsatellites ("MS(s)") or microsatellite DNA are genomic regions containing tandem sequence repeats. Generally, microsatellites are tracts of variable-length repeats (generally repeated 5-50 times) of short DNA motifs (ranging in length from 1-6 or more base pairs). Microsatellites may encompass a variety of low complexity sequences, however, most MSs are mono- or di-nucleotide repeats. Microsatellites occur at thousands of locations within an organism's genome, which are distributed throughout the genome. MSs are abundant in nontranscribed regions of the human genome but may also occur in exons and untranslated regions. In the germline, rates of insertions and deletions (indels) in MSs are significantly higher than rates of single-nucleotide substitutions elsewhere in the genome (e.g., about $10^4$ to $10^3$ compared to about $10^8$ per locus per generation). The increased mutation rate within MS indels is thought to arise because of DNA polymerase slippage during replication, which leads to changes in the number of repeats. MS indels frequently result in frameshift mutations, which can be mutagenic by altering protein expression and/or function.

Tumor microsatellite instability ("MSI") occurs when one or more MS regions have dramatically higher numbers of MS indels, owing to a loss of normal mismatch repair (MMR) function. Tumors with MS regions that do not display dramatically higher numbers of MS indels are generally referred to as microsatellite stable ("MSS"). Although the MSI phenotype has been observed across many tumor types, it appears to be most common in colon adenocarcinoma (COAD), stomach adenocarcinoma (STAD), and uterine corpus endometrial carcinoma (UCEC). The ability to properly classify tumors as either MSI or MSS has very important prognostic and therapeutic implications. Unfortunately, many clinical centers attempt to identify MSI/MSS tumors based on low throughput PCR- or immunohistochemistry-based testing technologies, and the repetitive nature of MSs makes them challenging to analyze via current sequencing methodologies. In view of the foregoing, there is an urgent unmet need for compositions and methods for classifying and treating MSI tumors.

SUMMARY OF THE DISCLOSURE

The present disclosure is based, at least in part, on the discovery that neoplasia or tumors can be classified as either microsatellite stable (MSS) or microsatellite instable (MSI) based on conducting low-pass whole genome sequencing, aggregating sequence information from all microsatellite (MS) loci in the genome, applying different statistical weights to each of the MS loci in the genome, and analyzing the low-pass whole genome sequencing results in combination with the weighting system to conclusively define tumor samples as either MSI or MSS. Because of the vast number of MS loci in the genome (about 23,000,000), the techniques disclosed herein allow accurate identification of MSI versus MSS tumors even with extremely low sequencing coverage rates of approximately 0.01× coverage. Advantageously, the present disclosure provides significantly higher tumor classification accuracy than currently available diagnostic techniques, and may be performed at a much lower cost using only the tumor sample. For example, using current next-generation sequence (NGS) technology (e.g., Illumina HiSeqX), the techniques herein allow accurate tumor classification for only $10-$20 per case.

Discovering cancer-associated microsatellite (MS) loci relies on identifying significant evidence of positive selection. If mutations at a specific MS locus contribute to tumor development, they should be observed in cancer more often than expected by chance. However, simply comparing the frequency of mutations at each MS locus to the average mutation frequency across the genome is inadequate, as the background mutation frequency can vary by nearly two orders of magnitude across the genome, even within a single tissue type (Lawrence, M. S. et al. Mutational heterogeneity in cancer and the search for new cancer-associated genes. Nature 499, 214-218 (2013)). Therefore, accurate estimates of site-specific background mutation frequencies are required in order to maximize the sensitivity to discover cancer-associated MS loci while minimizing the rate of false calls (Lawrence, M. S. et al. Discovery and saturation analysis of cancer genes across 21 tumour types. Nature 505, 495-501 (2014)).

Microsatellites (MSs) are tracts of variable-length repeats of short DNA motifs that are abundant in the human genome and exhibit high rates of mutations in the form of insertions or deletions of the repeated motif (MS indels). Despite their prevalence, the contribution of somatic MS indels to cancer is largely unexplored due to difficulties in detecting them and assessing their significance. The present disclosure provides a comprehensive analysis of MS indels across 20 tumor types using available whole exome sequencing data. The present disclosure characterizes the overall MS indel landscape and detect genes with candidate driver MS indel events. The techniques herein present two novel tools: MSMuTect for accurate detection of somatic MS indels and MSMutSig for identifying genes containing MS indel events at higher frequency than expected by chance.

As described herein, a high variability of the frequency of MS indels across tumors was observed and demonstrates that the number and pattern of MS indels can accurately distinguish microsatellite stable (MSS) tumors from tumors with microsatellite instability (MSI). Applying MSMutSig across 6,747 tumors from 20 different tumor types identified 7 genes with significant MS indel hotspots: ACVR2A, RNF43, DOCK3, MSH3, ESRP1, PRDM2 and JAK1. In the four genes that have been previously implicated in cancer (ACVR24, RNF43, JAK1 and MSH3), previously unreported MS indel events were identified. Three of the genes with significant loci—DOCK3, PRDM2 and ESRP1—had not been previously listed as cancer genes. MS indels in DOCK3, a negative regulator of the WNT pathway, won mutually exclusive with mutations in CTNNB1. MS indels in ESRP1, an RNA processing gene, correlated with alternative splicing of FGFR2, an event associated with the epithelial-to-mesenchymal transition.

The comprehensive analysis of somatic MS indels across cancer disclosed herein highlights their importance, particularly in MSI tumors, significantly contributes to the ongoing global efforts to detect cancer genes and improve classification of patients into clinically-relevant subgroups.

The present disclosure relates to detecting microsatellite indels in cancer patients and those at high risk for cancer and is useful for early detection of specific types of cancer and early onset of relapse. The disclosure is also particularly useful for patient stratification so that patients who would be treatable by immunotherapy drugs could be identified at a very low cost.

The present disclosure relates to a method of identifying and selecting a subject with a cancer or tumor with high microsatellite instability (MSI-H) (as opposed to low microsatellite instability (MSI-L) or a microsatellite stable (MSS) cancer or tumor) which may comprise detecting a limited plurality of not more than 40, 30, 20 or 10 microsatellite indels associated with the MSI-H cancer or tumor (but not a MSI-L cancer or tumor), in a nucleic acid sample from the subject's cancer or tumor, wherein the limited plurality of not more than 40 or 30 or 20 or 10 microsatellite indels that are highly mutated in MSI (MSI-H) cancers, but have a low indel rate in an MSI-L or MSS cancer or tumor, and/or may be identified by a limited plurality set of indels are selected by MSMuTect, and wherein the subject has an MSI-H cancer or tumor if all or at least 39, 35, 30 or 20 of the 40 of the limited plurality of MS indels is present in the nucleic acid sample from the subject's cancer or tumor.

In one embodiment, the cancer or tumor may be colon adenocarcinoma (COAD), stomach adenocarcinoma (STAD), or uterine corpus endometrial carcinoma (UCEC). In another embodiment, the cancer or tumor may be other than colon adenocarcinoma (COAD), stomach adenocarcinoma (STAD), or uterine corpus endometrial carcinoma (UCEC).

In an embodiment wherein the cancer or tumor may be colon adenocarcinoma (COAD), the limited plurality of microsatellite indels detected may comprise at least 5, at least 10 or at least 20 MS indels from a list of COAD MS indels, such as the 20 COAD MS indels in Table A or Table B.

In an embodiment wherein the cancer or tumor is stomach adenocarcinoma (STAD), the limited plurality of microsatellite indels detected may comprise at least 5, at least 10 or at least 20 MS indels from a list of STAD MS indels, such as the list of 20 STAD MS indels in Table A or Table B.

In an embodiment wherein the cancer or tumor is uterine corpus endometrial carcinoma (UCEC), the limited plurality of microsatellite indels detected may comprise at least 5, at least 10 or at least 20 MS indels MS indels from a list of UCEC MS indels, such as the list of 20 UCEC MS indels in Table A or Table B.

In an embodiment wherein the cancer or tumor is other than colon adenocarcinoma (COAD), stomach adenocarcinoma (STAD), or uterine corpus endometrial carcinoma (UCEC), the limited plurality of microsatellite indels detected may comprise at least 5, at least 10 or at least 20 MS indels from a list of MS indels for cancers other than COAD, STAD, or UCEC, such as the list of 20 such MS indels for cancers other than COAD, STAD, or UCEC in Table A or Table B.

The method of the present disclosure also includes identifying one or more somatic indels in a microsatellite (MS) locus (MS indels) in one or more genes that are identified by MSMutSig. The one or more MS indels may be in one or more of the ACVR2A, RNF43, DOCK3, MSH3, ESRP1, PRDM2 and/or JAK1 genes. The one or more MS indels may be in one or more of the ESRP1, PRDM2, or DOCK3 JAK1 genes. The cancer or tumor may be COAD, STAD or UCEC, and the MS indel may be selected from the respective/corresponding MS indels listed in Table C of significantly mutated MS loci for COAD, STAD and UCEC cancers or tumors.

The method of the present disclosure also includes administering an immunotherapy to the subject if they have an MSI-H cancer or tumor.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the disclosure.

The current disclosure also relates, at least in part, to compositions, methods, and kits for classifying and treating neoplasia and tumors with microsatellite instability (MSI). The techniques herein provide compositions and methods for accurately identifying neoplasia and/or tumors as MSI or microsatellite stable (MSS) by obtaining extremely low pass (e.g., ~0.01× coverage) whole genome sequence data from a neoplasia or tumor sample, aggregating sequence information from all MS loci in the genome (e.g., about 23,000,000 MS loci), and analyzing the aggregated sequence data with an analytical model that applies different weights to different MS loci, thereby allowing accurate identification of MSI neoplasia or cells. Advantageously, the techniques herein provide more accurate identification of MSI then prior art methods that use only a small number of loci. Additionally, the present disclosure allows identification of MSI neoplasia or tumors with only a tumor sample. In other words, type matched blood or tissue controls are not required. Furthermore, the techniques herein only require low pass whole genome sequence, which allows MSI identification in a very inexpensive manner that is amenable to high-throughput sample analysis at scale. For example, with the aid of current next generation sequencing (NGS) technology (e.g., Illumina HiSeqX), a single sample may be analyzed for about $10-20.

In one aspect, the disclosure provides a method for selecting a treatment for a subject having or at risk of having a microsatellite instable (MSI) cancer, that includes the following steps: (a) procuring a neoplasia or tumor sample from the subject having or at risk of having MSI cancer, (b)

obtaining whole genome sequence (WGS) data from the neoplasia or tumor sample; (c) identifying a plurality of microsatellite (MS) loci within the WGS data; (d) identifying, for each of the plurality of MS loci, one or more aberrant MS loci containing two or more deleted base pairs relative to one or more reference sequences corresponding to the one or more aberrant MS loci; (e) counting a number of the one or more identified aberrant MS loci to create a sample size count variable; (f) counting a number of times each of the one or more aberrant MS loci contain two or more deleted base pairs that are identical to create a deletion count variable; (g) calculating a score for the neoplasia or tumor sample based on the ratio of the deletion count variable to the sample size count variable; (h) classifying the neoplasia or tumor sample as MSI when the score is greater than a threshold value; and (i) selecting, based on the score being greater than the threshold value, a treatment for the subject comprising a therapeutic agent appropriate for the treatment of a MSI neoplasia or tumor.

In one aspect, the disclosure provides a method for treating a subject having or at risk of having a microsatellite instable (MSI) cancer, that includes the following steps: (a) procuring a neoplasia or tumor sample from the subject having or at risk of having MSI cancer; (b) obtaining whole genome sequence (WGS) data from the neoplasia or tumor sample; (c) identifying a plurality of microsatellite (MS) loci within the WGS data; (d) identifying, for each of the plurality of MS loci, one or more aberrant MS loci containing two or more deleted base pairs relative to one or more reference sequences corresponding to the one or more aberrant MS loci; (e) counting a number of the one or more identified aberrant MS loci to create a sample size count variable; (f) counting a number of times each of the one or more aberrant MS loci contain two or more deleted base pairs that are identical to create a deletion count variable; (g) calculating a score for the neoplasia or tumor sample based on the ratio of the deletion count variable to the sample size count variable; (h) classifying the neoplasia or tumor sample as MSI when the score is greater than a threshold value; and (i) administering, based on the score being greater than the threshold value, a therapeutic agent appropriate for the treatment of a MSI neoplasia or tumor.

In one aspect, the disclosure provides a method for identifying a subject as having a microsatellite instable (MSI) cancer, that includes the steps of: (a) procuring a neoplasia or tumor sample from the subject having or at risk of having MSI cancer, (b) obtaining whole genome sequence (WGS) data from the neoplasia or tumor sample; (c) identifying a plurality of microsatellite (MS) loci within the WGS data; (d) identifying, for each of the plurality of MS loci, one or more aberrant MS loci containing two or more deleted base pairs relative to one or more reference sequences corresponding to the one or more aberrant MS loci; (e) counting a number of the one or more identified aberrant MS loci to create a sample size count variable; (f) counting a number of times each of the one or more aberrant MS loci contain two or more deleted base pairs that are identical to create a deletion count variable; (g) calculating a score for the neoplasia or tumor sample based on the ratio of the deletion count variable to the sample size count variable; (h) classifying the neoplasia or tumor sample as MSI when the score is greater than a threshold value; and (i) identifying, based on the score being greater than the threshold value, the subject as having a MSI neoplasia or tumor.

In one aspect, the disclosure provides a method for treating a subject having or at risk of having a microsatellite instable (MSI) cancer, that includes the steps of: (a) obtaining a neoplasia or tumor sample from the subject having or at risk of having MSI cancer, (b) obtaining whole genome sequence (WGS) data from the neoplasia or tumor sample; (c) detecting one or more sequence reads within the WGS data spanning a plurality of microsatellite (MS) loci of a predetermined length; (d) identifying one or more aberrant sequence reads within the one or more sequence reads spanning the plurality of MS loci that contain deleted base pairs or inserted base pairs relative to a plurality of reference sequences corresponding to the one or more aberrant sequence reads; (e) aggregating the identified one or more aberrant sequence reads for each the MS loci into groups that contain the same number of deleted base pairs or inserted base pairs for each of the plurality of MS loci; (f) calculating a score for the neoplasia or tumor sample based on the ratio of deleted base pairs to inserted base pairs; (g) classifying the neoplasia or tumor sample as MSI when the score is greater than a threshold value; and (h) administering, based on the score being greater than the threshold value, a therapeutic agent appropriate for the treatment of a MSI neoplasia or tumor.

In one aspect, the disclosure provides a method for identifying a subject as having a microsatellite instable (MSI) cancer, that includes the steps of: (a) obtaining a neoplasia or tumor sample from the subject having or at risk of having MSI cancer; (b) obtaining whole genome sequence (WGS) data from the neoplasia or tumor sample; (c) detecting one or more sequence reads within the WGS data spanning a plurality of microsatellite (MS) loci of a predetermined length; (d) identifying one or more aberrant sequence reads within the one or more sequence reads spanning the plurality of MS loci that contain deleted base pairs or inserted base pairs relative to a plurality of reference sequences corresponding to the one or more aberrant sequence reads; (e) aggregating the identified one or more aberrant sequence reads for each the MS loci into groups that contain the same number of deleted base pairs or inserted base pairs for each of the plurality of MS loci; (f) calculating a score for the neoplasia or tumor sample based on the ratio of deleted base pairs to inserted base pairs; (g) classifying the neoplasia or tumor sample as MSI when the score is greater than a threshold value; and (h) identifying, based on the score being greater than the threshold value, the subject as having a MSI neoplasia or tumor.

In exemplary embodiments, the obtaining step (a) further comprises preparing genomic DNA from the neoplasia or tumor sample.

In exemplary embodiments, the obtaining step (b) comprises sequencing 1 ng-1 mg of prepared genomic DNA.

In exemplary embodiments, the obtaining step (b) comprises sequencing at least 10 ng-1 mg of prepared genomic DNA.

In exemplary embodiments, the WGS data is residual sequence data. In exemplary embodiments, the residual sequence data is whole exome sequencing data or whole panel sequencing data.

In exemplary embodiments, the predetermined length is about 5 to about 20 base pairs or about 5 to about 15 base pairs or about 8 to about 13 base pairs.

In exemplary embodiments, the two or more deleted base pairs am selected from the group consisting of A, C, AC, AG, and GCT.

In exemplary embodiments, the one or more reference sequences are obtained from non-neoplasia or non-tumor samples from the subject.

In exemplary embodiments, calculating step (g) or (f) is based on the following algorithm:

$$S = \log_{10}\left(\left|\frac{\alpha_i \cdot N_i^{del\_j}}{N_i^{ref}}\right|\right),$$

wherein S is the score, i is the MS length, del_j is the size of the deletion, and N_i the number of MS loci of the predetermined length.

In exemplary embodiments, obtaining step (b) comprises use of a technology selected from the group consisting of targeted hybrid capture, an amplicon-based sequencing technology, a non-targeted sequencing technology, and a next-generation sequencing (NGS) technology.

In exemplary embodiments, the classifying step does not require comparing the neoplasia or tumor sample from the subject to a type matched normal sample.

In exemplary embodiments, the above methods may further comprising administering one or more selected treatments to the subject having or at risk of having MSI.

In one aspect, the present disclosure provides a kit for identifying a neoplasia or tumor sample as MSI or MSS, wherein the kit comprises reagents for effecting steps (a)-(c) of claims 1-5.

In one aspect, the present disclosure provides a method, including the steps of: identifying, at a processor of a computing device configured to analyze high throughput sequencing data, a plurality of microsatellite (MS) loci within a whole genome sequence (WGS) dataset from a neoplasia or a tumor, identifying, at the processor, one or more aberrant MS loci within the plurality of MS loci that contain two or more deleted base pairs relative to one or more reference sequences corresponding to the one or more aberrant MS loci; incrementing a sample size count variable for each of the identified one or more aberrant MS loci; identifying, at the processor, one or more instances where the one or more aberrant MS loci contain two or more deleted base pairs that are identical; incrementing a deletion count variable for each of the identified one or more instances; calculating, at the processor, a score for the neoplasia or tumor sample based on the ratio of the deletion count variable to the sample size count variable; and classifying the neoplasia or tumor sample as MSI when the score is greater than a threshold value.

In embodiments, calculating step (g) or (f) is based on the following algorithm:

$$S = \log_{10}\left(\left|\frac{\alpha_i \cdot N_i^{del\_j}}{N_i^{ref}}\right|\right),$$

wherein S is the score, i is the MS length, del_j is the size of the deletion, and N_i the number of MS loci of the predetermined length.

In embodiments, $\alpha\_i=1$ for $8 \leq i \leq 13$ and $\alpha\_i=0$ otherwise.

In one aspect, the disclosure provides an apparatus, including: one or more network interfaces to communicate in a computer network; a processor coupled to the network interfaces and adapted to execute one or more processes; and a memory configured to store a process executable by the processor, the process when executed operable to: identify a plurality of microsatellite (MS) loci within a whole genome sequence (WGS) dataset from a neoplasia or a tumor, identify one or more aberrant MS loci within the plurality of MS loci that contain two or more deleted base pairs relative to one or more reference sequences corresponding to the one or more aberrant MS loci; increment a sample size count variable for each of the identified one or more aberrant MS loci; identify one or more instances where the one or more aberrant MS loci contain two or more deleted base pairs that are identical; increment a deletion count variable for each of the identified one or more instances; calculate a score for the neoplasia or tumor sample based on the ratio of the deletion count variable to the sample size count variable; and classify the neoplasia or tumor sample as MSI when the score is greater than a threshold value.

In embodiments, the calculating step is based on the following algorithm:

$$S = \log_{10}\left(\left|\frac{\alpha_i \cdot N_i^{del\_j}}{N_i^{ref}}\right|\right),$$

wherein S is the score, i is the MS length, del_j is the size of the deletion, and N_i the number of MS loci of the predetermined length.

In embodiments, $\alpha\_i=1$ for $8 \leq i \leq 13$ and $\alpha\_i=0$ otherwise.

In embodiments, the WGS data or WGS dataset is obtained at about 60× to about 0.001× coverage. In embodiments, the WGS data or WGS dataset is obtained at about 5× to about 0.01× coverage. In embodiments, the WGS data or WGS dataset is obtained at about 1× to about 0.01× coverage. In embodiments, the WGS data or WGS dataset is obtained at about 0.001× coverage. In embodiments, the WGS data or WGS dataset is obtained at about 0.01×, 0.015×, 0.02×, 0.025×, 0.03×, 0.035×, 0.04×, 0.045×, 0.05×, 0.055×, 0.06×, 0.065×, 0.07×, 0.075×, 0.08×, 0.085×, 0.09×, or 0.1× coverage. In embodiments, the WGS data or WGS dataset is obtained at about 0.1×, 0.2×, 0.3×, 0.4×, 0.5×, 0.6×, 0.7×, 0.8×, 0.9×, or 1.0× coverage.

In one aspect, the disclosure provides a method of identifying and selecting a subject with a cancer or tumor with high microsatellite instability (MSI-H) comprising detecting a limited plurality of not more than 40, 30, 20 or 10 microsatellite indels associated with the MSI-H cancer or tumor, but not a low microsatellite instability (MSI-L) cancer or tumor, in a nucleic acid sample from the subject's cancer or tumor, wherein the limited plurality of not more than 40, 30, 20 or 10 microsatellite indels that are highly mutated in MSI-H cancers, but have a low indel rate in an MSI-L or microsatellite stable (MSS) cancer or tumor, are identified by or are selected by MSMuTect, and wherein the subject has an MSI-H cancer or tumor if at least 39, 35, 30 or 20 of the limited plurality of MS indels is present in the nucleic acid sample from the subject's cancer or tumor.

In embodiments, the indel is a deletion. In embodiments, the indel is an insertion.

In embodiments, the cancer or tumor is colon adenocarcinoma (COAD), stomach adenocarcinoma (STAD), or uterine corpus endometrial carcinoma (UCEC).

In embodiments, the cancer or tumor is other than colon adenocarcinoma (COAD), stomach adenocarcinoma (STAD), or uterine corpus endometrial carcinoma (UCEC).

In embodiments, the cancer or tumor is colon adenocarcinoma (COAD) and the limited plurality of microsatellite indels detected comprises at least 5, at least 10 or at least 20 MS indels from the list of 20 COAD MS indels in Table A or Table B.

In embodiments, the cancer or tumor is stomach adenocarcinoma (STAD) and the limited plurality of microsatellite indels detected comprises at least 5, at least 10 or at least 20 MS indels from the list of 20 STAD MS indels in Table A or Table B.

In embodiments, the cancer or tumor is uterine corpus endometrial carcinoma (UCEC) and the limited plurality of microsatellite indels detected comprises at least 5, at least 10 or at least 20 MS indels from the list of 20 UCEC MS indels in Table A or Table B.

In embodiments, the limited plurality of microsatellite indels detected comprises at least 5, at least 10 or at least 20 MS indels from the list of 20 such MS indels for cancers other than COAD, STAD, or UCEC in Table A or Table B.

In embodiments, the method includes identifying one or more somatic indels in a microsatellite (MS) locus (MS indels) in one or more genes that are identified by or are selected by MSMutSig.

In embodiments, the one or more MS indels are in one or more of the ACVR2A, RNF43, DOCK3, MSH3, ESRP1, PRDM2 and/or JAK1 genes.

In embodiments, the one or more MS indels are in one or more of the ESRP1, PRDM2, or DOCK3 JAK1 genes.

In embodiments, the cancer or tumor is COAD, STAD or UCEC, and the MS indel is selected from the MS indels listed in Table C, Table A or Table B of significantly mutated MS loci for COAD, STAD and UCEC cancers or tumors.

In embodiments, the above methods may further comprise administering an immunotherapy to the subject having an MSI-H cancer or tumor.

In embodiments, the immunotherapy is administrating of a programmed cell death protein 1 (PD-1) inhibitor. In embodiments, the PD-1 inhibitor is an antibody. In embodiments, the antibody is pembrolizumab.

In an aspect, the disclosure provides a method, that includes the following steps: identifying, at a processor of a computing device configured to analyze high throughput sequencing data, a plurality of microsatellite (MS) loci within a whole genome sequence (WGS) dataset from a neoplasia or a tumor, identifying, at the processor, one or more aberrant sequence reads within the plurality of MS loci that contain deleted base pairs or inserted base pairs relative to a plurality of reference sequences corresponding to the one or more aberrant sequence reads; aggregating the identified one or more aberrant sequence reads for each the MS loci into groups that contain the same number of deleted base pairs or inserted base pairs for each of the plurality of MS loci; calculating a score for the neoplasia or tumor sample based on the ratio of deleted base pairs to inserted base pairs; and classifying the neoplasia or tumor sample as MSI when the score is greater than a threshold value.

In an aspect, the disclosure provides an apparatus, including: one or more network interfaces to communicate in a computer network; a processor coupled to the network interfaces and adapted to execute one or more processes; and a memory configured to store a process executable by the processor, the process when executed operable to: identify a plurality of microsatellite (MS) loci within a whole genome sequence (WGS) dataset from a neoplasia or a tumor, identify one or more aberrant sequence reads within the plurality of MS loci that contain deleted base pairs or inserted base pairs relative to a plurality of reference sequences corresponding to the one or more aberrant sequence reads; aggregate the identified one or more aberrant sequence reads for each the MS loci into groups that contain the same number of deleted base pairs or inserted base pairs for each of the plurality of MS loci; calculate a score for the neoplasia or tumor sample based on the ratio of deleted base pairs to inserted base pairs; and classify the neoplasia or tumor sample as MSI when the score is greater than a threshold value.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5% 40%, 3%, 2%, 10%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally, or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

As used herein, the term "algorithm" refers to any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, statistical weights, and neural networks trained on populations or datasets. Also, of use in the context of MSI as described herein are linear and non-linear equations and statistical classification analyses to determine the relationship between the presence of indels detected at specific MS loci in the genome of a subject's tumor sample.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, colon adenocarcinoma (COAD), esophageal carcinoma (ESCA), rectal adenocarcinoma (READ), stomach adenocarcinoma (STAD) and uterine corpus endometrial carcinoma (UCEC). It is also contemplated within the scope of the disclosure that the techniques herein may be applied to detect MSI in liquid tumors such as, for example, leukemia and lymphoma.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

By "homopolymers(s)" is meant a microsatellite (MS) that is a mononucleotide repeat of at least 6 bases (e.g., a stretch of at least 6 consecutive A, C, T or G residues in the DNA). A "homopolymer region" is a MS region in which the microsatellite is a homopolymer. A "homopolymer subregion" refers to a homopolymer microsatellite located within a larger genomic region (e.g., a homopolymer region).

As used herein, the term "indel" refers to a mutation in a nucleic acid in which one or more nucleotides are either inserted or deleted, resulting in a net gain or loss of nucleotides that can include any combination of insertions and deletions. Aberrant homopolymer lengths often result from indels.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, "microsatellite (MS)" refers to a genetic locus comprising a short (e.g., 1-20, 1-15, 1-10, 1-9, 1-8, 1-7, 1-6, 1-5, 1-4, 1-3, 1-2, etc.), tandemly repeated sequence motifs comprising a minimal total length of about 6 bases. A "mononucleotide microsatellite" or refers to a genetic locus comprising a repeated single nucleotide (e.g., poly-A) and is a specific subclass of MSs. A "dinucleotide microsatellite" refers to a genetic locus comprising a motif of two nucleotides that are tandemly repeated, a "trinucleotide microsatellite" refers to a genetic locus comprising three nucleotides that are tandemly repeated, and a "tetranucleotide microsatellite" refers to a genetic locus comprising a motif of four nucleotides that are tandemly repeated. Additional microsatellite motifs can comprise pentanucleotide and hexanucleotide repeats. A "monomorphic microsatellite" is one in which all (or substantially all) individuals, particularly all individuals of a given population, share the same number of repeat units, which is in contrast to a "polymorphic microsatellite," which is used to refer to microsatellites in which more than about 1% of individuals in a given population display a different number of repeat units in at least of their alleles. When analyzing MS, one may look at genomic DNA of a sample (e.g., genomic DNA of a tumor cell). "Microsatellite region" refers to the genomic context in which a particular microsatellite resides (i.e., the particular genomic region containing the MS).

As used herein, "microsatellite instability (MSI)" refers to a clonal or somatic change in the number of repeated DNA nucleotide units in MSs such as, for example, insertions and deletions (indels). The term "microsatellite stable (MSS)" refers to MSs that do not display a clonal or somatic change in the number of repeated DNA nucleotide units in the respective MSs. In some embodiments detecting MSI in a tumor or cancer cell sample may include classifying MSI or MSS status in the tumor or cancer cell, in which case the method may include a classification step as described herein.

By "neoplasia" is meant a disease or disorder characterized by excess proliferation or reduced apoptosis. Illustrative neoplasms for which the disclosure can be used include, but are not limited to, breast cancer, esophageal cancer, pancreatic cancer, colorectal cancer, hepatocellular cancer, bladder cancer, luminal and non-luminal bladder cancer, basal bladder cancer, muscle-invasive bladder cancer, and non-muscle-invasive bladder cancer, pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In embodiments, the neoplasia may be colon adenocarcinoma (COAD), stomach adenocarcinoma (STAD), and uterine corpus endometrial carcinoma (UCEC). In embodiments, the neoplasia may be a liquid tumor such as, for example, leukemia or lymphoma.

As used herein, the term "next-generation sequencing (NGS)" refers to a variety of high-throughput sequencing technologies that parallelize the sequencing process, producing thousands or millions of sequence reads at once. NGS parallelization of sequencing reactions can generate hundreds of megabases to gigabases of nucleotide sequence reads in a single instrument run. Unlike conventional sequencing techniques, such as Sanger sequencing, which typically report the average genotype of an aggregate collection of molecules, NGS technologies typically digitally tabulate the sequence of numerous individual DNA fragments (sequence reads discussed in detail below), such that low frequency variants (e.g., variants present at less than about 10%, 5% or 1% frequency in a heterogeneous population of nucleic acid molecules) can be detected. The term "massively parallel" can also be used to refer to the simultaneous generation of sequence information from many different template molecules by NGS. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, et al., "Next-generation DNA sequencing," Nature, 2008, vol. 26, No. 10, 135-1 145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11

(3):333-43; and Zhang et al., "The impact of next-generation sequencing on genomics," J Genet Genomics, 201, 38(3): 95-109.

As used herein, the term "subject" includes humans and mammals (e.g., mice, rats, pigs, cats, dogs, horses, and the like). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, e.g., arresting its development; and (c) relieving the disease, e.g., causing regression of the disease.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar, buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methlyamine, dimethylamine, trimethlyamine, triethlyamine, ethylamine, and the like. (See, for example, S. M. Barge et al., "Pharmaceutical Salts," J. Pharm. Sci., 1977, 66:1-19 which is incorporated herein by reference.).

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In addition, the materials, methods, and examples are illustrative only and not intended to be limiting.

These and other embodiments are disclosed or are obvious from and encompassed by, the following Detailed Description.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A shows that all reads containing an MS region and sufficient 3' and 5' flanking sequence are aligned to a collection of all MS loci and the number of reads supporting each MS length are tallied to create a histogram of observed read lengths per locus. FIG. 1B shows that the length histograms for all sites that share the same underlying motif and number of repeats (i.e., sites with the same motif and mode length) from the X chromosome of male normal samples were combined into a single histogram. This combined histogram represents the empirical noise distribution (i.e., the probability that a true allele with i repeats will generate a read with j repeats). FIG. 1C shows that the maximum likelihood method and empirical noise distribution are used to identify the set of alleles that best describes the histogram for a given locus. This set includes the number of alleles, the length of each allele, and the fraction of DNA molecules representing each allele in the sample. After determining the most likely allele for both the tumor and normal sample, somatic MS indels are nominated when the tumor model fits the tumor data better than the normal model fits the tumor data and vice versa.

FIG. 3A shows the distribution of A (e.g., adenine) motif MS indels across clinical microsatellite (MS) subgroups (MS stable [MSS]; high MS instability [MSI-H]; and low MS instability [MSI-L]) in the three TCGA tumor types for which clinical MSI status was reported (colon adenocarcinoma [COAD], stomach adenocarcinoma [STAD], and uterine corpus endometrial carcinoma [UCEC]). Tumors with ≥15% of SNVs attributed to MS mutations (MSI-SNVs) are plotted in red and tumors with <15% MSI-SNVs are shown in blue. Similarly, tumors with ≥15% SNVs attributed to POLE-mediated mutagenesis (POLE-SNVs) are denoted with an 'x'. FIG. 3B shows mean relative MS indel frequencies across quintiles of replication times calculated for MSI-H and MSS tumors (combined from the COAD, STAD and UCEC cohorts). While no significant correlation was observed between MS indel frequency and replication timing in MSS tumors (slope=−0.03, Pearson correlation=−0.47, P=0.43, t-test), there was a negative correlation in MSI tumors (slope=−0.1 Pearson correlation=−0.995, P<3×10$^{-4}$, t-test). FIG. 3C shows MS indel frequency as a function of MS length are shown for MSS and MSI-H tumors. In both MSS and MSI-H tumors, the mutation frequency increases with increasing MS length; however, the increase is more rapid in MSI-H tumors, which is reflected in the ratio of mutation frequency of MSI-H to MSS tumors across MS loci lengths (inset). FIG. 3D shows frequencies of MS insertions and deletions as a function of normal and mutated repeat number. The y-axis shows the estimated number of MS repeats in the normal sample and the x-axis shows the change in the number of repeats in the tumor. The frequency of each specific event (i.e., an insertion or deletion of a given length) was calculated as a fraction of the total number of covered loci across all samples. MSI-H samples are shown in the upper panel, MSS samples in the lower panel, and the middle panel summarizes data across all alleles. The MSI-H samples are significantly more likely to harbor deletions while the MSS are more likely to have insertions (p-value<10$^{-31}$, $\chi^2$ test). Only MS loci that had at least 5 repeats in both the normal and mutated samples were included.

FIG. 11 shows a series of charts showing the distribution of MS indels across cancer. Comparison of the fraction of MS indels (upper panel) and number of SNVs (lower panel) across 4,041 tumors from 20 tumor types. Only samples with annotated MS indels and SNVs are shown. Red horizontal lines represent the median number of MS indels in each tumor type.

DETAILED DESCRIPTION OF THE DISCLOSURE

Figure 1:
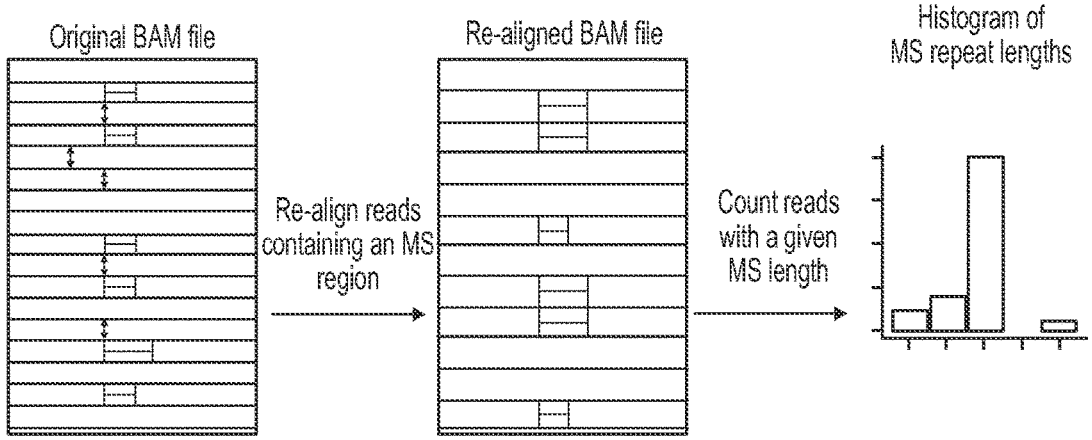
FIGS. 1A-1C show three panels that depict a schematic description of MSMuTect, which identifies somatic indels in microsatellites (MS indels).
Figure 1:
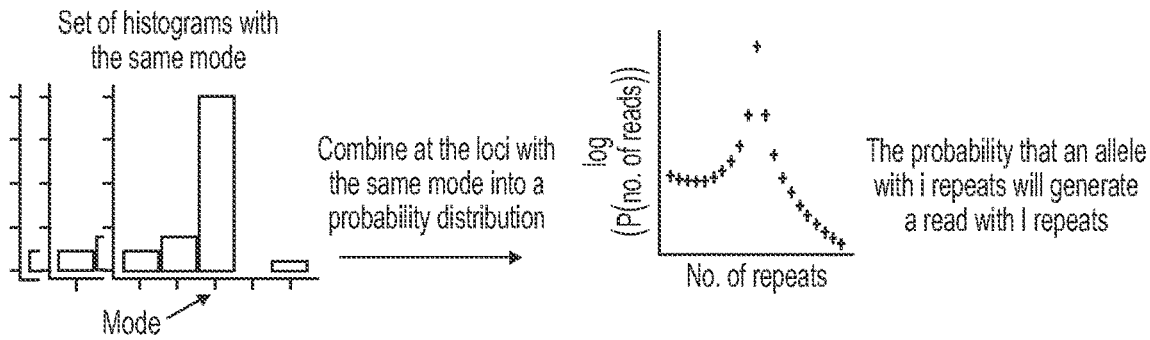
Figure 1:
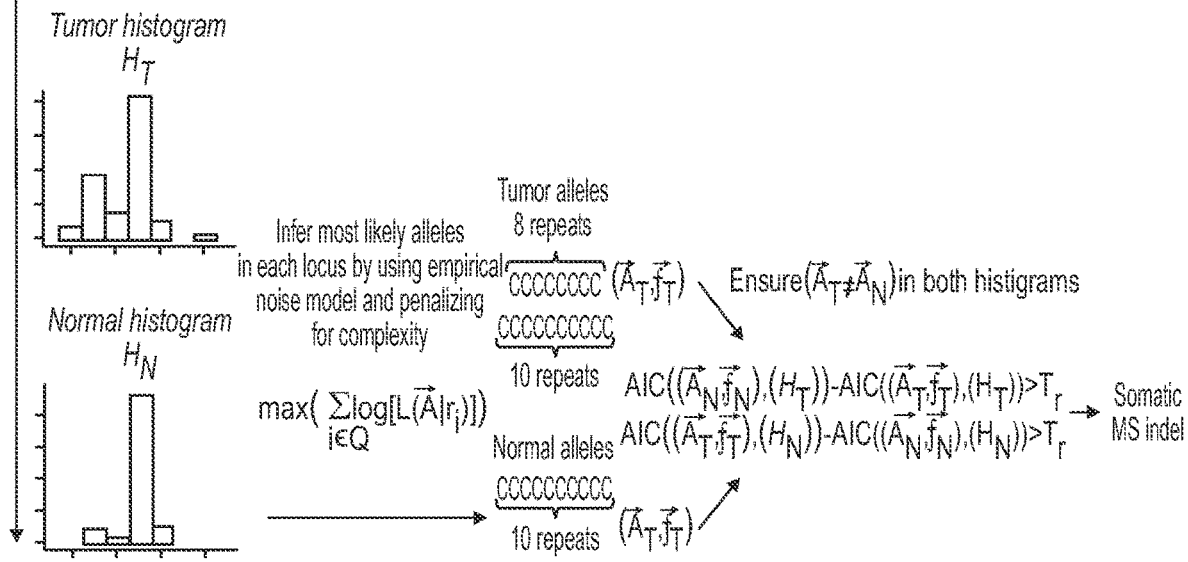

The present disclosure is based, at least in part, on the discovery that neoplasia or tumors can be classified as either microsatellite stable (MSS) or microsatellite instable (MSI) based on conducting low-pass whole genome sequencing, aggregating sequence information from all microsatellite (MS) loci in the genome, applying different statistical weights to each of the MS loci in the genome, and analyzing the low-pass whole genome sequencing results in combination with the weighting system to conclusively define tumor samples as either MSI or MSS. Because of the vast number of MS loci in the genome (about 23,000,000), the techniques disclosed herein allow accurate identification of MSI versus MSS tumors even with extremely low sequencing coverage rates of approximately 0.01× coverage. Advantageously, the present disclosure provides significantly higher tumor classification accuracy than currently available diagnostic techniques and may be performed at a much lower cost using only the tumor sample. For example, using current next-generation sequence (NGS) technology (e.g., Illumina HiSeqX), the techniques herein allow accurate tumor classification for only $10-$20 per case.

Tumors that have a mismatch repair deficiency are called MSI tumors due to an increased rate of insertions and deletions (e.g., indels) in microsatellite loci of the genome. Classifying tumors, as MSI is important because MSI tumors are entitled to PD1/PDL1 immunotherapy. The techniques herein provide a new tool for classifying tumors based on low pass whole genome that is very accurate even at an extremely low sequence coverage rate of ~0.01× coverage. The techniques herein provide a weighting algorithm that is applied to aggregated whole genome sequencing (WGS) sequence data from all MS loci in the genome together with different weights being applied to different loci. Advantageously, the techniques herein make it possible to confidently call a neoplasia or tumor sample as MSI without requiring every MS locus to be identified as either MSI or MSS. The vast number of MS loci in the genome (e.g., about 23,000,000) makes it possible to conclusively define samples as MSI or MSS in a more accurate way then current methods that use only a small number of loci.

Recently it has been shown that MSI tumors respond to immunotherapy, and the FDA approved pembrolizumab (PD-1/PD-L1 inhibitor) to all solid tumors. Therefore, there is an urgent need to classify tumors as MSI, because patients with MSI tumors can benefit from immunotherapy. Unfortunately, current tests four MSI result in high false positive rates (IHC) and are both time consuming and expensive.

The following detailed description is of example embodiments of the presently claimed disclosure with references to the accompanying drawings. Such description is intended to be illustrative and not limiting with respect to the scope of the present disclosure. Such embodiments are described in sufficient detail to enable one of ordinary skill in the art to practice the subject disclosure, and it will be understood that other embodiments may be practiced with some variations without departing from the spirit or scope of the subject disclosure.

The present disclosure relates to detecting microsatellite indels in cancer patients and those at high risk for cancer and is useful for early detection of specific types of cancer and early onset of relapse. The disclosure is also particularly useful for patient stratification so that patients who would be treatable by immunotherapy drugs could be identified at a very low cost.

Overview

Microsatellites (MSs), also known as short tandem repeats, are regions of the genome characterized by repetition of a short sequence motif (usually 1-6 bp), e.g. AAAAAA or ACACACACAC (Ellegren, H. Microsatellites: simple sequences with complex evolution. Nat. Rev. Genet. 5, 435-445 (2004)). MSs are abundant in non-transcribed regions of the human genome, but also occur in exons and untranslated regions (UTRs) with a similar frequency. In the germline, rates of insertions and deletions (indels) in MSs are significantly higher than rates of single nucleotide substitutions elsewhere in the genome ($10^{-4}$-$10^{-3}$ compared to ~$10^{-8}$ per locus per generation, respectively) (Sun, J. X. et al. A direct characterization of human mutation based on microsatellites. Nat. Genet. 44, 1161-1165 (2012)). The increased indel mutation rate within MSs is thought to arise due to DNA polymerase slippage during replication of repetitive sequences, leading to changes in the number of repeats (Ellegren, H. Microsatellites: simple sequences with complex evolution. Nat. Rev. Genet. 5, 435-445 (2004)). MS indels frequently result in frameshift mutations and can therefore dramatically alter protein function by changing the amino acid sequence and/or introducing premature stop codons (Ellegren, H. Microsatellites: simple sequences with complex evolution. Nat. Rev. Genet. 5, 435-445 (2004)).

Given their prevalence and relatively high mutation rate, it is perhaps not surprising that microsatellites have been widely implicated in human disease. More than 40 hereditary diseases are caused by germline MS indels (Pearson, C. E., Edamura, K. N. & Cleary, J. D. Repeat instability: mechanisms of dynamic mutations. Nat. Rev. Genet. 6, 729-742 (2005)), including Huntington's disease (Kennedy, L. et al. Dramatic tissue-specific mutation length increases are an early molecular event in Huntington disease pathogenesis. Hum. Mol. Genet. 12, 3359-3367 (2003)) and fragile X syndrome (Willemsen, R., Levenga, J. & Oostra, B. A. CGG repeat in the FMR1 gene: size matters. Clin. Genet. 80, 214-225 (2011)). In addition, many cancer genes (Nik-Zainal, S. et al. Landscape of somatic mutations in 560 breast cancer whole-genome sequences. Nature 534, 47-54 (2016))(e.g. TP53, PTEN and NF1) contain MS loci, and in some cases, somatic MS indels have been causally implicated in cancer (Giannakis, M. et al. RNF43 is frequently mutated in colorectal and endometrial cancers. Nat. Genet. 46, 1264-1266 (2014)). Tumors with microsatellite instability (MSI) have dramatically increased numbers of MS indels owing to loss of normal mismatch repair (MMR) function (Vilar, E. & Gruber, S. B. Microsatellite instability in colorectal cancer—the stable evidence. Nat. Rev. Clin. Oncol. 7, 153-162(2010)). Although the MSI phenotype has been observed across tumor types, it appears to be most common in colon adenocarcinoma (COAD), stomach adenocarcinoma (STAD), and uterine corpus endometrial carcinoma (UCEC) (Vilar, E. & Gruber, S. B. Microsatellite instability in colorectal cancer—the stable evidence. Nat. Rev. Clin. Oncol. 7, 153-162 (2010)). Given the important prognostic and therapeutic implications of MSI status, many clinical centers perform routine PCR- or immunohistochemistry-based MSI testing for these tumor types (Stadler, Z. K. Diagnosis and management of DNA mismatch repair-deficient colorectal cancer. Hematol. Oncol. Clin. North Am. 29, 29-41 (2015), Le, D. T. et al. PD-1 Blockade in Tumors with Mismatch-Repair Deficiency. N. Engl. J. Med. 372, 2509-

2520 (2015), Watkins, J. C. et al. Universal Screening for Mismatch-Repair Deficiency in Endometrial Cancers to Identify Patients With Lynch Syndrome and Lynch-like Syndrome. Int. J. Gynecol. Pathol. Off. J. Int. Soc. Gynecol. Pathol. (2016). doi:10.1097/PGP.0000000000000312, Umar, A. et al. Revised Bethesda Guidelines for Hereditary Nonpolyposis Colorectal Cancer (Lynch Syndrome) and Microsatellite Instability. J. Natl. Cancer Inst. 96, 261-268 (2004)).

Despite their potential biological significance, somatic MS indels have not been systematically analyzed in cancer due to challenges associated with their detection via current next-generation sequencing (NGS) technologies (Hause, R. J., Pritchard, C. C., Shendure, J. & Salipante, S. J. Classification and characterization of microsatellite instability across 18 cancer types. Nat. Med. 22, 1342-1350 (2016)). Only NGS reads that span the entire length of a MS and include sufficient 5' and 3' flanking sequences can be used to infer the number of repeated motifs in the MS. In addition, the PCR amplification step that is performed during NGS can itself suffer from DNA polymerase slippage events similar to those that lead to MS indels in vivo, thereby creating NGS artifacts that may be falsely interpreted as MS indels. The frequency of such sequencing errors varies across MS loci and depends on parameters such as the specific MS motif and the number of repeats. Therefore, novel methods utilizing principled statistical modeling and noise estimation are required to accurately identify true MS indel events.

Citation or identification of any document in this application is not an admission that such document is available as prior art to the present disclosure.

Applying MSMutSig across 6,747 tumors from 20 different tumor types identified 7 genes with significant MS indel hotspots: ACVR2A, RNF43, DOCK3, MSH3, ESRP1, PRDM2 and/or JAK1. In the four genes that have been previously implicated in cancer (ACVR2A, RNF43, JAK1 and MSH3), previously unreported MS indels events were identified. Three of the genes with significant loci— DOCK3, PRDM2 and ESRP1—had not been previously listed as cancer genes. MS indels in DOCK3, a negative regulator of the WNT pathway, were mutually exclusive with mutations in CTNNB1. MS indels in ESRP1, an RNA processing gene, correlated with alternative splicing of FGFR2, an event associated with the epithelial-to-mesenchymal transition.

The present disclosure relates to detecting microsatellite indels in a cancer patient and/or an individual at risk for cancer. In one embodiment, the disclosure relates to detecting one or more indels in one or more genes with significant microsatellite stable indel hotspots. In an advantageous embodiment, the one or more genes with significant microsatellite stable indel hotspots include, but are not limited to, ACVR2A, RNF43, DOCK3, MSH3, ESRP1, PRDM2 and/or JAK1 genes.

The present disclosure relates to achieving classification by using whole genome or whole exome data. The classification relies both on the fact that high MS instability (MSI-H) contains a large fraction of the MSI loci mutated, as well as the fact that the type of MS indels in MSI-H cases differ from those in microsatellite stable (MSS) cases. For example, MSI tumors tend to have more one-base deletion in medium size loci (8-15 bases), while non-MSI cases, even if they contain many MS indels, have a more uniform ratio of deletions and insertions, and they do not have this bias to medium sized loci.

The present disclosure relates to a method of identifying and selecting a subject with a cancer or tumor with high microsatellite instability (MSI-H) (as opposed to low microsatellite instability (MSI-L) or a microsatellite stable (MSS) cancer or tumor) which may comprise detecting a limited plurality of not more than 40, 30, 20 or 10 microsatellite indels associated with the MSI-H cancer or tumor (but not a MSI-L cancer or tumor), in a nucleic acid sample from the subject's cancer or tumor, wherein the limited plurality of not more than 40 or 30 or 20 or 10 microsatellite indels that are highly mutated in MSI (MSI-H) cancers, but have a low indel rate in an MSI-L or MSS cancer or tumor, and/or may be identified by a limited plurality set of indels are selected by MSMuTect, and wherein the subject has an MSI-H cancer or tumor if all or at least 39, 35, 30 or 20 of the 40 of the limited plurality of MS indels is present in the nucleic acid sample from the subject's cancer or tumor.

For the analysis of microsatellite stable (MSS) versus unstable (MSI) tumors, only samples from the colon (COAD), stomach (STAD), and uterine (UCEC) cohorts that had MSI status annotated by the TCGA were used (see the World Wide Web at (www)tcga-data.nci.nih.gov/docs/publications/tega/). MSI classifier loci of COAD, STAD and UCEC is presented in Table A below:

TABLE A

| COAD | STAD | UCEC |
|---|---|---|
| chr6:33269395:33269406:A:12.000 | chr1:14108749:14108757:A:9.000 | chr13:101844277:101844281:A:5.000 |
| chr20:58587784:58587793:A:10.000 | chr3:30691872:30691881:A:10.000 | chr15:89744159:89744163:A:5.000 |
| chr2:148683686:148683693:A:8.000 | chr5:161494991:161495002:A:12.000 | chr17:73205918:73205922:A:5.000 |
| chr2:68269961:68269979:C:19.000 | chr3:113377482:113377492:A:11.000 | chr1:6246559:6246567:A:9:000 |
| chr17:56435161:56435167:C:7.000 | chr3:126220106:126220113:A:8.000 | chr5:78936937:78936943:A:7.000 |
| chr5:72199545:72199551:A:7.000 | chr2:148683686:148683693:A:8.000 | chr6:56323634:56323641:A:8.000 |
| chr2:96994051:96994060:A:10.000 | chrX:15364159:15364168:A:10.000 | chr9:75355041:75355047:A:7.000 |
| chr5:122359468:122359479:A:12.000 | chr4:76539580:76539588:A:9.000 | chr11:111904183:111904190:A:8.000 |
| chr3:100039736:100039744:A:9.000 | chr11:63149671:63149681:A:11.000 | chr13:29238646:29238650:A:5.000 |
| chr12:55759486:55759493:A:8.000 | chr4:15938178:15938186:A:9.000 | chr1:120437095:120437102:A:8.000 |
| chr3:77657038:77657045:C:8.000 | chr3:170715684:170715693:A:10.000 | chr4:177094493:177094497:A:5.000 |
| chr1:150917624:150917631:C:8.000 | chr3:164905649:164905659:A:11.000 | chr9:22451066:22451070:A:5.000 |
| chrX:105937256:105937263:A:8.000 | chr3:136573486:136573494:A:9.000 | chrX:135404968:135404974:A:7.000 |
| chr11:62649529:62649536:A:8.000 | chr16:58589340:58589346:A:7.000 | chrX:147019049:147019056:A:8.000 |
| chr17:42756253:42756261:A:9.000 | chr17:33288434:33288444:A:11.000 | chr14:53237918:53237926:A:9.000 |
| chr5:79970915:79970922:A:8.000 | chr17:7193637:7193642:C:6.000 | chr1:182845333:182845339:A:7.000 |
| chr10:74653469:74653478:A:10.000 | chr7:77423460:77423468:A:9.000 | chr1:242162336:242162351:A:16.000 |
| chr4:13485808:13485815:0:8.000 | chr6:111587361:111587369:A:9.000 | chr9:112705848:112705855:A:8.000 |
| chr11:111953289:111953296:A:8.000 | chr22:36236338:36236352:C:15.000 | chr12:70091534:70091540:A:7.000 |
| chr9:100700506:100700516:A:11.000 | chr13:114538617:114538625:A:9.000 | chr13:37401948:37401954:A:7.000 |

TABLE B

MSI tumor only variable loci.

| locus | UCEC MSI f | UCEC MSI c | STAD MSI f | STAD MSI c | COAD MSI f | COAD MSI c | Total MSI cour | MSS info | Fraction of reads in the MSI allele | Fraction of Non mode reads | |
|---|---|---|---|---|---|---|---|---|---|---|---|
| chr2:148683686:148683693:A:8.000 | 0.183544 | 29 | 0.753623 | 52 | 0.8 | 23 | 113 | MSS_UCEC 1 MSS_STAD 0 MSS_COAD 1 | 0.0108219 | 0.0219465 | 243 144 558 51562 12880 3 0 0 0 1 0 0 0 |
| chr17:56435161:56435167:C:7.000 | 0.227848 | 36 | 0.347826 | 24 | 0.4 | 16 | 76 | MSS_UCEC 0 MSS_STAD 0 MSS_COAD 0 | 0.0106897 | 0.0552568 | 871 509 47616 1220 54 75 22 13 11 6 2 1 0 0 1 |
| chr3:30691872:30691881:A:10.000 | 0.101266 | 16 | 0.695652 | 48 | 0.25 | 10 | 74 | MSS_UCEC 0 MSS_STAD 0 MSS_COAD 1 | 0.117184 | 0.140036 | 28 152 123 349 4869 41550 1197 42 1 3 0 1 0 1 0 |
| chr1:62577785:62577792:A:8.000 | 0.240506 | 38 | 0.275362 | 19 | 0.25 | 10 | 67 | MSS_UCEC 0 MSS_STAD 0 MSS_COAD 0 | 0.0152167 | 0.161291 | 2095 3658 605 39759 319 908 56 5 0 0 0 0 0 0 |
| chr4:83785565:83785573:A:9.000 | 0.21519 | 34 | 0.318841 | 22 | 0.225 | 9 | 65 | MSS_UCEC 0 MSS_STAD 0 MSS_COAD 0 | 0.0391457 | 0.0594385 | 119 131 137 1701 43453 636 21 0 0 0 0 0 0 1 |
| chr18:57013194:57013202:A:9.000 | 0.21519 | 34 | 0.318841 | 22 | 0.225 | 9 | 65 | MSS_UCEC 0 MSS_STAD 0 MSS_COAD 0 | 0.0496595 | 0.0709538 | 256 151 220 2742 5521 6 468 319 54 6 1 0 0 0 0 0 |
| chr3:51417604:51417610:C:7.000 | 0.208861 | 33 | 0.246377 | 17 | 0.35 | 14 | 64 | MSS_UCEC 0 MSS_STAD 0 MSS_COAD 0 | 0.0299304 | 0.0814602 | 1445 1217 40661 906 20 3 1 3 0 0 1 6 4 0 0 |
| chr5:79970915:79970922:A:8.000 | 0.164557 | 26 | 0.405797 | 28 | 0.225 | 9 | 63 | MSS_UCEC 0 MSS_STAD 0 MSS_COAD 0 | 0.0240396 | 0.03524 | 164 151 1336 55575 306 72 1 0 0 0 0 0 0 0 |
| chr11:126137087:126137094:A:8.000 | 0.183544 | 29 | 0.347826 | 24 | 0.125 | 5 | 58 | MSS_UCEC 0 MSS_STAD 0 MSS_COAD 0 | 0.0311774 | 0.0460091 | 230 206 2026 64983 628 20 5 2 2 4 2 1 1 6 1 |
| chr7:77423460:77423468:A:9.000 | 0.126582 | 20 | 0.347826 | 24 | 0.3 | 12 | 56 | MSS_UCEC 0 MSS_STAD 0 MSS_COAD 0 | 0.0288291 | 0.0425784 | 137 125 139 1467 50886 377 9 1 0 0 3 3 1 0 1 |
| chr8:95686611:95686618:A:8.000 | 0.196203 | 31 | 0.202899 | 14 | 0.1 | 4 | 49 | MSS_UCEC 0 MSS_STAD 0 MSS_COAD 0 | 0.0127697 | 0.0321535 | 162 143 625 48944 177 451 62 3 0 2 1 0 0 0 |
| chr2:165551296:165551304:A:9.000 | 0.126582 | 20 | 0.289855 | 20 | 0.225 | 9 | 49 | MSS_UCEC 0 MSS_STAD 0 MSS_COAD 0 | 0.0442049 | 0.0806194 | 140 103 130 1340 30517 580 331 352 0 0 0 0 0 |
| chr20:47858504:47858511:A:8.000 | 0.107595 | 17 | 0.318841 | 22 | 0.225 | 9 | 48 | MSS_UCEC 0 MSS_STAD 0 MSS_COAD 0 | 0.0306204 | 0.0501407 | 201 202 1333 43533 537 19 1 1 4 0 0 0 0 0 |
| chr1:27621108:27621115:C:8.000 | 0.151899 | 24 | 0.15942 | 11 | 0.25 | 10 | 45 | MSS_UCEC 1 MSS_STAD 0 MSS_COAD 0 | 0.00771989 | 0.0457418 | 426 147 23 9 3 0959 630 38 3 1 0 0 0 0 0 0 |

TABLE B-continued

MSI tumor only variable loci.

| locus | UCEC MSI f | UCEC MSI c | STAD MSI f | STAD MSI c | COAD MSI f | COAD MSI c | Total MSI cour | MSS info | Fraction of reads in the MSI allele | Fraction of Non mode reads | |
|---|---|---|---|---|---|---|---|---|---|---|---|
| chr19:49850473:49850480:C:8.000 | 0.0886076 | 14 | 0.318841 | 22 | 0.225 | 9 | 45 | MSS_UCEC 0 MSS_STAD 0 MSS_COAD 0 | 0.0122884 | 0.0532461 | 529353 567 46141 1010 107 18 0 0 5 2 4 0 0 0 |
| chr11:122242658:122242665:C:8.000 | 0.196203 | 31 | 0 | 0 | 0.325 | 13 | 44 | MSS_UCEC 1 MSS_STAD 0 MSS_COAD 0 | 0.0200378 | 0.167367 | 457 161 286 14273 171 607 441 22 144 340 16 88 97 7 32 |
| chr3:100039736:1000397H.A:9.000 | 0.120253 | 19 | 0.144928 | 10 | 0.35 | 14 | 43 | MSS_UCEC 0 MSS_STAD 0 MSS_COAD 0 | 0.0397053 | 0.0639163 | 143 88 145 1509 38005 544 152 13 1 0 0 0 0 0 |
| chr19:49458071:49458978:C:8.000 | 0.0886076 | 14 | 0.26087 | 18 | 0.25 | 10 | 42 | MSS_UCEC 0 MSS_STAD 0 MSS_COAD 0 | 0.0131636 | 0.0946468 | 1861 651 549 41706 710 75 118 46 10 1 2 1 2 1 3 |
| chrX:37312611:37312618:C:8.000 | 0.164557 | 26 | 0.130435 | 9 | 0.125 | 5 | 40 | MSS_UCEC 0 MSS_STAD 0 MSS_COAD 0 | 0.0160236 | 0.123825 | 239 393 799 49864 515 226 674 266 2049 98 1574 144 25 36 9 |
| chr12:57422573:57422580:A:8.000 | 0.101266 | 16 | 0.275362 | 19 | 0.125 | 5 | 40 | MSS_UCEC 1 MSS_STAD 0 NSS_COAD 0 | 0.0248444 | 0.0409294 | 151 161 1325 53332 442 163 25 6 2 0 1 0 0 0 |
| chr1:65306997:65307004:A:8.000 | 0.208861 | 33 | 0.057971 | 4 | 0 | 0 | 37 | MSS_UCEC 0 MSS_STAD 0 MSS_COAD 0 | 0.0100689 | 0.0252539 | 227 153 520 51644 300 116 16 6 0 0 0 0 0 0 |
| chr5:137451362:137451371:A:10.000 | 0.113924 | 18 | 0.188406 | 13 | 0.15 | 6 | 37 | MSS_UCEC 0 MSS_STAD 0 MSS_COAD 0 | 0.0352783 | 0.115803 | 92 106 58 108 1179 33420 2559 140 26 82 25 1 1 0 0 |
| chr11:118220583:118220591:A:9.000 | 0.120253 | 19 | 0.0869565 | 6 | 0.275 | 11 | 36 | MSS_UCEC 0 MSS_STAD 0 MSS_COAD 0 | 0.0236754 | 0.0476116 | 100 76 123 1013 42787 687 9S 12 3 10 7 3 0 0 0 |
| chr6:100382358:100382366:A:9.000 | 0.0822785 | 43 | 0.15942 | 11 | 0.3 | 12 | 36 | MSS_UCEC 0 MSS_STAD 0 MSS_COAD 1 | 0.0289566 | 0.046018 | 244 125 110 1248 43099 335 16 1 0 0 0 0 0 0 |
| chr11:62649529:62649536:A:8.000 | 0.0822785 | 13 | 0.188406 | 13 | 0.225 | 9 | 35 | MSS_UCEC 0 MSS_STAD 0 MSS_COAD 0 | 0.0171703 | 0.0299304 | 253 140 783 45602 153 74 3 1 0 0 0 0 0 0 0 |
| chr8:103289349:103289356:A:8 000 | 0.0506329 | 8 | 0.304348 | 21 | 0.15 | 6 | 35 | MSS_UCEC 0 MSS_STAD 0 MSS_COAD 0 | 0.0193358 | 0.0343893 | 249 164 1151 59527 451 24 74 6 0 0 1 0 0 0 |
| chr2:203922058:203922066:A:9.000 | 0.132911 | 21 | 0 | 0 | 0.35 | 14 | 35 | MSS_UCEC 0 MSS_STAD 0 MSS_COAD 0 | 0.0406737 | 0.0590706 | 63 59 89 966 23750 221 24 3 0 2 1 54 7 2 0 |
| chr9:136918529:136918536:C:8.000 | 0.101266 | 16 | 0.115942 | 8 | 0.2 | 8 | 32 | MSS_UCEC 0 MSS_STAD 0 MSS_COAD 0 | 0.0259647 | 0.10205 | 603 146 687 26450 546 43 17 798 153 12 0 1 1 0 0 |

TABLE B-continued

MSI tumor only variable loci.

| locus | UCEC MSI f | UCEC MSI c | STAD MSI f | STAD MSI c | COAD MSI f | COAD MSI c | Total MSI cour | MSS info | Fraction of reads in the MSI allele | Fraction of Non mode reads | |
|---|---|---|---|---|---|---|---|---|---|---|---|
| chr1:2311131567:231131575:A:9.000 | 0.0949367 | 15 | 0.15942 | 11 | 0.15 | 6 | 32 | MSS_UCEC 0 MSS_STAD 0 MSS_COAD 0 | 0.0453718 | 0.0710862 | 134 117 250 2119 46703 905 48 1 0 0 0 0 0 0 |
| chr10:111893350:111893355A:8.000 | 0.0759494 | 12 | 0.188406 | 13 | 0.15 | 6 | 31 | MSS_UCEC 0 MSS_STAD 0 MSS_COAD 0 | 0.0135957 | 0.0242316 | 108 73 467 34349 132 0 0 1 2 4 2 4 52 7 1 |
| chr16:85682290:85682297:C:8.000 | 0.151899 | 24 | 0.0869565 | 6 | 0.025 | 1 | 31 | MSS_UCEC 0 MSS_STAD 0 MSS_COAD 0 | 0.0160495 | 0.0724208 | 362 257 628 39129 524 1199 68 9 1 0 1 3 1 0 2 |
| chr16:10867203:10867211:A:9.000 | 0.0822785 | 13 | 0.144928 | 10 | 0.2 | 8 | 31 | MSS_UCEC 0 MSS_STAD 0 MSS_COAD 0 | 0.0285979 | 0.0592494 | 99 115 140 1048 36646 765 115 9 1 9 6 1 0 0 0 |
| chr17:48433967:48433973:C:7.000 | 0.0506329 | 8 | 0.202899 | 14 | 0.15 | 6 | 28 | MSS_UCEC 0 MSS_STAD 0 MSS_COAD 0 | 0.011575 | 0.0744894 | 585 407 35162 1748 54 23 4 1 0 1 2 5 0 0 0 |
| chr15:79750586:79750593:A:8.000 | 0.0632911 | 10 | 0.173913 | 12 | 0.15 | 6 | 28 | MSS_UCEC 0 MSS_STAD 0 MSS_COAD 0 | 0.0137885 | 0.0255068 | 108 139 580 42064 270 4 0 00 0 0 0 0 0 0 |
| chr1:35846960:35846968:A:9.000 | 0.094936 | 15 | 0.130435 | 9 | 0.1 | 4 | 28 | MSS_UCEC 0 MSS_STAD 0 MSS_COAD 0 | 0.0291119 | 0.0486433 | 149121 139 1379 47369 623 11 0 0 0 0 0 0 0 0 |
| chr12:55759486:55550403:A:8.000 | 0.0506329 | 8 | 0.144928 | 10 | 0.225 | 9 | 27 | MSS_UCEC 0 MSS_STAD 0 MSS_COAD 0 | 0.0178565 | 0.0274322 | 247 143 980 54882 172 5 0 0 0 0 1 0 0 0 0 |
| chr20:49508204:49508211:A:8.000 | 0.0759494 | 12 | 0.130435 | 9 | 0.15 | 6 | 27 | MSS_UCEC 0 MSS_STAD 0 MSS_COAD 0 | 0.0248433 | 0.0371817 | 164 136 1304 52489 414 9 0 0 0 0 0 0 0 0 0 |
| chr1:155308000:155308008:A:9.000 | 0.0949367 | 15 | 0.115942 | 8 | 0.1 | 4 | 27 | MSS_UCEC 0 MSS_STAD 0 MSS_COAD 0 | 0.0288317 | 0.0652227 | 378186 163 1538 53344 1268 170 9 8 2 0 0 0 0 0 |
| chr5:131931452:131931460:A:9.000 | 0.0759494 | 12 | 0.15942 | 11 | 0.1 | 4 | 27 | MSS_UCEC 0 MSS_STAD 0 MSS_COAD 0 | 0.037512 | 0.0559682 | 118 57 93 1249 33296 390 29 1 2 0 23 10 1 0 1 |
| chr17:7798765:7798771:C:7.000 | 0.126582 | 20 | 0.0289855 | 2 | 0.1 | 4 | 26 | MSS_UCEC 0 MSS_STAD 0 MSS_COAD 0 | 0.00735492 | 0.0524451 | 284 356 48403 607 42 25 1108 46 85 77 11 6 11 12 9 |
| chr15:64967247:64967254:A:8.000 | 0.056962 | 9 | 0.202899 | 14 | 0.075 | 3 | 26 | MSS_UCEC 0 MSS_STAD 0 MSS_COAD 0 | 0.0111528 | 0.0224342 | 105 99 416 37300 135 61 31 4 4 0 0 0 0 0 1 |
| chr1:240-8404:240-8411:A:8.000 | 0.0316456 | 5 | 0.26087 | 18 | 0.075 | 3 | 26 | MSS_UCEC 0 MSS_STAD 0 MSS_COAD 0 | 0.0112486 | 0.0198134 | 137 95 468 41605 138 1 1 1 0 0 0 0 0 0 |
| chr21:58524243:38524250:A:8.000 | 0.0822785 | 13 | 0.0869565 | 6 | 0.175 | 7 | 26 | MSS_UCEC 0 MSS_STAD 0 MSS_COAD 0 | 0.019008 | 0.0325124 | 224 120 1073 56450 401 17 50 4 0 1 1 0 1 1 4 |
| chr4:3015470:3015478:A:9.000 | 0.0696203 | 11 | 0.15942 | 11 | 0.1 | 4 | 26 | MSS_UCEC 1 MSS_STAD 0 MSS_COAD 0 | 0.0307455 | 0.0524052 | 181 144 148 1436 46706 360 178 60 0 4 4 33 5 14 16 |

TABLE B-continued

MSI tumor only variable loci.

| locus | UCEC MSI f | UCEC MSI c | STAD MSI f | STAD MSI c | COAD MSI f | COAD MSI c | Total MSI cour | MSS info | Fraction of reads in the MSI allele | Fraction of Non mode reads | |
|---|---|---|---|---|---|---|---|---|---|---|---|
| chr18:20572853:20572861:A:9.000 | 0.0632911 | 10 | 0.144928 | 10 | 0.15 | 6 | 26 | MSS_UCEC 0<br>MSS_STAD 0<br>MSS_COAD 0 | 0.0365144 | 0.0610589 | 203 193 150 1762 48255 661 128 34 7 0 0 0 0 0 |
| chr3:114058003:114058009:C:7.000 | 0.0696203 | 11 | 0.115942 | 8 | 0.15 | 6 | 25 | MSS_UCEC 0<br>MSS_STAD 0<br>MSS_COAD 0 | 0.00585386 | 0.0417246 | 232 226 38607 1140 70 8 4 1 0 0 0 0 0 0 |
| chr2:234638283:234638290:A:8.000 | 0.0822785 | 13 | 0.144928 | 10 | 0.05 | 2 | 25 | MSS_UCEC 0<br>MSS_STAD 0<br>MSS_COAD 0 | 0.0144656 | 0.0301676 | 193 211 1011 69890 608 143 4 3 0 0 1 0 0 0 |
| ch8:37791834:37791842:A:9.000 | 0.0506329 | 8 | 0.130435 | 9 | 0.2 | 8 | 25 | MSS_UCEC 0<br>MSS_STAD 0<br>MSS_COAD 1 | 0.024037 | 0.0538073 | 123 132 105 1293 53792 1249 141 12 0 1 3 0 0 0 |
| chr10:98336475:98336482:A:8.000 | 0.0443038 | 7 | 0.188406 | 13 | 0.125 | 5 | 25 | MSS_UCEC 0<br>MSS_STAD 0<br>MSS_COAD 0 | 0.0294004 | 0.0382195 | 196 165 1604 54557 194 5 2 2 0 0 0 0 0 0 |
| ch9:33675365:33675373:A:9.000 | 0.056962 | 9 | 0.057971 | 4 | 0.275 | 11 | 24 | MSS_UCEC 0<br>MSS_STAD 0<br>MSS_COAD 0 | 0.0333333 | 0.0762317 | 109 92 95 740 22200 736 52 8 0 0 0 0 0 0 |
| chr3:157081227:157081235:A:9.000 | 0.0443038 | 7 | 0.115942 | 8 | 0.2 | 8 | 23 | MSS_UCEC 0<br>MSS_STAD 0<br>MSS_COAD 0 | 0.0292438 | 0.0470584 | 154 141 192 1593 54473 592 140 1 1 0 1 1 0 0 |
| chr10:97918856:97918864:A:9.000 | 0.018987 | 3 | 0.173913 | 12 | 0.2 | 8 | 23 | MSS_UCEC 0<br>MSS_STAD 0<br>MSS_COAD 0 | 0.0357041 | 0.0573403 | 175 104 112 1252 35066 420 17 36 8 1 6 2 0 0 0 |
| chr3:142274740:142274749:A:10.000 | 0.0632911 | 10 | 0.130435 | 9 | 0.1 | 4 | 23 | MSS_UCEC 0<br>MSS_STAD 0<br>MSS_COAD 0 | 0.0178236 | 0.0922382 | 417 99 81 172 2037 42594 1373 12714 3 3 10 1 0 |
| chrX:105937256:105937263:A:8.000 | 0.056962 | 9 | 0.0869565 | 6 | 0.175 | 7 | 22 | MSS_UCEC 0<br>MSS_STAD 0<br>MSS_COAD 0 | 0.0163955 | 0.028463 | 101 104 793 48367 398 19 1 1 0 0 0 0 0 0 |
| chr15:91304139:91304147:A:9.000 | 0.0316456 | 5 | 0.15942 | 11 | 0.15 | 6 | 22 | MSS_UCEC 0<br>MSS_STAD 0<br>MSS_COAD 0 | 0.0234382 | 0.0446429 | 127 00 76 795 33919 485 5 0 1 1 3 1 0 0 1 |
| chr1:93667516:93667524:A:9.000 | 0.056962 | 9 | 0.101449 | 7 | 0.15 | 6 | 22 | MSS_UCEC 0<br>MSS_STAD 0<br>MSS_COAD 0 | 0.0355489 | 0.0893333 | 1737 1 154 1397 39298 353 74 5 3 12 1 3 4 1 0 |
| chr6:163899920:163899927:A:8.000 | 0.0506329 | 8 | 0.115942 | 8 | 0.15 | 6 | 22 | MSS_UCEC 0<br>MSS_STAD 0<br>MSS_COAD 0 | 0.0452545 | 0.0535808 | 235 137 2211 48857 140 39 4 0 0 0 0 0 0 0 |
| chr10:29760116:29760122:C:7000 | 0.0443038 | 7 | 0.057971 | 4 | 0.25 | 10 | 21 | MSS_UCEC 0<br>MSS_STAD 0<br>MSS_COAD 0 | 0.00668787 | 0.0362364 | 561 246 36783 497 20 1 8 1 0 36 2 11 0 0 0 |
| chr4:186272695:186272702:A:8.000 | 0.0632911 | 10 | 0.0724638 | 5 | 0.15 | 6 | 21 | MSS_UCEC 0<br>MSS_STAD 1<br>MSS_COAD 0 | 0.0123085 | 0.0207144 | 115152 572 46472 142 2 0 0 0 0 0 0 0 0 |
| chr2:74687410:74687417:C:8.000 | 0.0822785 | 13 | 0.057971 | 4 | 0.1 | 4 | 21 | MSS_UCEC 0<br>MSS_STAD 0<br>MSS_COAD 0 | 0.0149447 | 0.112159 | 523 273 671 44899 1096 126 |

TABLE B-continued

MSI tumor only variable loci.

| locus | UCEC MSI f | UCEC MSI c | STAD MSI f | STAD MSI c | COAD MSI f | COAD MSI c | Total MSI cour | MSS info | Fraction of reads in the MSI allele | Fraction of Non mode reads | |
|---|---|---|---|---|---|---|---|---|---|---|---|
| | | | | | | | | | | | 1978 90 304 27 9 1 306 6 36 145 |
| chr6:139097330:139097337:A:8.000 | 0.0696203 | 11 | 0.0724638 | 5 | 0.125 | 5 | 21 | MSS_UCEC 0 MSS_STAD 0 MSS_COAD 1 | 0.0259696 | 0.0369591 | 196 138 1283 49404 269 10 0 0 0 0 0 0 0 0 |
| chr16-67645339:67645345:A:7000 | 0.0949367 | 15 | 0.057971 | 4 | 0.025 | 1 | 20 | MSS_UCEC 3 MSS_STAD 0 MSS_COAD 0 | 0.00606684 | 0.0132775 | 193 289 47636 97 1 2 32 3 0 0 0 23 1 0 0 |
| chr10:89717770:89717775:A:6.000 | 0.0696203 | 11 | 0.057971 | 4 | 0.125 | 5 | 20 | MSS_UCEC 0 MSS_STAD 0 MSS_COAD 0 | 0.00837608 | 0.00925154 | 418 49904 46 0 1 0 0 0 1 0 0 0 0 |
| chrX:13764946:13764954:A:9.000 | 0.0886076 | 14 | 0.0869565 | 6 | 0 | 0 | 20 | MSS_UCEC 2 MSS_STAD 0 MSS_COAD 0 | 0.0402559 | 0.0586101 | 241 179 152 1932 47993 461 14 5 21 0 0 0 0 1 |
| chr10:70182521:70182529:A:9.000 | 0.056962 | 9 | 0.0724638 | 5 | 0.15 | 6 | 20 | MSS_UCEC 0 MSS_STAD 0 MSS_COAD 0 | 0.0461884 | 0.077774 | 151 154 173 1625 35182 794 63 6 1 0 0 0 0 0 0 |
| chr2:207174428:207174436:A:9.000 | 0.0316456 | 5 | 0.0869565 | 6 | 0.2 | 8 | 19 | MSS_UCEC 1 MSS_STAD 0 MSS_COAD 0 | 0.02323 | 0.0483792 | 126 100 109 817 35170 544 73 16 1 0 0 0 1 0 1 |
| ch7:8198251:198259:A:9.000 | 0.0632911 | 10 | 0.0434783 | 3 | 0.15 | 6 | 19 | MSS_UCEC 0 MSS_STAD 0 MSS_COAD 0 | 0.0340801 | 0.0503921 | 175 92141 1655 48562 499 12 3 0 0 0 0 0 0 0 |
| chr17:42756253:42756261:A:9.000 | 0.0632911 | 10 | 0.0434783 | 3 | 0.15 | 6 | 19 | MSS_UCEC 0 MSS_STAD 0 MSS_COAD 0 | 0.0438134 | 0.0729985 | 288 141 171 1944 44370 806 15 2 0 1 7 6 49 1 0 0 |
| chrX:129190011:129190017:C:7.000 | 0.0443038 | 7 | 0.115942 | 8 | 0.075 | 3 | 18 | MSS_UCEC 0 MSS_STAD 0 MSS_COAD 0 | 0.0127043 | 0.0986363 | 1614 440 34634 1591 130 9 1 0 1 3 1 0 0 0 0 |
| chr12:416953:416960:A:8.000 | 0.0506329 | 8 | 0.101449 | 7 | 0.075 | 3 | 18 | MSS_UCEC 0 MSS_STAD 0 MSS_COAD 0 | 0.0158634 | 0.0346183 | 245 124 783 49359 599 13 3 1 1 0 1 0 0 0 0 |
| chr6:158508009:158508016:C:8.000 | 0.063291 | 10 | 0.0869565 | 6 | 0.05 | 2 | 18 | MSS_UCEC 0 MSS_STAD 0 MSS_COAD 0 | 0.016687 | 0.134767 | 152 149 437 26188 1040 57 1410 705 101 15 8 2 1 1 1 |
| chr5:140049102:140049109:A:8:000 | 0.056962 | 9 | 0.0289855 | 2 | 0.175 | 7 | 18 | MSS_UCEC 0 MSS_STAD 0 MSS_COAD 0 | 0.0285018 | 0.0445202 | 160 129 983 34489 326 7 2 0 0 0 0 0 0 0 |
| chr6:84896233:84896240:A:8.000 | 0.0379747 | 6 | 0.101449 | 7 | 0.125 | 5 | 18 | MSS_UCEC 0 MSS_STAD 0 MSS_COAD 0 | 0.0291754 | 0.0374846 | 159 152 1550 53127 205 2 1 0 0 0 0 0 0 0 0 |
| chr20:58467047:58467055:A:9.000 | 0.0696203 | 11 | 0.057971 | 4 | 0.075 | 3 | 18 | MSS_UCEC 0 MSS_STAD 0 MSS_COAD 0 | 0.0413787 | 0.0624438 | 111 113 106 1898 45869 645 11 11 117 38 4 1 0 0 0 |
| chr6:90432675:90432682:A:8.000 | 0.0443038 | 7 | 0.101449 | 7 | 0.075 | 3 | 17 | MSS_UCEC 0 MSS_STAD 0 MSS_COAD 0 | 0.019963 | 0.0316037 | 131 97 972 48600 288 87 12 1 1 0 0 0 0 0 |

TABLE B-continued

MSI tumor only variable loci.

| locus | UCEC MSI f | UCEC MSI c | STAD MSI f | STAD MSI c | COAD MSI f | COAD MSI c | Total MSI cour | MSS info | Fraction of reads in the MSI allele | Fraction of Non mode reads | |
|---|---|---|---|---|---|---|---|---|---|---|---|
| chr7:100802 405:1008024 12:C:8.000 | 0.056962 | 9 | 0.057971 | 4 | 0.075 | 3 | 16 | MSS_UCEC 0 MSS_STAD 0 MSS_COAD 0 | 0.0125963 | 0.0471075 | 251 207 438 34772 766 35 15 5 1 0 0 1 0 0 0 |
| chr4:150056 80:15005687: A.000 | 0.0443038 | 7 | 0.0869565 | 6 | 0.075 | 3 | 16 | MSS_UCEC 0 MSS_STAD 0 MSS_COAD 0 | 0.028541 | 0.0379444 | 155 132 1448 50734 225 34 4 2 1 0 0 0 0 0 0 |

In cases where whole genome or whole exome data are not available, one can sequence a small set of loci that are highly mutated in microsatellite instability (MSI) cases but have a low indel rate in MSS cases. A set of about 20 loci is almost always sufficient for MSI classification. Those 20 loci or so tend to differ between different tumor types. For example, colon adenocarcinoma contains different loci than endometrial.

In one embodiment, the cancer or tumor may be colon adenocarcinoma (COAD), stomach adenocarcinoma (STAD), or uterine corpus endometrial carcinoma (UCEC). In another embodiment, the cancer or tumor may be other than colon adenocarcinoma (COAD), stomach adenocarcinoma (STAD), or uterine corpus endometrial carcinoma (UCEC).

In an embodiment wherein the cancer or tumor may be colon adenocarcinoma (COAD), the limited plurality of microsatellite indels detected may comprise at least 5, at least 10 or at least 20 MS indels from a list of COAD MS indels, such as the 20 COAD MS indels in Table A or Table B.

In an embodiment wherein the cancer or tumor is stomach adenocarcinoma (STAD), the limited plurality of microsatellite indels detected may comprise at least 5, at least 10 or at least 20 MS indels from a list of STAD MS indels, such as the list of 20 STAD MS indels in Table A or Table B.

In an embodiment wherein the cancer or tumor is uterine corpus endometrial carcinoma (UCEC), the limited plurality of microsatellite indels detected may comprise at least 5, at least or at least 20 MS indels MS indels from a list of UCEC MS indels, such as the list of 20 UCEC MS indels in Table A or Table B.

In an embodiment wherein the cancer or tumor is other than colon adenocarcinoma (COAD), stomach adenocarcinoma (STAD), or uterine corpus endometrial carcinoma (UCEC), the limited plurality of microsatellite indels detected may comprise at least 5, at least or at least 20 MS indels from a list of MS indels for cancers other than COAD, STAD, or UCEC, such as the list of 20 such MS indels for cancers other than COAD, STAD, or UCEC in Table A or Table B.

The method of the present disclosure also includes identifying one or more somatic indels in a microsatellite (MS) locus (MS indels) in one or more genes that are identified by MSMutSig. The one or more MS indels may be in one or more of the ACVR2A, RNF43, DOCK3, MSH3, ESRP1, PRDM2 and/or JAK1 genes. The one or more MS indels may be in one or more of the ESRP1, PRDM2, or DOCK3 JAK1 genes. The cancer or tumor may be COAD, STAD or UCEC, and the MS indel may be selected from the respective/corresponding MS indels listed in Table C of significantly mutated MS loci for COAD, STAD and UCEC cancers or tumors.

An alternative is low depth whole genome sequencing. While with low depth sequencing one cannot be very confident about any given locus, by aggregating the information from many loci together one can still correctly classify the samples as being MSI-H or MSS. The advantage of this low depth approach is that it can be inexpensive and can be applied using pre-existing protocols. One can thus simultaneously obtain both CNVs (copy number variations) estimations and MSI-H classification. One of skill in the art will appreciate that detection of sequence variants is well known, and examples of such methodologies may be found in, for example, International Patent Application No. PCT/US13/57128, filed Aug. 28, 2013, and U.S. patent application Ser. No. 14/633,321; and International Patent Application No. PCT/US2014/028268, filed Mar. 14, 2014, and U.S. patent application Ser. No. 14/854,682 filed Sep. 15, 2015.

As a low cost option, MSI cases may be classified based on existing clinically used small gene sets, both by counting how many events they contain, and by the mutational patterns of their events, similar to the approach suggested for WES/WGS. Even though the covered region of the genome in these loci is small, they usually have a high depth that can enable the detection of many events that exist in a very low allele fraction. Knowledge of the special patterns of the MSI-H indels may serve as a diagnostic tool, as it could help distinguish between noise and real MSI indels events.

In some cases a normal sample (either blood or other tissue) is not available. Thus the mutation calling is problematic as there is no reference that can be used to determine if there is an indel in the tumor. This reference is needed for the current gold standard tests, as they use a set of loci that tend to have a large variability in the germline. Thus, without a normal sample one cannot detect the presence of a mutation in the tumor even if its number of repeats is different than the reference genome.

The techniques herein found that there are many loci that have no (or at least very low) variability in the germline. While these loci have a high mutation rate in MSI tumors, they are usually in the coding region of the genome. Thus, a list of loci that are highly mutated in the MSI-H cases, while having very low variability in the germline, was generated and can be used to classify MSI-H cases by using tumor-only samples.

The present disclosure relates to modifying MuTect to detect somatic MS indels from next-generation sequencing (NGS) data. The present disclosure also relates to modifying MutSig to detect loci and genes with an increased frequency of MS indels.

MuTect (see, e.g., international patent application no. PCT/US13/57128 and Cibulskis, K. et al. Sensitive detection of somatic point mutations in impure and heterogeneous cancer samples. Nat Biotechnology (2013).doi:10.1038/nbt.2514) generally has three steps:

1. Preprocessing the aligned reads in the tumor and normal sequencing data. In this step, reads with too many mismatches or very low quality scores are ignored since these represent noisy reads that introduce more noise than signal.

2. A statistical analysis that identifies sites that are likely to carry somatic mutations with high confidence. The statistical analysis predicts a somatic mutation by using two Bayesian classifiers—the first aims to detect whether the tumor is non-reference at a given site and, for those sites that are found as non-reference, the second classifier makes sure the normal does not carry the variant allele. In practice the classification is performed by calculating a LOD score (log odds) and comparing it to a cutoff determined by the log ratio of prior probabilities of the considered events. For the tumors the following calculations are made:

$$LOD_t = \log_{10}\left(\frac{P(\text{observed data in tumor}|\text{site is mutated})}{P(\text{observed data in tumor}|\text{site is reference})}\right)$$

and for the normal:

$$LOD_N = \log_{10}\left(\frac{P(\text{observed data in normal}|\text{site is reference})}{P(\text{observed data in normal}|\text{site is mutated})}\right)$$

Since somatic mutations are expected to occur at a rate of ~1 in a Mb, $LOD_t > \log_{10}(0.5 \times 10^{-6}) \approx 6.3$ is required to guarantee that the false positive rate, due to noise in the tumor, is less than half of the somatic mutation rate. In the normal, not in dbSNP sites, $LOD_N > \log_{10}(0.5 \times 10^{-2}) \approx 2.3$ is required since non-dbSNP germline variants occur roughly at a rate of 100 in a Mb. This cutoff guarantees that the false positive somatic call rate, due to missing the variant in the normal, is also less than half the somatic mutation rate.

3. Post-processing of candidate somatic mutations to eliminate artifacts of next-generation sequencing, short read alignment and hybrid capture. For example, sequence context can cause hallucinated alternate alleles but often only in a single direction. Therefore, the alternate alleles are tested to support that the mutations are observed in both directions.

A schematic version of MSMuTect is presented in FIG. 1. All reads containing an MS region and sufficient 3' and 5' flanking sequence are aligned to a collection of all MS loci and the number of reads supporting each MS length are tallied to create a histogram of observed read lengths per locus. The length histograms for all sites that share the same underlying motif and number of repeats (i.e., sites with the same motif and mode length) from the X chromosome of male normal samples were combined into a single histogram. This combined histogram represents the empirical noise distribution (i.e., the probability that a true allele with i repeats will generate a read with j repeats). The maximum likelihood method and empirical noise distribution are used to identify the set of alleles that best describes the histogram for a given locus. This set includes the number of alleles, the length of each allele, and the fraction of DNA molecules representing each allele in the sample. After determining the most likely allele for both the tumor and normal sample, somatic MS indels are nominated when the tumor model fits the tumor data better than the normal model fits the tumor data and vice versa.

MutSig stands for "Mutation Significance" (see, e.g., U.S. patent application Ser. No. 14/854,682 and Lawrence, M. et al. Mutational heterogeneity in cancer and the search for new cancer-associated genes. Nature 499, 214-218 (2013)). MutSig analyzes lists of mutations discovered in DNA sequencing, to identify genes that were mutated more often than expected by chance given background mutation processes.

The input data to MutSig is lists of mutations (and indels) from a set of samples (patients) that were subjected to DNA sequencing, as well as information about how much territory was covered in the sequencing. MutSig was originally developed for analyzing somatic mutations, but it has also been useful in analyzing germline mutations. MutSig builds a model of the background mutation processes that were at work during formation of the tumors, and it analyzes the mutations of each gene to identify genes that were mutated more often than expected by chance, given the background model.

First, tumors are aggregated together and mutations are tallied, and then a score and p-value are calculated for each gene. A significance threshold is chosen to control the False Discovery Rate (FDR), and genes exceeding this threshold are reported as significantly mutated.

An important component of MutSigCV is the background model for mutations, the probability that a base is mutated by chance. Patients being analyzed do not all have the same background mutation rate, or the same spectrum of mutations. Similarly, not all regions of the genome (or exome) have the same background mutation patterns.

MutSig has been evolving since the early days of clinical sequencing, and several versions have been in use:

MutSig1.0 assumed a constant background mutation rate (BMR) across the genome.

MutSig1.5 implemented a rudimentary estimate of per-gene background mutation rates from analyzing the silent (synonymous) mutations of each gene and the rough expression level of the gene.

MutSig2.0, although named similarly to the above versions, is actually rather different. While the versions listed above consider the *abundance* of mutations above background, this part of MutSig looks at two additional independent signals of positive selection in genes: the *clustering* of mutations in hotspots, and the functional impact of the mutations, which can be estimated in a number of ways (PolyPhen, SIFT, CHASM, Mutation Assessor, etc.), or even simply from the *conservation* of the sites—that is, how conserved they were during vertebrate evolution. These two signals are then combined with each other and with the results of MutSig 1.5 to yield a final measure of significance that takes all three signals (Abundance, Clustering, and Conservation) into account.

MutSigS2N was a rudimentary precursor of MutSigCV, used in a few interim projects before MutSigCV was developed.

MutSigCV is the most current version of the algorithm. The "CV" stands for "covariates". MutSigCV starts from the observation that the data is very sparse, and that there are usually too few silent mutations in a gene for its BMR to be estimated with any confidence. MutSigCV improves the BMR estimation by pooling data from 'neighbor' genes in covariate space. These neighbor genes are chosen on the basis of having similar genomic properties to the central gene in question: properties such as DNA replication time, chromatin state (open/closed), and general level of transcription activity (e.g. highly transcribed vs. not transcribed at all). These genomic parameters have been observed to strongly correlate (co-vary) with background mutation rate. For instance, genes that replicate early in S-phase tend to have much lower mutation rates than late-replicating genes. Genes that are highly transcribed also tend to have lower mutation rates than unexpressed genes, due in part to the effects of transcription-coupled repair (TCR). Genes in closed chromatin (as measured by HiC or ChipSeq) have higher mutation rates than genes in open chromatin. Incorporating these covariates into the background model substantially reduces the number of false-positive findings.

MSMutSig searches for MS loci that are mutated significantly more frequently than expected by chance. The techniques herein found that the main two covariates that influence the mutation rate at MS loci are the specific motif and the number of repeats, while other covariates that are known to influence SNV rates (such as replication timing) have minimal effect on MS mutation rates. Thus, the techniques herein estimated the background mutation frequency for each motif and repeat length in every tumor type separately. Additionally, it was estimated that the rates (and tested the significance) of loci that contained at least one MS mutation across the analyzed cohort. These conditional rates (ie. conditional on observing at least one event) were calculated since it was observed that there was a wide variability of mutation rates with a significant enrichment of sites with no mutation. Estimating the mutation rate including these "stable" sites underestimate the overall background rate and hence inflate the list of significantly mutated loci.

It was concluded that there is a subset of MS loci that are less prone to MS indels and should be excluded from the estimation. Even after excluding these "stable" sites, there was still a large variability of mutation rates among MS loci with the same motif and repeat length, beyond the variability one would expect from a binomial distribution assuming all sites had the same underlying background mutation rate. This high variability was observed even among loci that reside in genomic regions that are less likely to harbor functionally relevant MS loci than exons, such as UTR's and introns. Therefore, an additional variable was included to attempt to capture this increased variability. A negative-binomial distribution (also known as the gamma-Poisson), which has two parameters that control the mean and the variability around the mean, was used. The mean was set to reflect the average mutation rate (at sites with at least one MS indel), and then tuned the variability such that no significant loci were identified outside the exome (with FDR q<0.1). These parameters were then used to identify significantly mutated MS loci in the coding regions.

The methodology presented below is an advantageous embodiment as to how to practice the presently claimed disclosure and is in no way limiting to the scope of the disclosure.

Whole exome sequence (WES) data from 20 tumor types were downloaded from The Cancer Genome Analysis (TCGA) website (see for example the World Wide Web at (www)tcga-data.nci.nih.gov/docs/publications/tcga/)[58] (Supplementary Table S2). The analysis was restricted to fresh frozen samples sequenced on an Illumina platform.

For comparison with previously identified mutations, MAF files were downloaded from the Broad Institute's Genome Data Analysis Center (GDAC; see for example the World Wide Web at (www)gdac.broadinstitute.org/), which includes data from samples used in the TCGA marker papers (see for example the World Wide Web at (www)tcga-data.nci.nih.gov/docs/publications). Microsatellite (MS) indels were also analysed in additional TCGA samples that were not part of the TCGA marker papers, but these did not have a curated MAF file for comparison.

The three BAM files for case NA12878 from the 1000 Genome project[18] (see for example the World Wide Web at (www)internationalgenome.org/) which were used for the false positive and false negative analysis were deposited at the FireClouad. All three of these samples were sequenced at the Broad Institute.

Microsatellite (MS) definition and identification. Microsatellites (MS) are genomic regions containing multiple copies of a repetitive motif of 1-6 basepairs (bps). While there is no consensus regarding the number of consecutive motifs required to constitute a microsatellite. The techniques herein define a MS locus as a sequence with at least five successive motifs, regardless of the motif size. The techniques herein allowed the MS sequence to have impurities, e.g., bases that do not follow the exact repeated motif structure. For example, the techniques herein considered the sequence . . . GTCAAAAAAAACAAAAAAAAAATCC . . . as one MS locus with 17 repeats of an A motif, rather than two MS loci, each containing 8 repeats of an A motif. The techniques herein allowed up to 15% impurity (e.g., up to 15% bases that do not match the exact motif), and used the PHOBOS algorithm[16] with default parameters to identify MS with impurities in both the reference genome and WES sequencing reads. Note that the techniques herein do not suggest that impurities are errors in the reference genome, but rather reflect the looser definition of MSs. The techniques herein identified 23,677,217 MS loci in the whole genome, 383,515 MS loci in the regions covered by the TCGA whole exome Illumina data, and 145,516 MS loci in the coding regions (as defined by Oncotator[59]).

Figure 8:
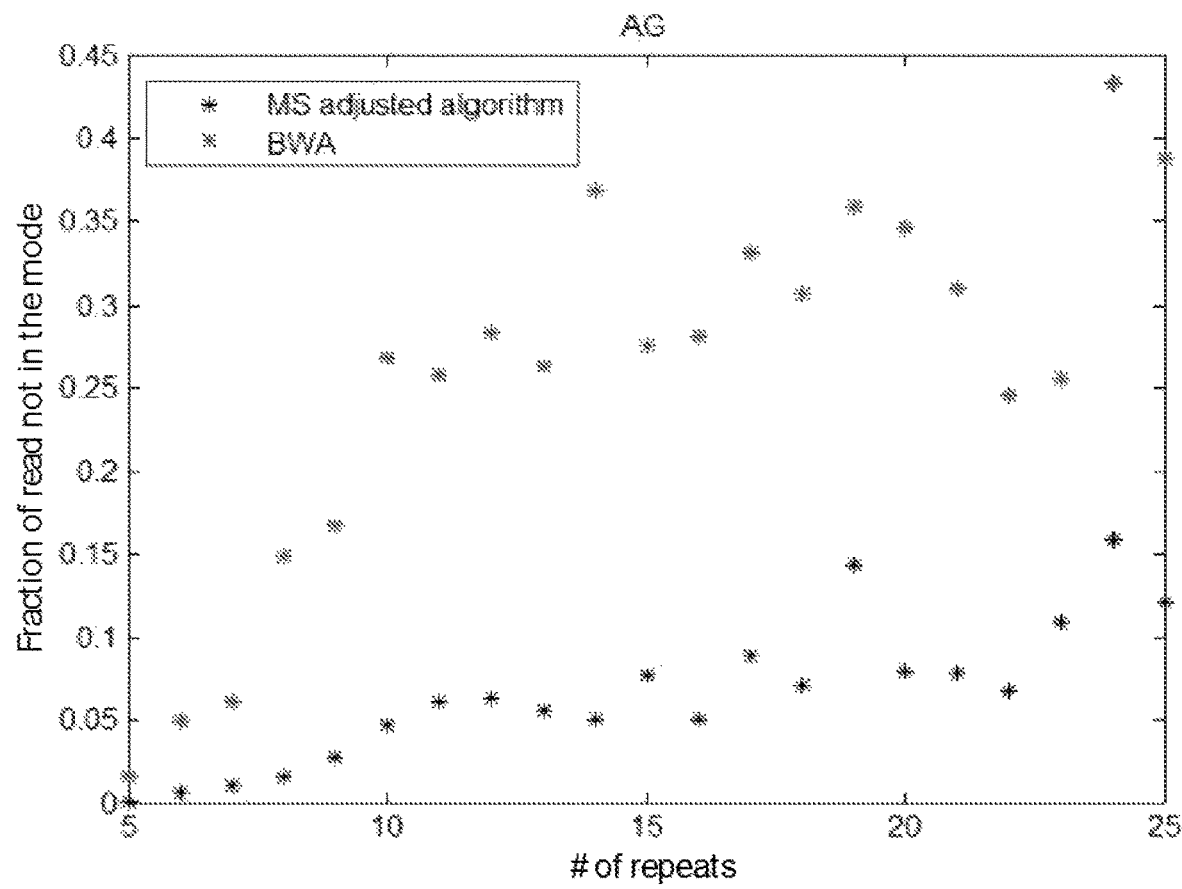
FIG. 8 is a dot plot showing an exemplary comparison of accuracy of sequence alignment tools at MS loci. Noise is plotted as a function of the MS repeat length for the standard alignment (BWA) versus the MS-specific alignment (adapted from lobSTR[2]). Data is shown for the AG motif. Noise was defined as the fraction of reads that differ from the modal number of repeats, aggregated over all the MS loci in the X-chromosome from normal male samples (which are assumed to be homozygous at each MS locus). On average, noise is reduced by approximately a factor of 5 using the MS-specific alignment method.

MS-specific alignment. For each normal and tumor sequencing file (ie. BAM file), the techniques herein used PHOBOS to identify all reads that contained a MS sequence. Following the approach applied in lobSTR[60], for each MS locus, the techniques herein used the 5' and 3' flanking sequences of the MS to identify reads that support the specific MS. The techniques herein considered all reads that had at least 10 bp flanking the 5' and 3' ends of the MS. (e.g., it was found that a minimum of 10 bp substantially reduces the number of reads that do not match the particular MS). The alignment procedure was performed in two steps. First, the techniques herein created, for each MS motif, a library of segments from the human reference genome (hg19) that contained 100 bases from the 5' and 3' ends of each MS locus. Then for each read that contains a MS sequence, the techniques herein aligned only the non-MS parts of the sequence to the library that contained loci corresponding to same motif that was found in the read (e.g. a read with 7 AGs was aligned against all MS loci with the AG motif). The second step of alignment was then performed using Bowtie2[61], and only reads that had a single best alignment were included in downstream analyses. MS-specific alignment decreased the number of incorrectly mapped reads by a factor of ~5 (FIG. 8).

Noise estimation. Using the MS-specific alignment, the techniques herein compiled the set of reads that map to each of the MS loci in every sample. For each MS locus, the techniques herein generated a histogram of MS repeat lengths (FIG. 1A). Without being bound by theory, it was hypothesized that not every length represented in the histogram reflects a true allele in the sample, as some lengths may be artifacts that were introduced by polymerase stuttering during PCR, sequencing process, or misalignment. In order to predict the true underlying alleles in the tumor and normal samples, the techniques herein generated an empirical noise model to estimate, $P_{\{j,m\}}^{Noise}(k, m)$, the probability of observing a read with a length of k repeats of motif m, given that the true allele in the sample has j repeats of m. Without being bound by theory, it was assumed that all MS loci with the same motif and the same number of repeats have the same noise distribution (and hence can be pooled together to improve the estimated noise model). In addition, it was also assumed that all normal samples from male donors have only one true allele at all MS loci on the X chromosome, and that the true number of motif repeats corresponds to the observed mode of repeat lengths (ie. the most common number of repeats), while other repeat lengths represent noise. Using this approach, the techniques herein generated an empirical noise distribution for MS loci with a specific motif and number of repeats. Finally, the techniques herein smoothed the noise model using python nonparametric regression function (polynomial of $3^{rd}$ order).

Allele calling. The techniques herein used the empirical noise model to infer the most likely allele(s) at each MS locus in every sample. The techniques herein began with the assumption that the sample had only one allele at a given MS locus, and found the most likely repeat length. In practice, it was found the repeat length that maximized the log likelihood, $$\ln(\mathcal{L}(A|r_i)) = \sum_{\{r_i\}} \ln(P_A^{Noise}(r_i))$$

where A is the underlying allele, e.g., the repeat length of motif m, $\{r_i\}$ represents the set of repeat lengths observed in the reads that mapped to the MS locus, and $P_A^{Noise}$ is the empirical noise model for the allele A.

Next, the techniques herein tested a model in which a sample harbors two distinct alleles at a MS locus present at a given ratio. These two alleles could be either germline (ie. inherited from the two parents) or could represent a somatic mutation at a homozygous site. The ratio between the alleles can be 1:1, as in a germline heterozygous site, or, in tumors, the ratio could vary depending on the number of copies of each allele, the purity of the tumor sample, and whether the mutation appears in all cancer cells or only in a subset of them. The techniques herein determined the likelihood for two alleles, $A_1$ and $A_2$, with fractions (f, 1-f); e.g. a read with 9 repeats of AC (r=9) and proposed alleles $\vec{A}=(A_1=6$ AC, $A_2=8$ AC, f=0.4). The contribution of read r to the likelihood function is then given by:

$$\ln(\mathcal{L}(\vec{A}|r)) = \ln(f \cdot P_{A_1}^{Noise}(r) + (1-f) \cdot P_{A_2}^{Noise}(r))$$

And based on all reads at the locus, the log likelihood is:

$$\ln(\mathcal{L}(\vec{A}|\vec{r})) = \sum_{\{r_i\}} \ln(\mathcal{L}(\vec{A}|r_i))$$

As previously, the allele set that had the maximum likelihood was chosen (by optimizing overt $A_1$, $A_2$ and f).

The techniques herein then compared the two models, the one-allele model and the two-allele model, using the log likelihood ratio test (using a $\chi^2$ null distribution), $P^{\chi^2}(D,\Delta f)$ <0.05 where $D = -2 \cdot \ln(\mathcal{L}_1) + 2 \cdot \ln(\mathcal{L}_2)$ and $\Delta f$ equals 2, as the techniques herein added two new parameters—the new allele and its fraction. If the $\chi^2$ test gave a p-value>0.05, the techniques herein chose the one-allele model. If the $\chi^2$ p-value<0.05, the techniques herein repeated the test comparing a two-allele model to a three-allele model, and so forth, until the techniques herein reached a maximum of four alleles. The techniques herein applied the following restrictions to this process: (1) analyzed only sites that had at least 10 reads covering them, and (2) called an allele only if there were at least 5 reads that support it.

Filtering normal loci. Even though normal samples should not have more than two alleles, the techniques herein allowed the algorithm to continue scanning for more than two alleles in normal samples as a test to detect MS loci associated with increased noise. The techniques herein did not call somatic MS indels at sites where the normal samples appeared to have >2 alleles or if the read counts were not consistent with a heterozygous site (i.e., binomial test p-value<0.05 with parameter of 0.5).

Mutation calling. For each tumor/normal pair, after inferring the alleles at each MS locus in each sample separately, the techniques herein compared the inferred alleles in the tumor and normal samples. MS loci that had different alleles in the tumor and normal samples were considered as potentially having somatic mutations and were nominated for downstream analysis. To ensure that alleles are indeed different, the techniques herein tested whether the tumor data is described by the tumor alleles better than the normal alleles, and vice versa. This was performed by comparing the Akaike information criterion (AIC) score for the two models and requiring that the difference exceeds a pre-defined threshold, $T_r$ (this was one of the parameters that were later optimized based on the simulated data):

$AIC^{Tumor\ model}(Tumor\ data) - AIC^{Normal\ model}(Tumor\ data) > T_r$ $AIC^{Normal\ model}(Normal\ data) - AIC^{Tumor\ model}(Normal\ data) > T_r$ Finally, as an additional filter, the techniques herein performed a Kolmogorov-Smimov (KS) test between the tumor and normal repeat length histograms. The KS test can identify sites with different alleles but does not identify the exact alleles in the tumor and normal. The KS test p-value was used as another filtering criteria (optimized using the simulated data).

False positive analysis. The false positive (FP) rate was estimated by analyzing three independent whole exome sequencing data sets from sample NA12878 from the 1000 Genomes project NA12878_47, NA12878_49 and NA12878_51. All three of these samples were sequenced at the Broad Institute, each based on a different WES library (to capture the variability introduced by library construction as well as by sequencing). From these three files, the techniques herein created six tumor-normal pairs by selecting one to represent the tumor and a different one to represent the normal. Note that MSMuTect is not symmetric with respect to the tumor and normal (hence the 6 possible pairs) since the tumor can have more than 2 alleles with different allelic ratios whereas the normal is allowed at most two alleles that are consistent with a 1:1 ratio.

Figure 9:
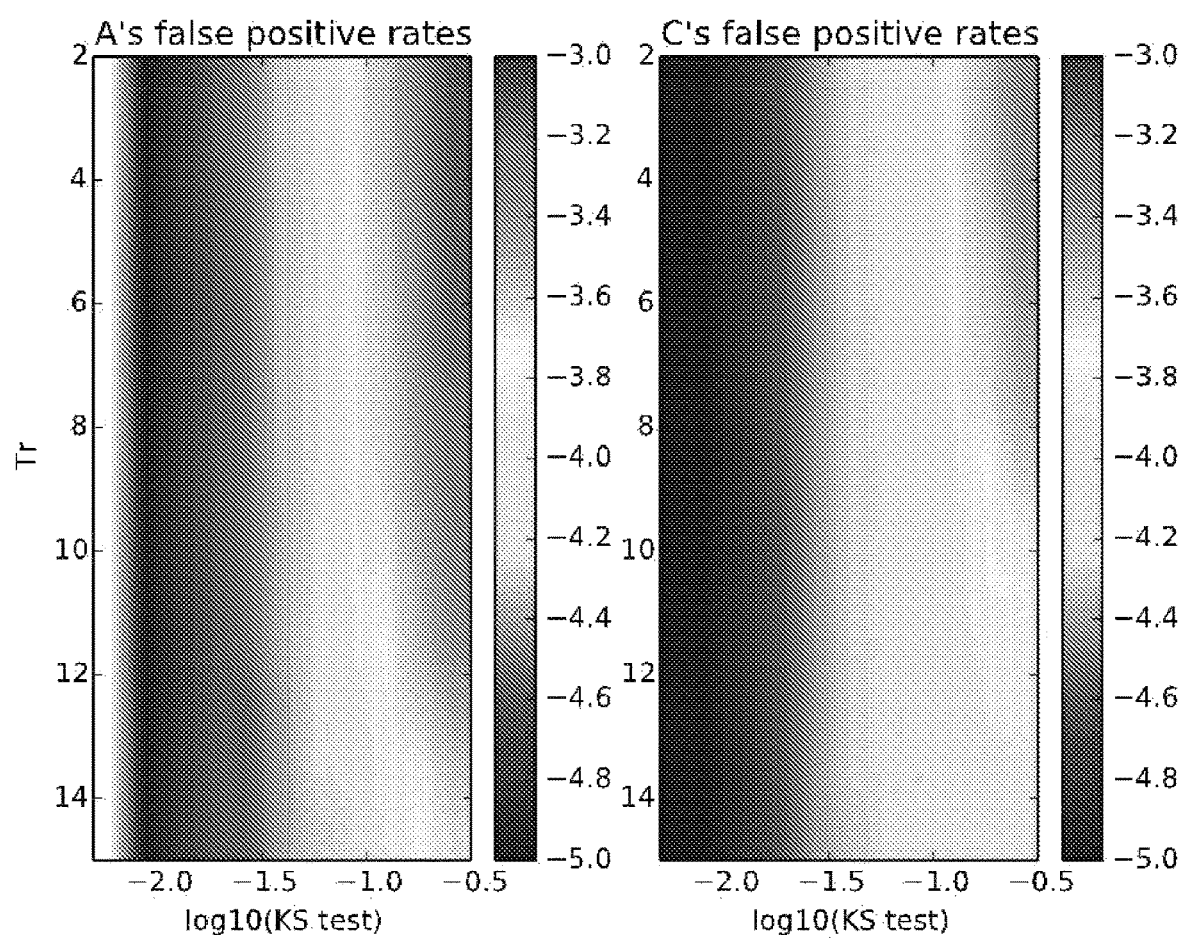
FIG. 9 depicts heat maps showing false positive rates for the A and C motifs as a function MSMuTect parameters. Heat maps show the $\log_{10}$ false positive rate per MS locus (i.e. the fraction of false-called MS indels among all MS loci) for the A and C motifs. The y-axis is the threshold for the different AIC scores ($T_r$) and the x-axis is the threshold for the Kolmogorov-Smirnov (KS) filtering step.

The techniques herein used MSMuTect to call somatic MS indels and found that the FP rates of the A motif and the C motif are similar across the range of $T_r$ and KS parameters (FIG. 9). The AC and AG motifs had only ~2000 loci, and the analysis did not yield any FP mutations for either of these motifs. Therefore, the techniques herein could not independently estimate the FP rates, but the techniques herein assumed them to be similar to the FP rates of the A and C motifs and therefore used the same parameter values for all motifs. The techniques herein chose parameters such that the FP rates for the different motifs resulted in an average of ~5 false positive MS indels across the entire exome, consistent with the FP cutoff used in MuTect[62]. To achieve this, the techniques herein chose values of AIC Tr=8 and KS-test=0.031 for all the motifs.

True positive analysis. To test the sensitivity of MSMuTect, the techniques herein created virtual tumor datasets using the same three WES datasets from sample NA12878 (NA12878_47, NA12878_49 and NA12878_51). Here, NA12878_47 was defined as the normal sample and NA12878_49 as the tumor sample and simulated MS indels using data from NA12878_51.

The techniques herein generated somatic MS indels by replacing a fraction fr of read lengths in a histogram representing a site with k repeats with read lengths from a site with l repeats, thus representing a somatic event from k to k,l at (1−fr,fr). The techniques herein evaluated MSMuTect using different values of fr (ranging from 0.05 to 0.5 with steps of 0.05) and generated 200 mutations for each allele (k), mutated at random, to alleles l=k±1.

RNA Validation. For the list of the 7 significant MS loci, the techniques herein manually compared the 161 MS indels found in the stomach cancer (STAD) cohort to the corresponding tumor RNA-seq data which was obtained from the Broad Institute's Genome Data Analysis Center (GDAC; see for example the World Wide Web at (www)gdac.broadinstitute.org/). An indel was confirmed if at least two RNA-seq reads supported the mutant MS allele (Supplementary Table S3).

MSI and POLE classification. For each sample, a score associated with POLE mutations and a score associated with MSI mutations were calculated based on the ratio of signal mutations (i.e., mutations uniquely associated with mutational process) to background mutations (other mutations). For POLE, the signal mutation[63] is C>A in the context TCT, and the background mutations are all other C>A mutations. The other common POLE-associated mutation—C>T in the context TCG—was not used as a signal mutation because it is also present in other common mutational processes, including the signature associated with spontaneous cytosine deamination at meCpG dinucleotides (sometimes called the "aging" signature), and APOBEC-associated signatures[63]. For MSI, a set of three signal mutations were chosen: C(C>A)N, G(C>T)N, and Y(A>G)N (where Y is a pyrimidine and N is any base) based on previous analyses[23], and all other mutations were considered background mutations. Finally, the techniques herein applied a sigmoid function to the ratio of these mutation counts to produce a final score value between 0 and 1.

Cancer genes. The techniques herein used a list of 727 widely accepted cancer genes recently published by Nik-Zainal et. al,[6] (see Supplementary Table 12 therein), which combined genes from the Cancer Gene Census (CGC)[64] list with gene lists from other accepted sources and recent publications.

Diversity in normal samples. As part of MSMuTect, the techniques herein identify the MS alleles in the normal samples before comparing them to tumor alleles. For each MS locus, the techniques herein analyzed the alleles across all normal samples and calculated its diversity, e.g., the fraction of normal samples that had an allele that is different from the reference genome. For the significance analysis (both for MSMutSig and the search for new events in known cancer genes), the techniques herein excluded loci that had >10% diversity.

While this is similar to the rationale for using a panel-of-normals comparison to exclude sites with either missed germline events or sequencing artifacts[62], in MS loci, this approach may also identify sites that are more prone to MS indels and have a naturally higher mutation rate.

Figure 6:
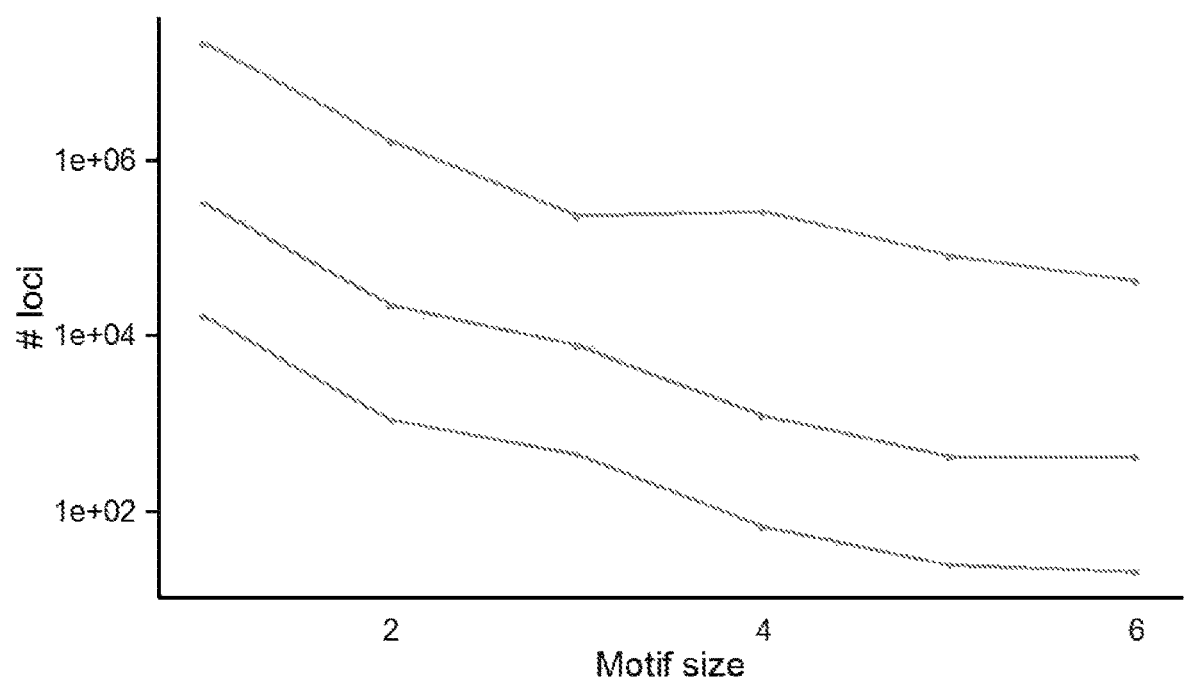
FIG. 6 is a graph showing the number of MS loci per motif size across the whole genome (red), exome (green), and in an annotated set of cancer genes from Lawrence et at[1] (blue). Mono- and di-repeats represent ~99% of all MS loci.
Figure 7:
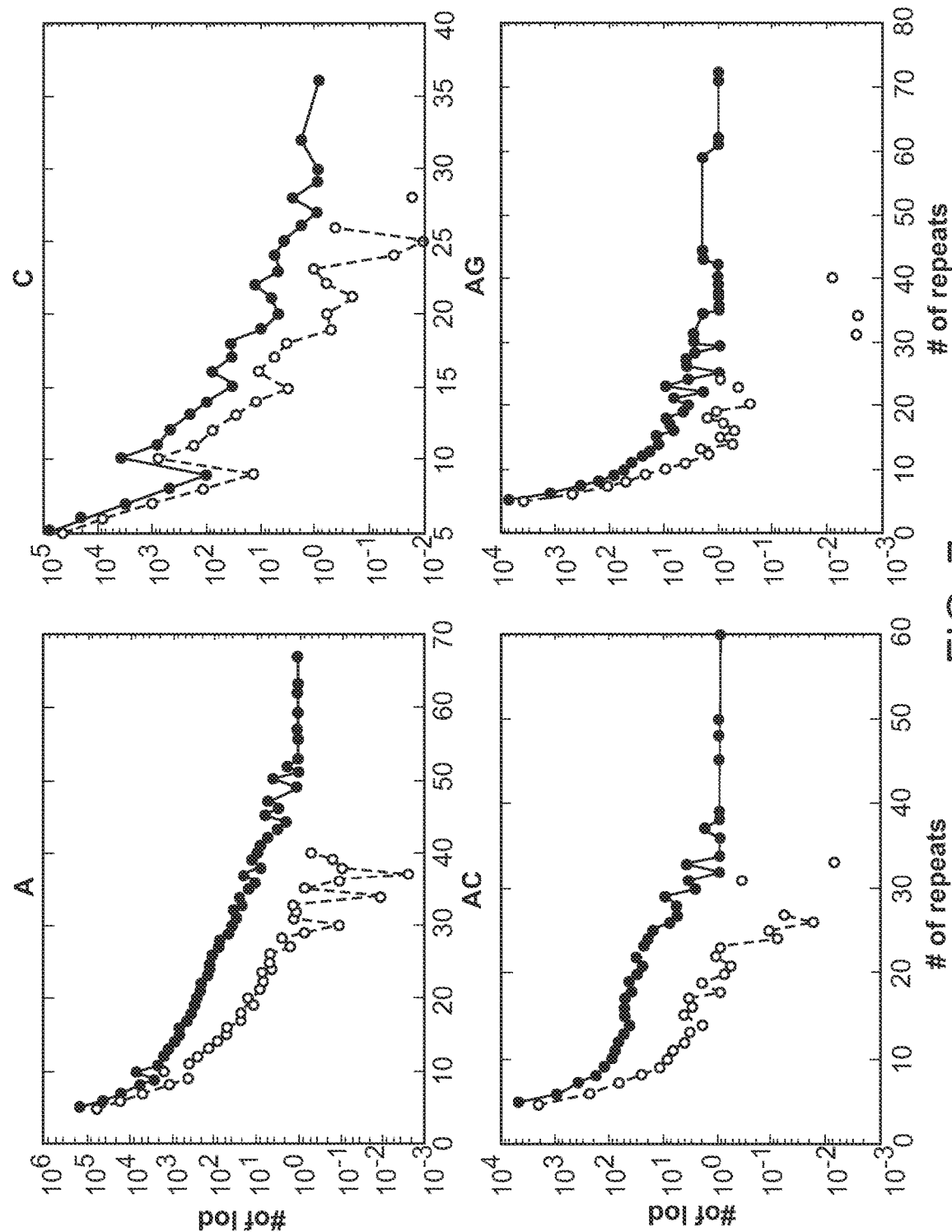
FIG. 7 depicts four graphs showing the results of sequencing coverage across motifs. The number of MS loci per length for different motifs (A, C, AC, and AG) across the exome is shown in red while the average number of MS loci covered by at least 10 reads is shown in blue. The number of MS loci covered at 10× depth decreases more rapidly than the number of MS loci, demonstrating the difficulty in achieving sufficient coverage for longer repeat lengths. Together, the motifs A, C, AC, and AG represent 98% of MS loci in the exome.
Figure 19:
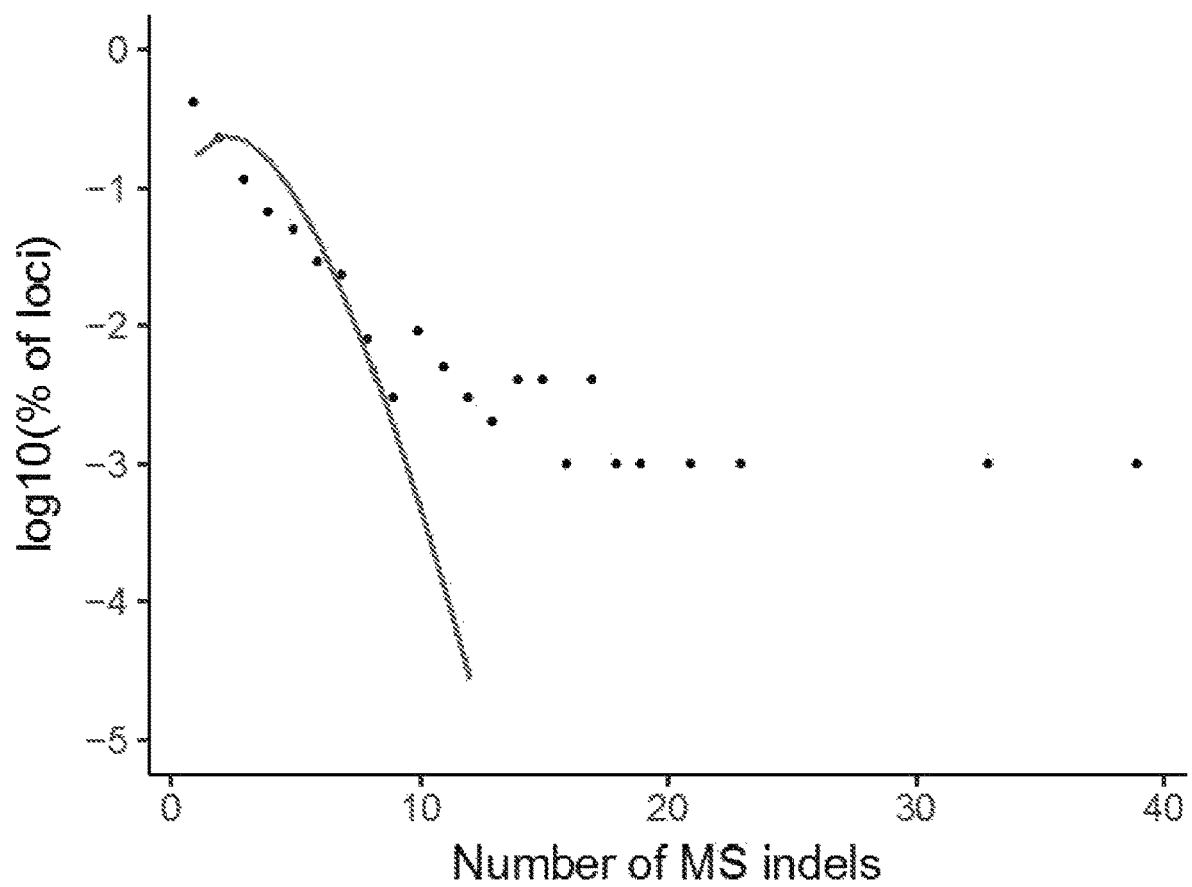
FIG. 19 is a graph showing the distribution of MS indels in $A_8$ in non-coding regions. The observed frequency of mutated $A_8$ loci per given number of indels are shown as black dots whereas the expected frequency using a fit based on a Binomial distribution is represented by the red line. The x-axis represents the number of MS indels and the y-axis represents the fraction of loci that have a particular number of MS indels.

MSMutSig. MSMutSig searches for MS loci that are mutated significantly more frequently than expected by chance. The techniques herein found that the main two covariates that influence the mutation rate at MS loci are the specific motif and the number of repeats (FIGS. 3B-C), while other covariates that are known to influence SNV rates (such as replication timing) have minimal effect on MS mutation rates. Thus, the techniques herein estimated the background mutation frequency for each motif and repeat length in every tumor type separately. The techniques herein estimated the rates (and tested the significance) of loci that contained at least one MS mutation across the analyzed cohort. These conditional rates (ie. conditional on observing at least one event) were calculated since a wide variability of mutation rates with a significant enrichment of sites with no mutation was observed. Estimating the mutation rate including these "stable" sites will underestimate the overall background rate and hence inflate the list of significantly mutated loci. As an example, for the A motif with 11 repeats, there were 208/242 loci without any MS indel across the COAD MSI-H cohort, which is ~6 times more than the techniques herein would have expected (35 loci, P-value<$10^{-16}$ Binomial test,) when using all sites and events to estimate the background rate. Therefore, it was concluded that there is a subset of MS loci that are less prone to MS indels and should be excluded from the estimation. Even after excluding these "stable" sites, there was still a large variability of mutation rates among MS loci with the same motif and repeat length, beyond the variability one would expect from a binomial distribution assuming all sites had the same underlying background mutation rate. This high variability was observed even among loci that reside in genomic regions that are less likely to harbor functionally relevant MS loci than exons, such as UTR's and introns (FIG. 19). Therefore, the techniques herein included an additional variable to attempt to capture this increased variability. A negative-binomial distribution (also known as the gamma-Poisson), which has two parameters that control the mean and the variability around the mean, was used. The techniques herein set the mean to reflect the average mutation rate (at sites with at least one MS indel), and then tuned the variability such that no significant loci were identified outside the exome (with FDR q<0.1). The techniques herein then used these parameters to identify significantly mutated MS loci in the coding regions. The Q-Q plots for the non-coding MS loci and coding MS loci are shown in FIGS. 6-8 (for different tumor types). One can see that there is no inflation of significantly mutated sites and most MS loci follow the expected uniform p-value distribution (ie. reside close to the diagonal of the Q-Q plot).

Expression data. The RNAseq based normalized expression level for each gene was obtained from the Broad Institute's Genome Data Analysis Center website ((www) gdac.broadinstitute.org/). The techniques herein used the $\log_2$-normalized RSEM values when available, but in cases where they were not available, $\log_2$ RPKM values were used.

MSMuTect: A tool to identify MS indels from exome sequencing data. In an effort to improve detection of somatic MS indels, the techniques herein globally re-aligned reads[7] from 6,747 tumor/normal pairs across 20 tumor types from The Cancer Genome Atlas (TCGA) to a reference sequence in an attempt to identify all MSs with at least five repeats of a 1-6 base motif, allowing up to 15% impurity (FIG. 7 for loci distribution)[1]. This re-alignment step identified 383,515 MS loci in regions covered by TCGA whole exome Illumina data and reduced the fraction of misaligned reads compared to standard alignment (FIG. 8). Next, for each sequencing read spanning a MS locus, the techniques herein used the 5' and 3' flanking parts of the read to align it to the reference sequence (using PHOBOS[16]). The techniques herein then counted the number of reads that supported each MS repeat length, thus producing two histograms of MS repeat lengths per locus, one for the tumor and one for the matched normal sample (FIG. 1A).

Sequencing errors, PCR amplification errors, and other sources of noise can increase or decrease the number of MS repeats present in a given read. Therefore, the observed numbers of MS repeats in a read that aligns to a specific MS locus fluctuate around the true value (or values, in the case of a heterozygous site). Therefore, the true underlying allele(s) must be statistically inferred from the data (FIG. 1B). Critical to this inference is the empirical estimation of the noise associated with each type of MS (i.e., the probability of observing a read with i repeats of a particular motif if the true number of repeats is j). The techniques herein trained empirical noise models, one for each MS type (defined by its motif and number of repeats), using data from homozygous sites derived from the X chromosome of 4,411 male normal samples (i.e., having only one true allele at each MS locus). The techniques herein had sufficient data to reliably estimate the noise models for the motifs A, C, AC, and AG, which together represent 98% of the MS loci in the exome (FIG. 7).

In order to accurately identify the alleles present in tumor and normal samples and detect somatic MS indels (i.e., sites at which tumor and normal alleles differ), the techniques herein used these noise models to calculate, for each MS locus, the set of most likely alleles for the tumor and normal samples (FIG. 1C). For each locus, the techniques herein used a log likelihood ratio test to compare models in which the locus harbored one versus two distinct alleles (either distinct germline alleles or a somatic mutation at a homozygous site). If the two-allele model fit the data better, the techniques herein then compared it to a three-allele model, and so forth, to a maximum of four alleles. Finally, to ensure that the tumor and normal alleles were indeed different, the techniques herein nominated somatic MS indel events only when the histogram of MS repeat lengths in the tumor was described better by the tumor alleles than by the normal alleles (FIG. 1C).

The techniques herein tested the sensitivity and specificity of MSMuTect using an approach similar to that previously described for MuTect[17]. To estimate the false positive rate (i.e., 1-specificity), the techniques herein used three independent sets of exome data from the 1000 Genome project sample NA12878[18] (each with an average depth of 60×), and applied MSMuTect to all six possible assignments of these replicates to 'tumor' and 'normal'. Since all data were acquired from the same sample, all putative somatic MS indels identified by MSMuTect are false positives. The techniques herein ran MSMuTect across a range of parameter settings and estimated the false positive rate by calculating the average number of apparent somatic MS indels nominated across the six pair-wise comparisons (FIG. 9). For each of the MS motifs (e.g. A, AC, etc.), the techniques herein chose parameter values that, on average, generated no greater than five false positives per exome.

Figure 10:
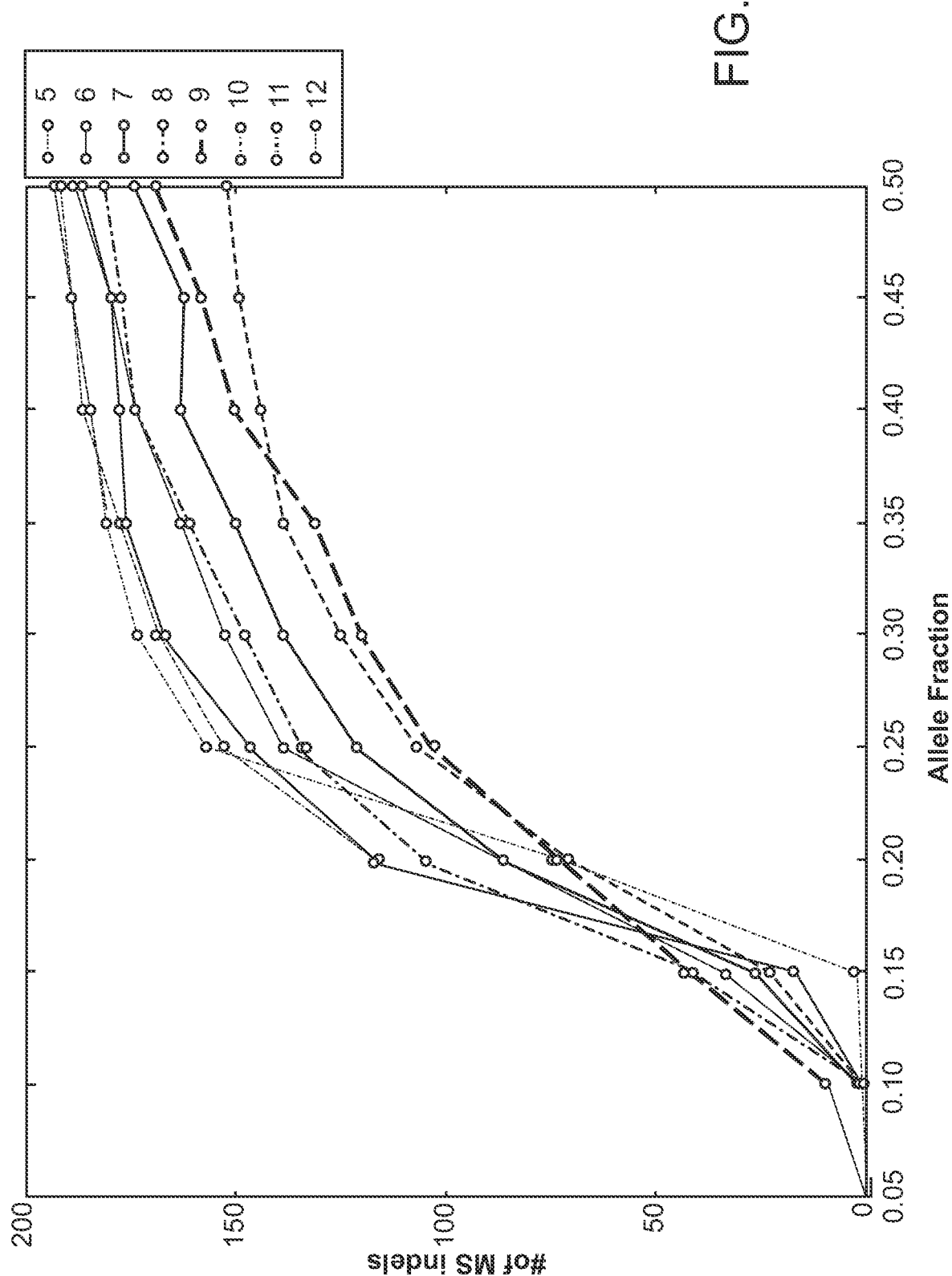
FIG. 10 is a graph showing analysis of true positive rates. The number of detected simulated MS indels (out of 200) across repeat lengths (shown in different colors) and allele fractions. The sensitivity to detect MS indels decreases markedly at low allele fractions.
Figure 11:
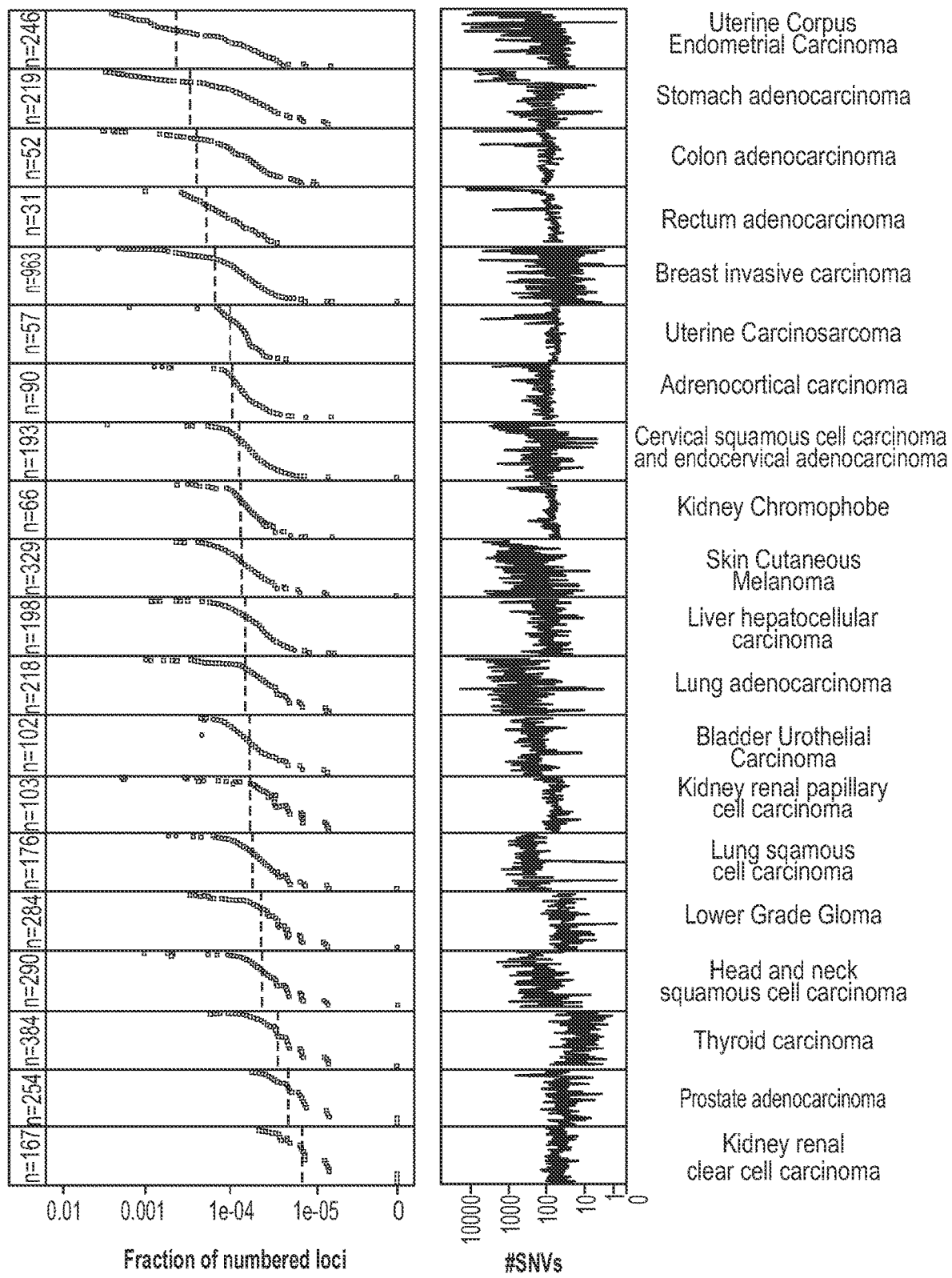
FIG. 11 shows a comparison with the SNV distributions for each tumor type.

To evaluate sensitivity, the techniques herein simulated 20,000 somatic MS indels by inserting or deleting a single motif repeat at different loci throughout the exome and then measured the ability of MSMuTect to detect these changes as a function of the original number of motif repeats and the variant allele fraction. To capture the noise present in real NGS data, the techniques herein simulated a somatic MS indel by replacing reads from a given locus with reads of a different length of the same motif taken from a different copy of NA12878. The number of replaced reads reflected the desired allele fraction of the event. The techniques herein inserted or deleted a single motif since these are the most prevalent MS indel events in the genome and are also the most challenging to detect. The techniques herein then used MSMuTect to detect somatic mutations by comparing the simulated tumor to the third copy of NA12878 (acting as the matched normal). The techniques herein evaluated the sensitivity of MSMuTect to identify MS indels for various allele fractions and repeat lengths (FIG. 10). Sensitivity was highest for shorter MS loci (e.g. sensitivity decreased from 98% for AAAAA, or $A_5$ in short, to 75% for $A_{12}$) (FIG. 10). Simulated MS indels with an allele frequency below 20% exhibited high rates of false negatives, likely because the allele fraction of 'artificial' MS indels generated by PCR exceeded the simulated MS indel fraction.

Figure 2:
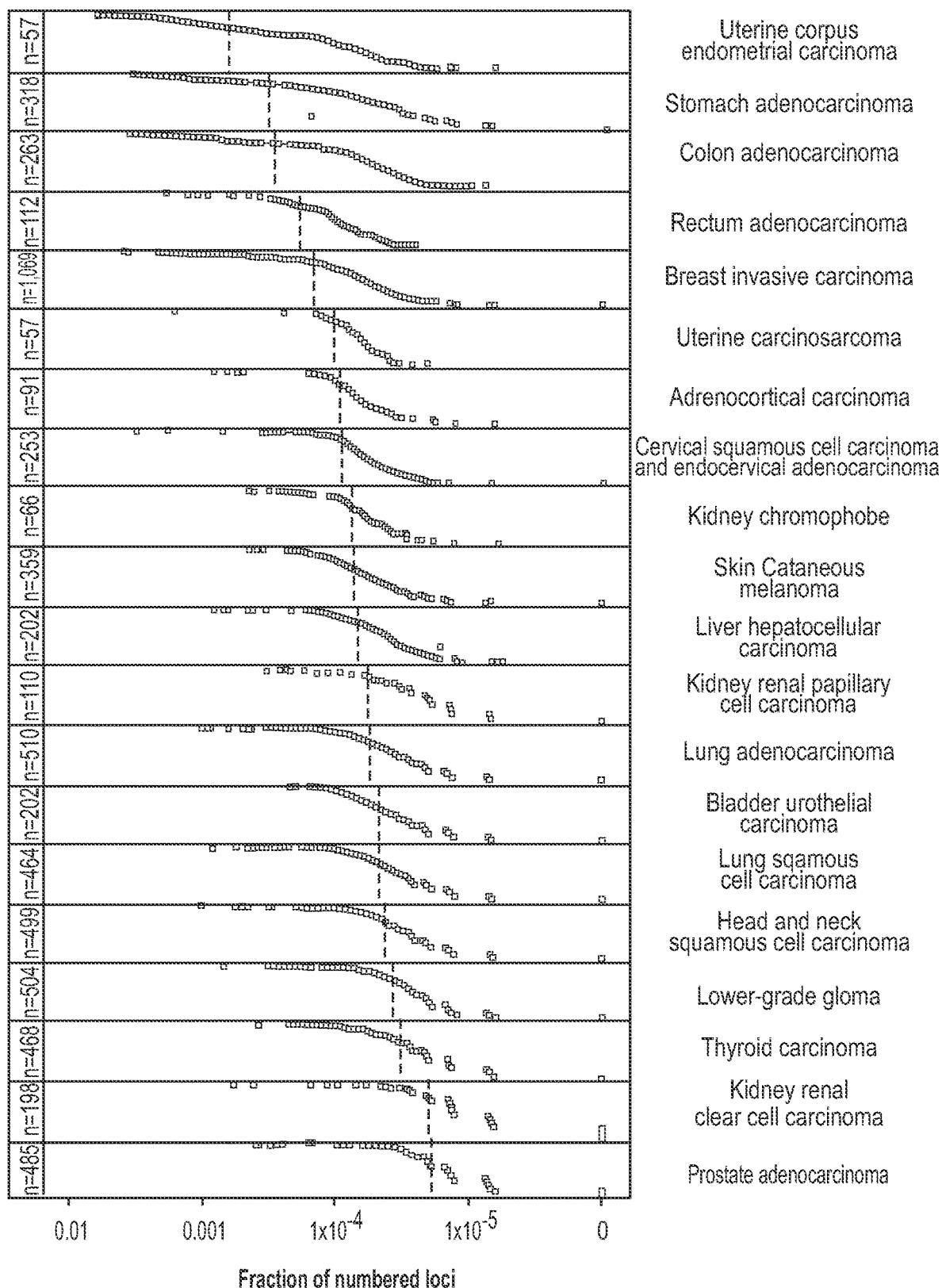
FIG. 2 depicts graphs showing the distribution of MS indels across 6,747 tumors from tumor types. Red horizontal lines represent the median fraction of MS indels in each tumor type.

MS indel mutational landscape. To characterize the landscape of MS indels across cancer, the techniques herein applied MSMuTect across 6,747 TCGA whole exome tumor/normal pairs representing 20 tumor types (Supplementary Tables S1 and S2). The analysis identified 174,638 MS indels, with a range of 0 to 900 per tumor. The techniques herein observed extensive inter- and intra-tumor variability in the MS indel rate, similar to the variability reported for single nucleotide variations and copy-number alterations (FIG. 2)[15]. The average MS indel frequency varied significantly across tumor types, with the highest frequencies in colorectal (COAD, READ), stomach (STAD) and endometrial tumors (UCEC), consistent with frequent loss of MMR pathway function and the associated MSI phenotype observed in these tumors.

Breast cancer (BRCA) had the fifth highest MS indel rate, and while BRCA is not typically thought to have high rates of MS indels, there is a small subset of BRCAs with known MSI features[19], and a recent[6] analysis of 560 breast cancer whole genomes indeed identified mutational signatures consistent with loss of mismatch repair in a subset of breast cancers. Interestingly, the recent report by Hause et al[13] did not identify MSI-H cases in breast cancer. However, they analyzed only a subset of the TCGA BRCA cohort (266/1069 cases), which included only 3 of the 36 tumors for which the techniques herein found >100 MS indels. Previous reports[20,21,22] identified a small fraction of MSI cases in cervical squamous cell carcinoma and endocervical adenocarcinoma (CESC), uterine carcinosarcoma (UCS) and adrenocortical carcinoma (ACC). Consistently, the techniques herein identified a high number of MS indels in these tumor types (ranked $6^{th}$, $7^{th}$ and $8^{th}$ in MS indel frequency, respectively).

To validate the MS indels identified by MSMuTect, the techniques herein analyzed RNA-seq data that was available for a subset of the tumor samples (Supplementary Table S3). For each of the 150 significantly mutated MS indels (described below) with sufficient RNA-seq coverage (≥4 reads), the techniques herein manually compared the alleles inferred by MSMuTect to the alleles observed in the RNA-seq data. RNA-seq and exome sequence calls were concordant in 87% of cases (131/150 had at least 2 RNA-seq reads that supported the mutant allele; Supplementary Table S3). Importantly, RNA-seq underestimates the accuracy of MSMuTect because MS indels that introduce premature stop codons can trigger nonsense-mediated decay of the faulty mRNA transcript, thus decreasing the likelihood of observing RNA-seq reads that support the MS indel. Indeed, MS loci closer to the 3' end of the transcript, which are less likely to trigger nonsense-mediated decay, had higher validation rates (e.g. ACVR2A (96%) and RNF43 (100%); Supplementary Table S3). For four of the five cases in which two distinct somatic events were identified at the same site (e.g. the normal had 10 repeats and the tumor had 9 and 8 repeats), the techniques herein were able to validate all three alleles (one wild type allele and two alternate alleles) in the RNA-seq data (Supplementary Table S3).

MSMuTect correctly classifies tumors with respect to MS stability. To further characterize the ability of MSMuTect to identify microsatellite features in tumors, the techniques herein turned their attention to tumor types that display wide variation in microsatellite stability and asked whether MSMuTect could recapitulate independent measures of MS stability in these tumors. As part of the TCGA project, tumors from the colon adenocarcinoma (COAD), stomach adenocarcinoma (STAD), and uterine corpus endometrial carcinoma (UCEC) cohorts were experimentally classified as exhibiting microsatellite stability (MSS, no indels) or microsatellite instability (MSI-low [MSI-L], indel at one MS locus; MSI-high [MSI-H], indels at 2 or more MS loci) using a PCR-based assay to assess size variability at the five Bethesda microsatellite (MS) loci[12].

Figure 3A:
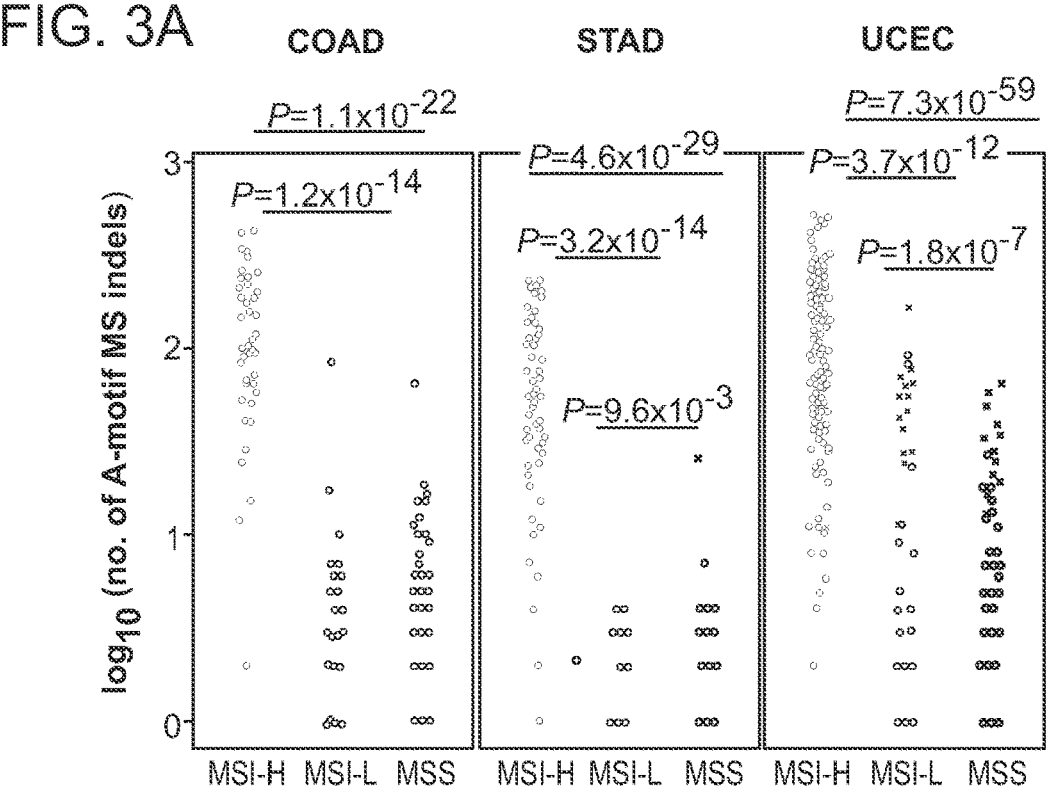
FIGS. 3A-3D show graphs and bar charts depicting the differences in mutation patterns and MS indel characteristics between microsatellite unstable (MSI) and microsatellite stable (MSS) tumors.
Figure 12:
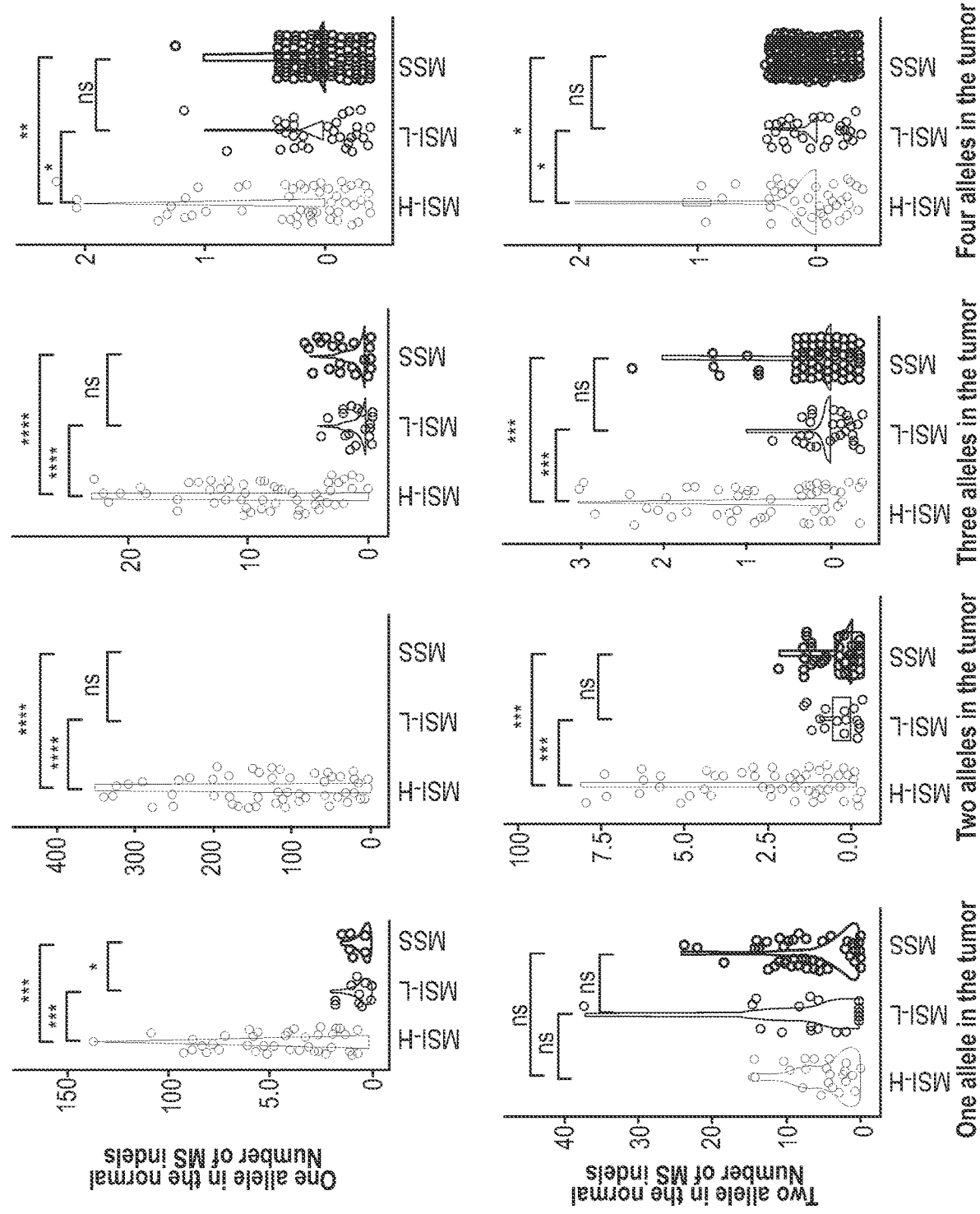
FIG. 12 shows eight dot plots depicting the number of MS indels for STAD samples (broken to MSI-H, MSI-L and MSS) plotted for different numbers of germline and tumor alleles. MSMuTect not only detects the presence of a somatic MS indel, but also infers the actual alleles in both the germline and tumor samples. The upper row shows the number of MS indels for loci that had one allele in the germline and the lower row for two alleles in the germline. The columns represent that number of somatic MS indels alleles in the tumor (range from one to four.) For example, the plot in the third column of the second row shows cases in which the germline has two alleles (e.g., heterozygous sites) but the tumor sample has 3 alleles. MS indels are more common in MSI-H tumors in all settings except when the germline has two alleles but the tumor has only a single allele (bottom left corner), which reflects loss-of-heterozygosity (LOH). MSI designations (MSI-H, MSI-L, or MSS) are based on Bethesda gel classification (taken from TCGA). The y-axis scale varies across panels. The significance of the difference was calculated using t-test (ns-p>0.05, * p<0.05,  p<$10^{-3}$, * p<$10^{-8}$, **** p<$10^{-16}$)

The techniques herein used MSMuTect to detect and count the number of MS indels for tumors classified as MSI-H, MSI-L, and MSS by Bethesda criteria (FIG. 3A). Samples that were classified as MSI-H indeed had significantly more MS indels than samples that were MSS or MSI-L (MSI-H vs MSS: COAD median 104.5 vs. 3.0, $P<10^{-22}$; STAD 64.5 vs. 1.0, $P<10^{-28}$; UCEC 94.5 vs. 2.0, $P<10^{-58}$, Mann-Whitney). There was no difference in the number of MS indels in tumors classified as MSS versus MSI-L for COAD, but there was a small difference in UCEC and STAD (MSI-L vs. MSS: UCEC median 9 vs. 2, $P<10^{-6}$; STAD 3 vs 2, $P<10^{-3}$, Mann-Whitney) due to contribution from a small number of MSI-L cases with many MS indels (discussed below). In addition, the techniques herein found that MSI-H tumors were significantly more likely to have several MS indels at the same locus and also are more likely to have one (or more) MS indels at heterozygous MS sites (FIG. 12).

Although MSMuTect appears to separate the majority of MSI-H tumors from MSI-L and MSS tumors, there were several outlier cases with an apparent discrepancy between the MS indel count and the Bethesda designation (FIG. 3A). To further characterize these cases, the techniques herein applied a single nucleotide variation (SNV)-based approach. MMR-deficient tumors are known to have a specific pattern of SNVs (MSI-SNV signature), and thus the fraction of SNVs associated with the MSI-SNV signature can be used as an orthogonal metric to identify the MSI phenotype[23]. As expected, tumors in which MSI-SNVs comprised >15% of the total SNVs (red in FIG. 3A) were nearly all (264/277) classified as MSI-H and had high MS indel counts. However, the majority (7/12) of the MSI-H STAD and UCEC tumors with the lowest MS indel counts (<10) had an MSI-SNV fraction <15% (blue in FIG. 3A), suggesting that the samples may have been misclassified as MSI-H by the Bethesda markers.

In addition, the techniques herein observed that many of the MSI-L and MSS samples with the highest number of MS indels also had a relatively high number of total SNVs (FIG. 3A). Mutations in the exonuclease (proofreading) domain of polymerase epsilon (POLE) can dramatically increase the number of SNVs. To investigate the potential interaction of POLE-mediated mutagenesis with MS indels, the techniques herein calculated the fraction of SNVs that were likely contributed by POLE-mediated mutagenesis (POLE-SNVs). All but one of the 63 samples in which POLE-SNVs comprised >15% of the total SNVs had a somatic missense mutation in the exonuclease domain of POLE (n=60) or polymerase delta (POLD1; n=2). Although the majority of the POLE/POLD1-mutated tumors (45/63) were classified as MSS or MSI-L, they had significantly more MS indels than other MSS and MSI-L tumors (median 54 vs. 2 among MSI-L and 18.5 vs 2 among MSS), raising the possibility that POLE/POLD1 exonuclease domain mutations may contribute to the rate of MS indels and highlighting the limitations of the PCR-based MSI assay (FIG. 3A).

Qualitative differences between MS indels in MSS and MSI samples. MSI and MSS samples not only differ in the number of MS indels, but also in other genomic properties. In particular, the relationship between MS indel frequency and DNA replication timing differs between MSS and MSI tumors, and both are distinct from the association reported for SNVs[14,24]. In MSS samples, MS indels do not have a strong correlation with replication timing (slope=−0.03, Pearson correlation=−0.47, P=0.43, t-test; FIG. 3B), whereas in MSI samples, early replicating loci tend to have a higher density of MS indels compared to late replicating loci (slope=−0.1, Pearson correlation=−0.995, P=0.0003, t-test; FIG. 3B)[25]. The mechanism underlying this difference is unclear and requires further investigation.

Figure 3C:
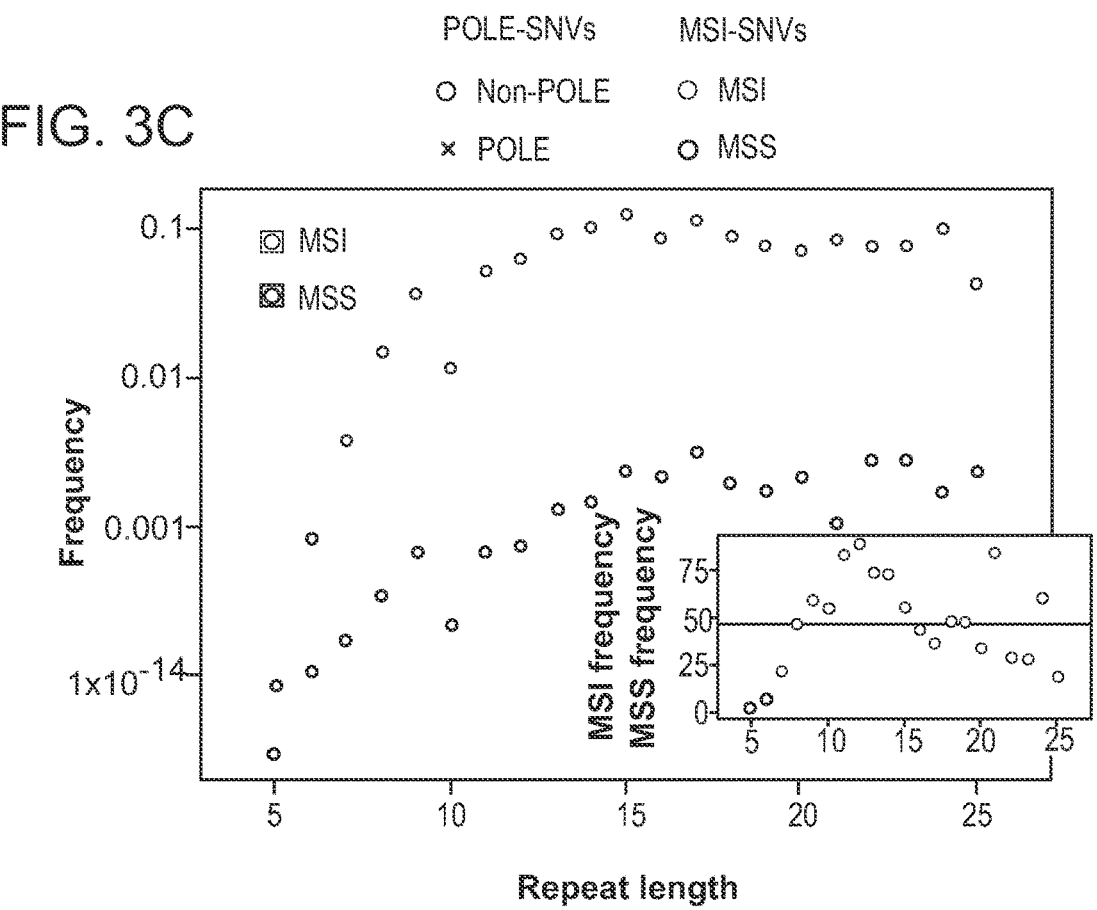
Figure 3B:
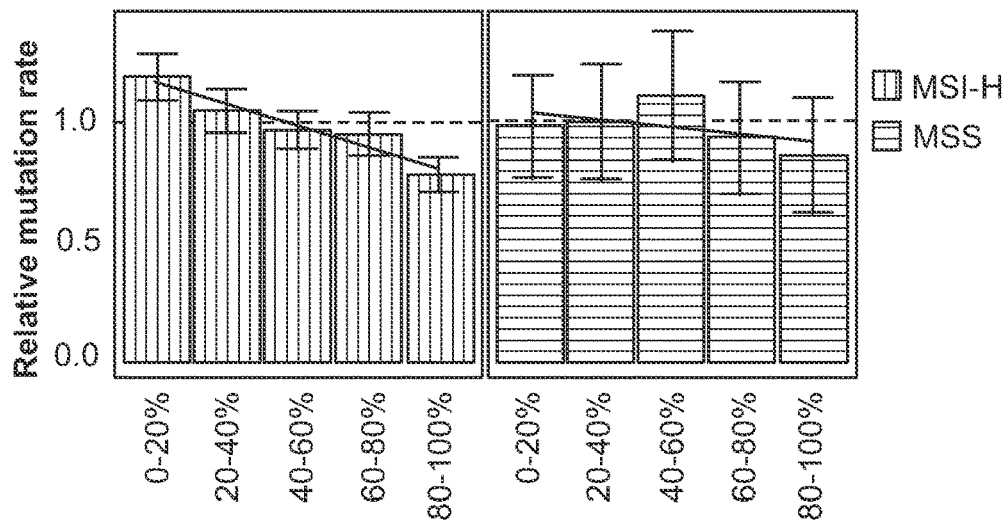

Likewise, in both MSI and MSS tumors, MS indels are more common at loci with longer repeat lengths; however, the slope and shape of these relationships differ between MSI and MSS tumors (FIG. 3C). Moreover, the ratio of insertions to deletions is different between MSS and MSI cases, with MSI cases having a tendency towards deletions[25], while MSS cases tend towards insertions (FIG. 3D; $P<10^{-31}$, $\chi^2$ test). The tendency to increase repeat lengths in MSS cases is consistent with germline MS indels, which have been shown to preferentially undergo insertions in MS loci with <15 repeats (the majority of the somatic MS loci analyzed here also have <15 repeats)[2].

Figure 13:
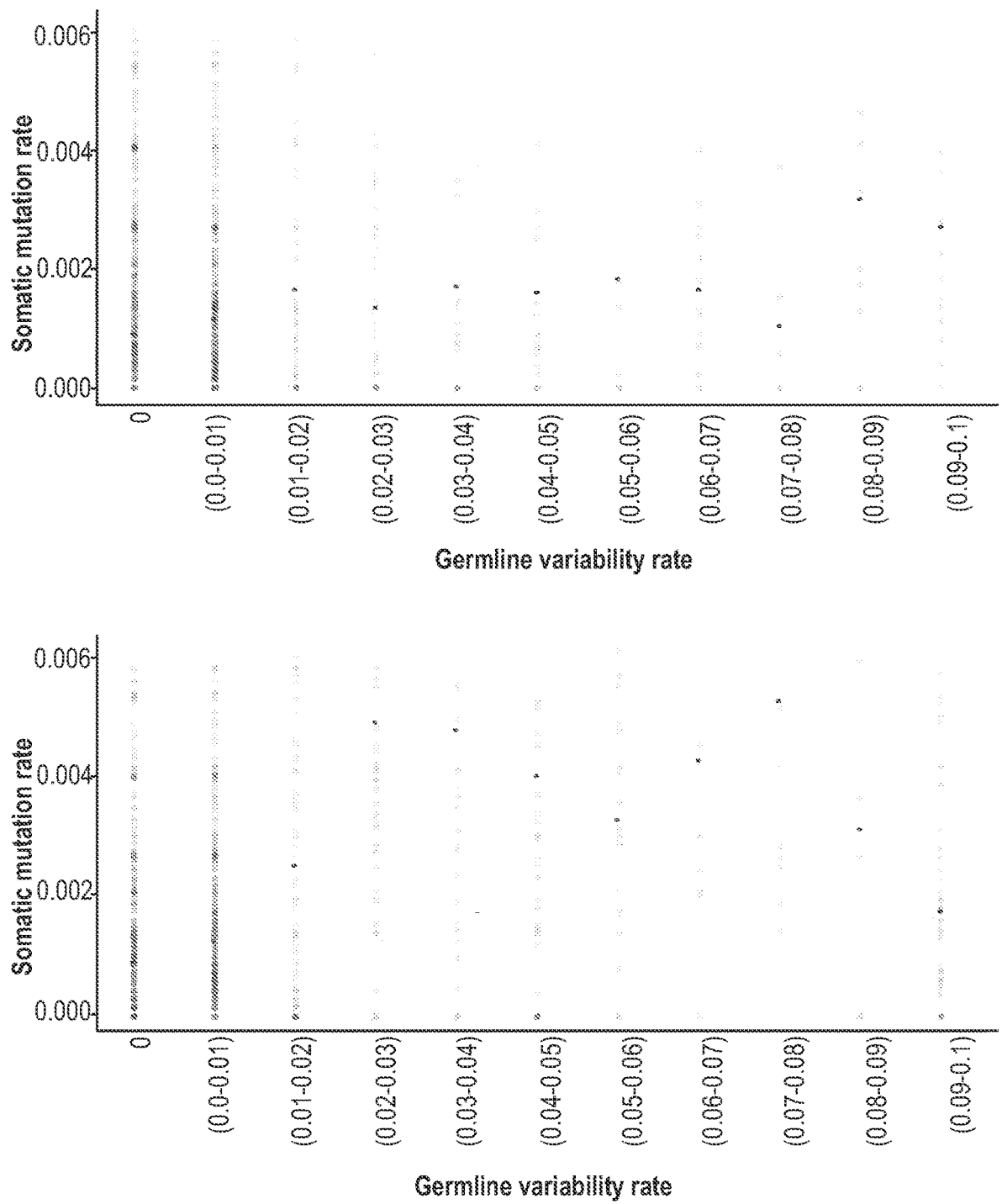
FIG. 13 shows two plots depicting the correlation between germline variability and somatic MS indel frequency. The x-axis represents the binned fraction of non-reference alleles at each MS locus (out of the 2*N alleles in the cohort, where N is the number of covered normal samples). The somatic MS indel frequency for each MS locus is plotted as blue dots. Black dots represent the mean of each bin. The upper panel shows germline variability of $A_8$ in the range of germline variability between 0 to 0.1 and the lower panel in the range of 0 to 1. The effect of germline variability on the somatic rate is minor for germline variability <0.1.

New MS indels in known cancer genes. The techniques herein next sought to identify somatic MS indels that drive tumorigenesis. The techniques herein first focused on novel MS indels in 727 known cancer genes[6] across a cohort of 4,064 TCGA samples with curated mutations calls (based on TCGA consortium publications). The techniques herein focused their analysis on MS loci for which at least 90% of the normal (germline) samples matched the reference allele (i.e. <10% diversity; FIG. 13), as loci with greater germline diversity may have an increased rate of false positive MS indel calls. The techniques herein detected 1470 MS indels across these genes (Supplementary Table S4), including 89 indels that had been previously identified by the TCGA consortium and 1105 indels in samples without any other indel or non-synonymous SNVs reported in the same gene (thus potentially representing novel loss-of-function events in these cancer genes). The remaining 276 indels were identified in samples that had a separate event (MS indel or nonsynonymous SNV) in the same gene; in these cases, the identified MS indel may represent the "second hit"[26] in these cancer genes. Across the entire cohort, the techniques herein were able to increase the fraction of cases in which a cancer gene harbors a single alteration (i.e., MS indel or non-synonymous SNV) by 2.3% and the fraction of cases with two alterations by 4.7% (within individual tumor types, these rates ranged from 0.5% to 5% for novel first alterations and from 0% to 27% for second alterations). In some genes, new MS indels comprise a substantial fraction of the total mutational events in the gene. For example, the techniques herein identified 15 novel MS indels in CTCF, a transcriptional repressor that was previously reported to have 45 non-synonymous mutations across 168 endometrial (UCEC) cases. Similarly, 27 non-synonymous mutations in NF1 had previously been reported among breast cancer (BRCA) cases, and the analysis yielded 16 additional MS indels. Overall, across the entire cohort, MS indels were enriched in tumor suppressor genes (TSGs)[27] compared to oncogenes (993 MS indels in 70 TSGs vs 272 MS indels in 53 oncogenes, $P<10^{-58}$, binomial test;).

Figure 14:
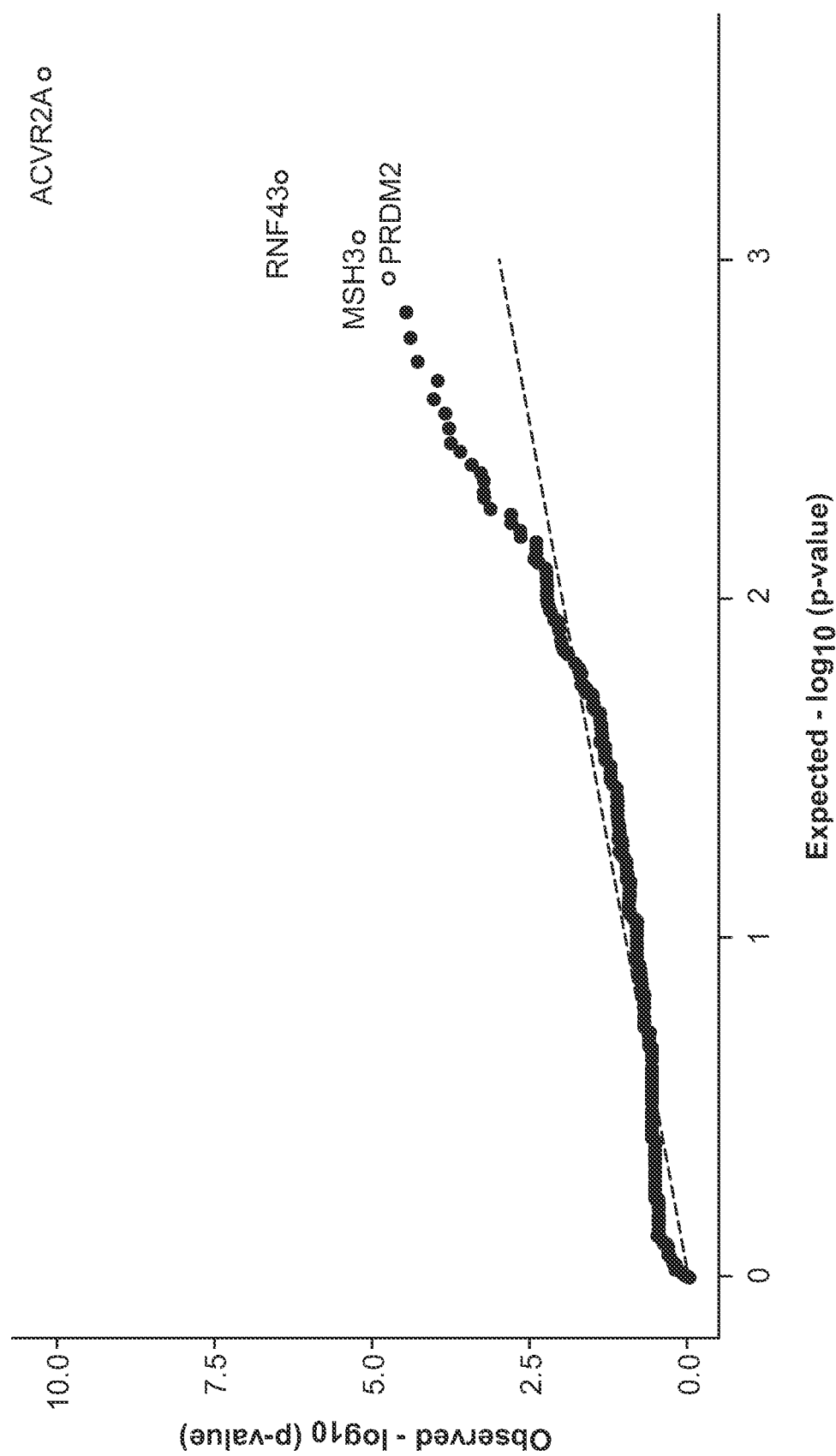
FIG. 14 shows a MSMutSig QQ plot for stomach adenocarcinoma (STAD). Quantile-quantile plot of observed vs. expected P-values under the negative binomial (also called gamma-Poisson) model. Significant MS loci (q<0.1) are shown in red.
Figure 15:
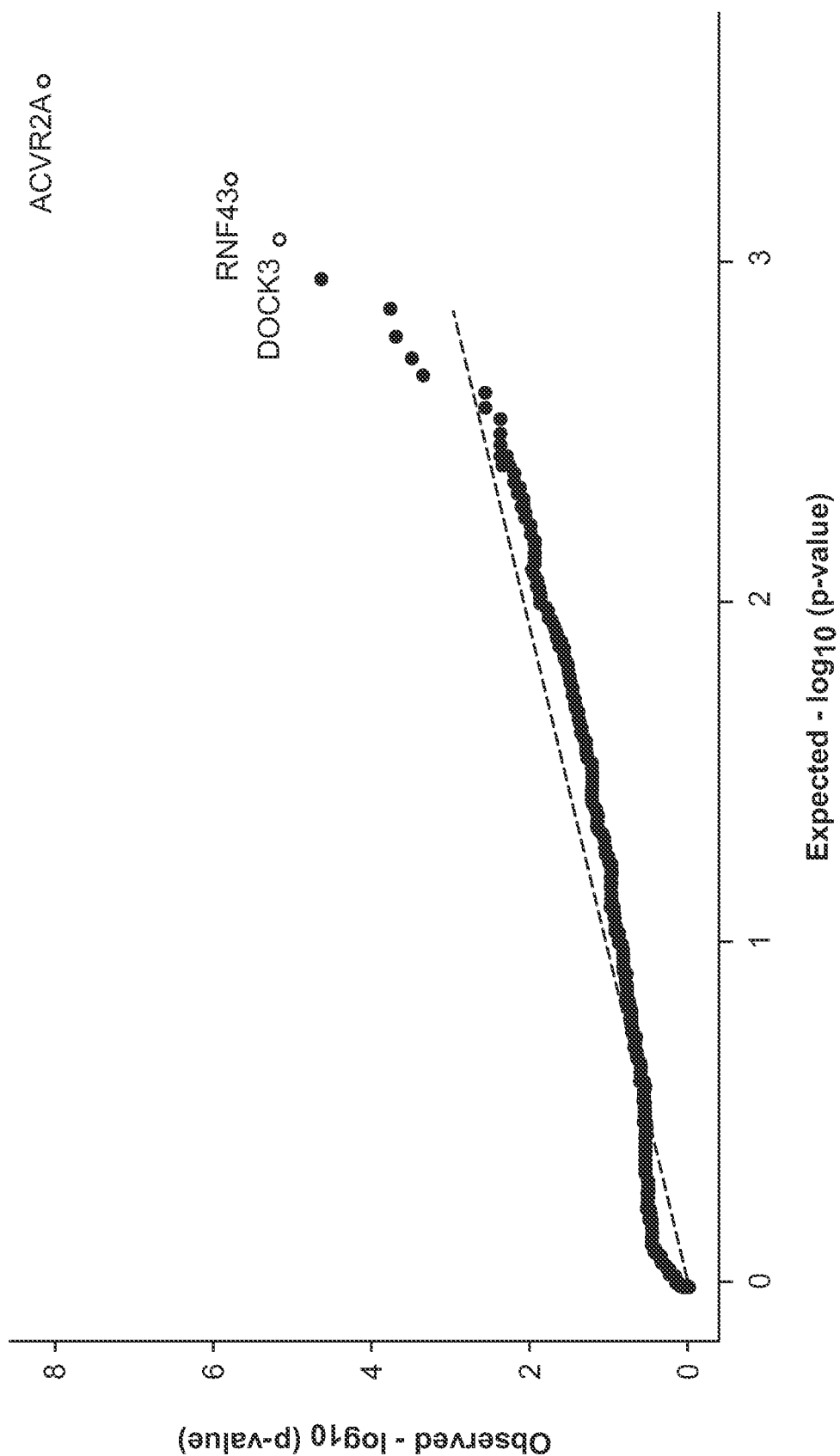
FIG. 15 is a graph showing an exemplary MSMutSig QQ plot for colon adenocarcinoma (COAD). Quantile-quantile plot of observed vs. expected P-values under the negative binomial (also called gamma-Poisson) model. Significant MS loci (q<0.1) are shown in red.
Figure 16:
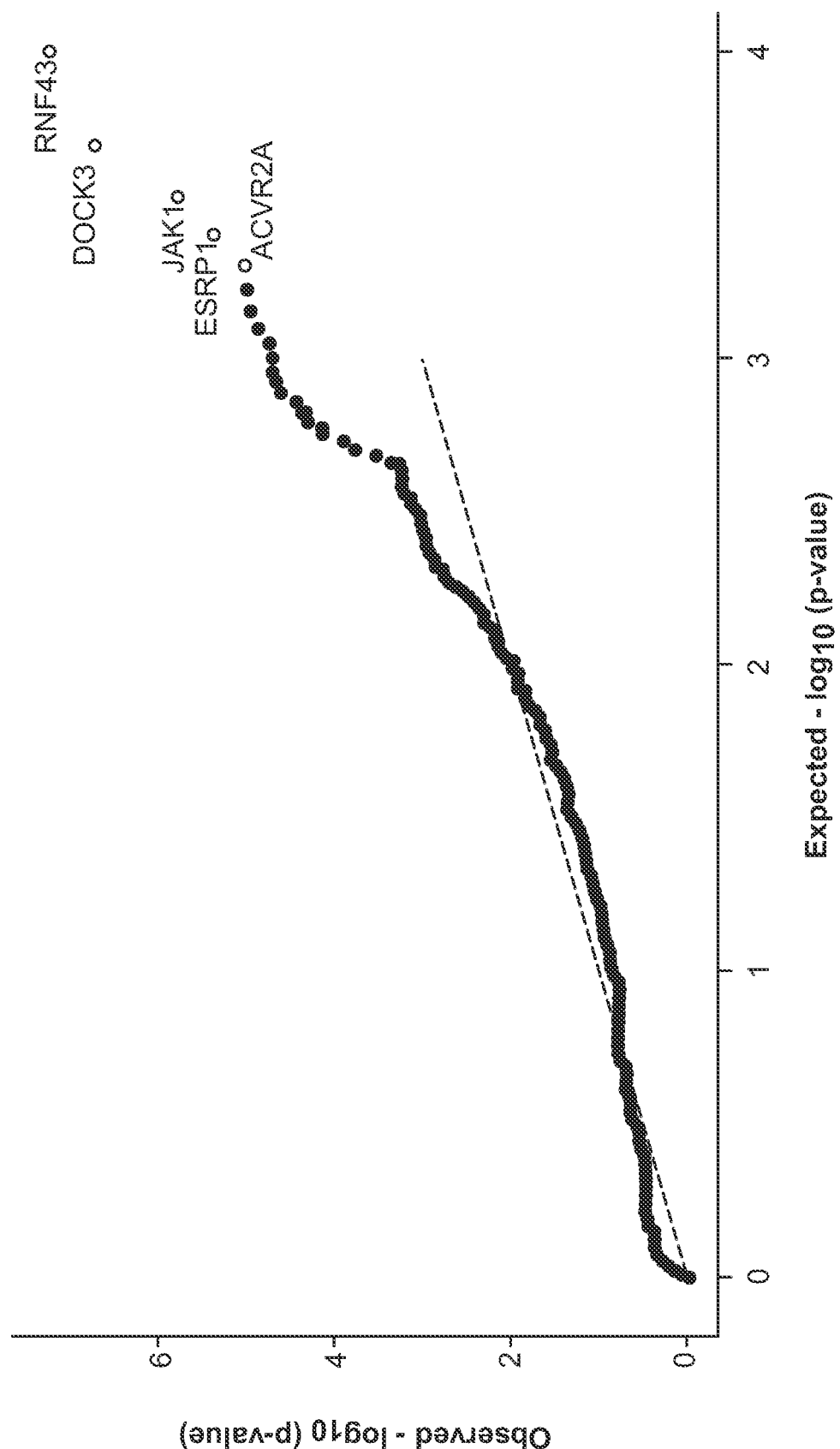
FIG. 16 is a graph showing an exemplary MSMutSig QQ plot for endometrial cancer (UCEC). Quantile-quantile plot of observed vs. expected P-values under the negative binomial (also called gamma-Poisson) model. Significant MS loci (q<0.1) are shown in red.

MSMutSig, A Tool for Identifying Novel Cancer-associated MS hotspots. The techniques herein next applied an unbiased, genome-wide approach to identify genes in which MS indels occur at a frequency higher than expected by chance. To this end, the techniques herein extended the MutSig suite of tools[15] for detecting candidate cancer genes and developed MSMutSig to specifically address the unique properties of MS indels. To maximize sensitivity, the techniques herein again chose to focus on the ~250,000 MS loci that had less than 10% diversity in normal samples. The techniques herein found that the two major factors (covariates) that influenced the mutation frequency of an MS locus were the motif sequence and repeat length (FIG. 3C). Therefore, the techniques herein estimated the background mutation frequency for each motif and repeat length separately. In a simple model in which MS loci that share the same covariate values have the same indel mutation rate ($\mu$), the number of samples that harbor a mutation in any such locus would follow a binomial distribution—e.g., bino(S, $\mu$)—where S is the total number of samples. The techniques herein first applied this model to the ~238,000 MS loci that are covered by WES but reside in non-coding regions (such as introns and UTRs), where fewer cancer driver events are expected to occur. However, even at these MS loci, there was a clear deviation from a binomial distribution, with many loci harboring more mutations than predicted by the binomial model (FIG. 16). To address this, the techniques herein applied a more dispersed distribution—the negative-binomial—that has an additional parameter that can capture this increased variability. The techniques herein fit this extra parameter such that no MS loci in non-coding regions would be nominated as significantly mutated (i.e., Benjamini-Hochberg FDR q<0.1). Reassuringly, this model also captured the variability of MS indel rates in coding regions, as indicated by the quantile-quantile plot showing that the majority of MS loci follow the null distribution (FIGS. 14-16).

Figure 3D:
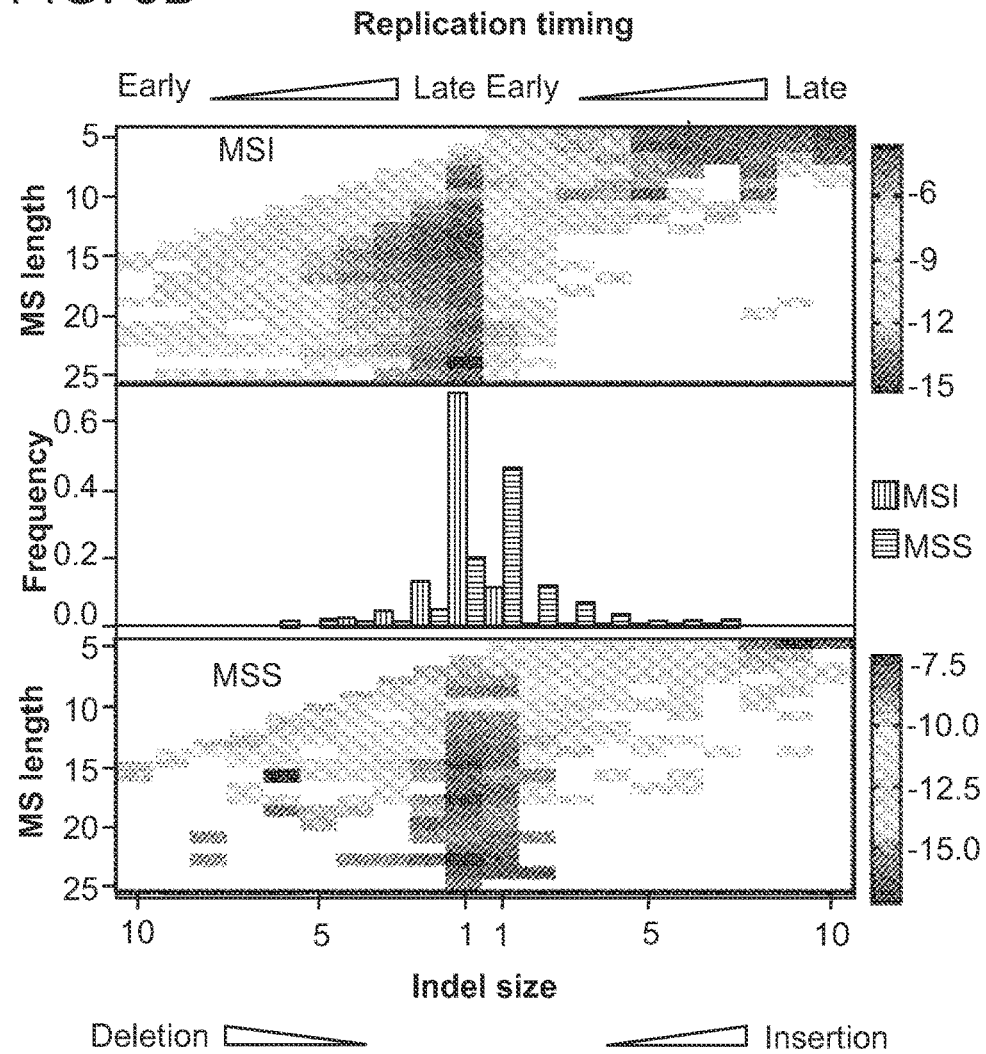

After calibrating the tool, the techniques herein applied MSMutSig across the 20 tumor types. For the three tumor types with high frequencies of MSI cases (COAD, STAD, and UCEC), the techniques herein considered the MSS and MSI subgroups (as defined by TCGA) separately since they have distinct covariate properties (FIG. 3B-D). The only tumor types that yielded significant MS loci (q<0.1) were the MSI subtypes of COAD, STAD, and UCEC. In COAD, the techniques herein identified 3 significant MS loci in the genes ACVR2A, RNF43 and DOCK3; in STAD, 4 loci in ACVR2A, RNF43, MSH3 and PRDM2; and in UCEC, 5 loci in RNF43, DOCK3, JAK1, ESRP1 and ACVR2A. Thus, the analysis nominated a total of 7 MS hotspots in 7 genes (Table C). Three of these genes (ACVR2A, RNF43 and JAK1) have been previously identified as cancer genes based on an increased mutation frequency in one or more tumor types[6]. In the TCGA colon cancer study[28], MSH3 was not nominated as significantly mutated but was noted to be highly mutated by manual examination of the sequence data. The remaining three genes (ESRP1, PRDM2 and DOCK3) have not previously been identified as cancer genes. However, it is important to note that when looking beyond major cancer genome studies, the literature is mixed regarding which of the 17,398 genes with MS loci are associated with cancer; for example, ~500 of these genes are listed as potentially involved in cancer in at least one publication (Cederquist[29] and references therein). Therefore, despite robust statistical support provided by MSMutSig, direct experiments are warranted to further clarify the driver roles of the 7 significant MS indel hotspots and genes. Of note, the gene list is missing some previously identified cancer drivers such as TGFRB2[30] and RPL22[31], both of which were excluded in the analysis due to high variability in germline samples (diversity of 17% in TGFRB2 and 15% in RPL22).

TABLE C

Significantly Mutated MS Loci

| Tumor set | Gene | Protein/ genomic change | Mutated samples | Expected mutated samples | p-value | q-value | Most common MS indel* |
|---|---|---|---|---|---|---|---|
| COAD-MSI | ACVR2A | p.K437fs g.chr2:1 48683686_148683693delA | 80% (32/40) | 6.25% (2.5/40) | $6.4 \times 10^{-9}$ | $3.1 \times 10^{-5}$ | $A_8 \rightarrow A_7$ (100%) |
| COAD-MSI | RNF43 | p.G659fs g.chr17:56435161_56435167delC | 40% (16/40) | 4.25% (1.7/40) | $6.1 \times 10^{-6}$ | 0.015 | $C_7 \rightarrow C_6$ (100%) |

TABLE C-continued

Significantly Mutated MS Loci

| Tumor set | Gene | Protein/ genomic change | Mutated samples | Expected mutated samples | p-value | q-value | Most common MS indel* |
|---|---|---|---|---|---|---|---|
| COAD-MSI | DOCK3 | p.T1850fs g.chr3:51417604_51417610delC | 39% (14/36) | 4.4% (1.6/36) | $2.1 \times 10^{-5}$ | 0.08 | $C_7 \rightarrow C_6$ (86%) |
| STAD-MSI | ACVR2A | p.K437fs g.chr2:148683686_148683693delA | 75% (52/69) | 4.5% (3.1/69) | $2.6 \times 10^{-9}$ | $9.1 \times 10^{-6}$ | $A_8 \rightarrow A_7$ (100%) |
| STAD-MSI | RNF43 | p.G659fs g.chr17:56435161_56435167delC | 35% (24/69) | 2.9% (2/69) | $1.9 \times 10^{-6}$ | 0.0034 | $C_7 \rightarrow C_6$ (100%) |
| STAD-MSI | MSH3 | p.K383fs g.chr5:79970915:79970922delA | 41% (28/69) | 4.5% (3.1/69) | $3.2 \times 10^{-5}$ | 0.037 | $A_8 \rightarrow A_7$ (85%) |
| STAD-MSI | PRDM2 | p.K1489fs g.chr1:14108749:14108757delA | 48% (33/69) | 8.7% (6/69) | $8.2 \times 10^{-5}$ | 0.07 | $A_9 \rightarrow A_8$ (93%) |
| UCEC-MSI | RNF43 | p.G659fs g.chr17:56435161_56435167delC | 23% (36/155) | 0.7% (1.2/155) | $1.6 \times 10^{-6}$ | 0.016 | $C_7 \rightarrow C_6$ (84%) |
| UCEC-MSI | DOCK3 | p.T1850fs g.chr3:51417604_51417610delC | 23% (33/145) | 1.6% (2.3/145) | $3.9 \times 10^{-6}$ | 0.019 | $C_7 \rightarrow C_6$ (81%) |
| UCEC-MSI | JAK1 | p.N860fs g.chr1:65306997:65307004delA | 21% (33/158) | 2.2% (3.5/158) | $1.45 \times 10^{-5}$ | 0.05 | $A_8 \rightarrow A_7$ (89%) |
| UCEC-MSI | ESRP1 | p.K511fs g.chr8:95686611:95686618delA | 20% (31/158) | 2.2% (3.5/158) | $3 \times 10^{-5}$ | 0.076 | $A_8 \rightarrow A_7$ (94%) |
| UCEC-MSI | ACVR2A | p.K437fs g.chr8:95686611:95686618delA | 18% (29/157) | 2.2% (3.5/157) | $5.9 \times 10^{-5}$ | 0.096 | $A_8 \rightarrow A_7$ (93%) |

Figure 4:
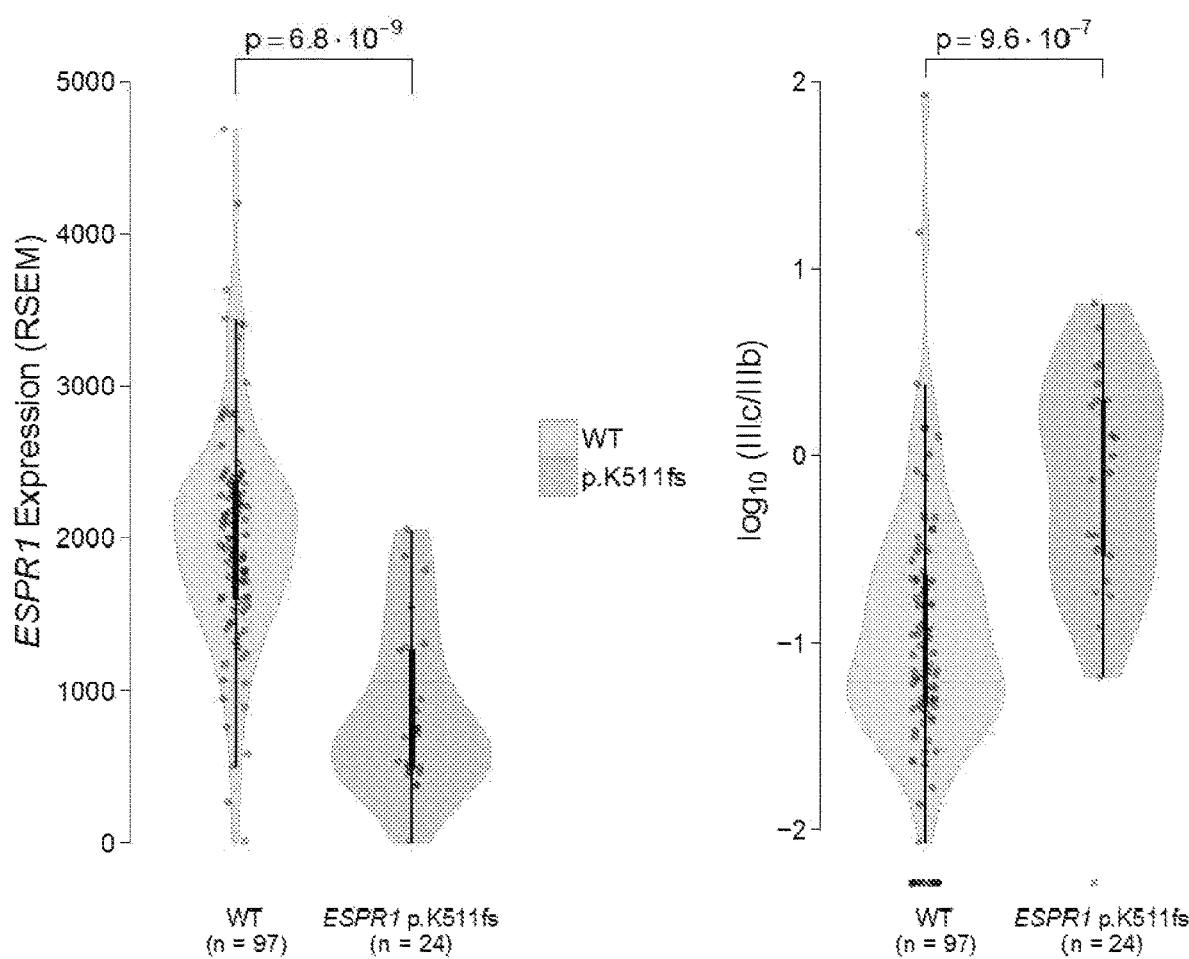
FIG. 4 depicts dot plots that show the transcriptional effects of the ESRP1 p.K511fs MS indel mutation. ESRP1 expression levels are significantly lower in ESRP1 mutant (p.K511fs) versus wild type (WT) MSI tumors from the UCEC cohort (P<1.5×10$^{-9}$, Mann-Whitney test). The ratio of FGFR2 isoform IIIc to IIIb is significantly higher (p-value<10$^{-7}$, Mann-Whitney test) in ESRP1 mutant tumors compared to WT tumors. Increased ratio of FGFR2 isoform IIIc to IIIB is associated with epithelial to mesenchymal transition.
Figure 5:
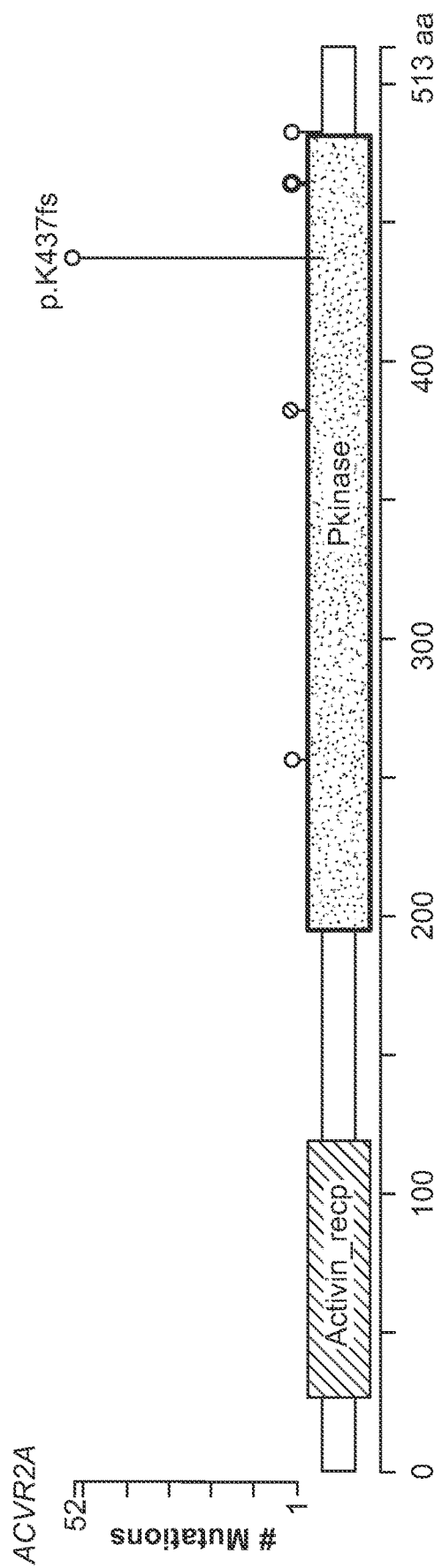
FIG. 5 is a schematic that shows the location of ACVR2A MS indel mutations in MSI-H stomach adenocarcinoma (STAD) samples. The MS indel hotspot p.K437fs was identified in 52 of 69 cases (MSMutSig q=2.4×10$^{-7}$) and had not been previously identified in these samples.

*the percentage of tumors harboring the most common MS indel is shown in parentheses All seven of the significantly mutated MS indels identified by MSMutSig cause a frameshift mutation within an exon. Frameshift mutations typically result in decreased gene expression because the altered mRNA undergoes nonsense-mediated decay[32]. However, if a frameshift mutation occurs near the end of a gene, nonsense-mediated decay is less likely to occur[33]. In such cases, indels can result in a protein with altered function. Of the 7 MS indels identified here, four (in ESRP1, MSH3, JAK1, and PRDM2) lead to a significant reduction in mRNA expression levels (Table C, FIG. 4). The MS indels in ACVR2A and DOCK3 occur near the 3' end of the gene and thus are not expected to lead to nonsense-mediated decay. The MS indel in RNF43 is in the second to last exon, but more than 50 bp[34] before its end. However, the presence of this indel does not correlate with a reduced RNF43 expression level (Mann-Whitney P=0.4), and may represent an exception to the '50 bp rule', similar to UPF1.[35]

Genes with Significantly Mutated MS Indels are Candidate Cancer Drivers. The ACVR2A gene, encoding Activin A Receptor Type IIA, harbors the most frequently mutated novel MS locus in the list (p.K437fs), with mutations in ~80% (32/40) of MSI colon tumors, ~75% (52/69) of MSI stomach tumors, and ~19% (29/157) of MSI endometrial tumors (Table C). ACVR2A is a member of the TGF-β signaling pathway, which plays a major role in cell growth and is known to be highly mutated in all three of these tumor types. Consistent with a role as a tumor suppressor, two studies[36,37] showed that expression of wild type ACVR2A in MSI colon cancer cell lines with mutated ACVR2A led to reduced cell growth. While previous studies have reported high rates of ACVR2A mutations in colorectal MSI tumors[28], the gene was not nominated as significantly mutated in the TCGA study. However, the results suggest that ACVR2A may be a driver of MSI tumors. When these novel MS indel events are considered along with other reported alterations, ACVR2A is among the most frequently mutated genes in colorectal cancer with mutations in approximately 20% of all cases (MSI and MSS).

The gene encoding Ring Finger Protein 43 (RNF43) harbors the MS indel p.G659fs in 40% (16/40) of MSI colon tumors, 35% (24/69) of MSI stomach tumors and 23% (36/155) of MSI endometrial tumors. RNF43 is a negative regulator of the WNT signaling pathway, which is involved in controlling cell proliferation[38]. Even though not reported to be a driver gene by the TCGA[28,31,39], Giannakis et al.[7] recently detected the same RNF43 MS indel through manual review of RNF43 sequence data and determined that it is frequently present in colon and endometrial tumors and is mutually exclusive with APC mutations in colon tumors. The same event has also been reported to be common in STAD[40].

The gene encoding the protein MutS Homolog 3 (MSH3) is a member of the Mismatch Repair (MMR) pathway. Germline mutations in MSH3 are known to increase the risk of developing MSI tumors[41] The techniques herein identified the MS indel hotspot p.K383fs in 40% (28/69) of stomach tumors. Similar to ACVR2A, the indel in MSH3 was also found in colon tumors[28] but was not nominated as significantly mutated, likely due to exclusion based on its presence in the normal samples. It has been shown in mouse models that while inactivation of MSH3 alone does not lead to cancer, loss of MSH3 and MSH6 results in an increased rate of tumor formation[42].

Figure 17:
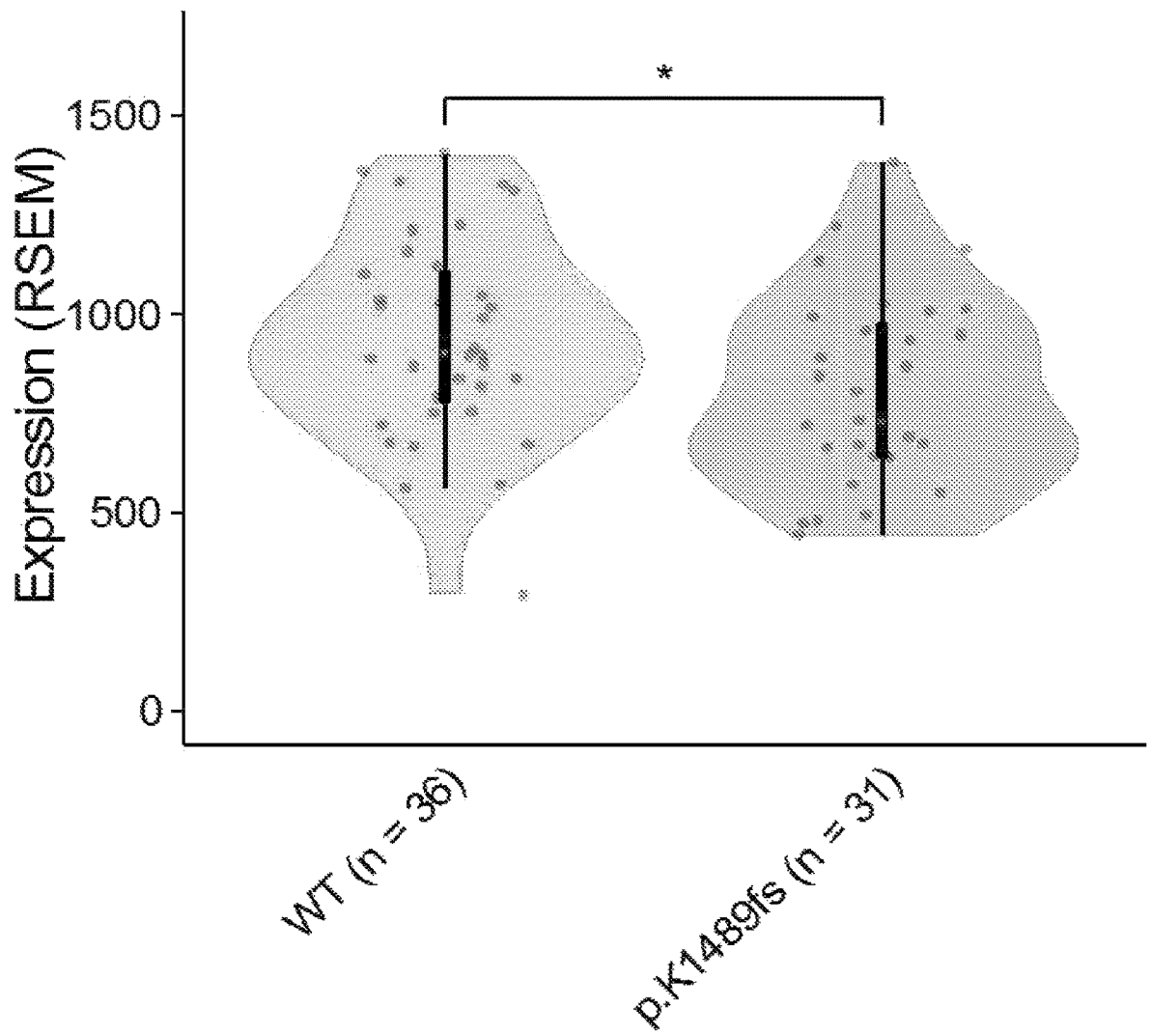
FIG. 17 is a dot plot showing PRDM2 expression in WT vs mutant PRDM2 cases. PRDM2 expression (by RNAseq) was lower in cases with a PRDM2 p.K1489fs frameshift mutation than in PRDM2 WT cases (P=0.016, Mann-Whitney test).

The gene that encodes the protein PR domain 2 (PRDM2), previously called RIZ (retinoblastoma protein-interacting zinc finger protein), is a histone H3 lysine 9 methyltransferase and has been implicated as a tumor suppressor in several tumor types[43]. For example, decreased PRDM2 expression has been associated with development of renal cell carcinoma[44], esophageal squamous cell carcinoma[45] and meningiomas[46]. The techniques herein identified the MS indel hotspot p.K1489fs in 48% (33/69) of stomach tumors. Analysis of gene expression data revealed decreased expression in mutated cases (P=0.016 Mann-Whitney; FIG. 17), consistent with partial nonsense-mediated decay.

The epithelial splicing regulatory protein 1 (ESRP1) is an epithelial cell-type-specific splicing regulator[47]. Its MS indel hotspot (ESRP1 p.K511fs) is mutated in approximately 20% (31/158) of MSI endometrial tumors. ESRP1 regulates alternative splicing of FGFR2[47] from the IIIc mesenchymal isoform to the IIIb epithelial isoform[47]. Thus, mutations in ESRP1 may contribute to the epithelial-mesenchymal transition (EMT). In pancreatic cancer[48], the transition from expression of the FGFR2-IIIb isoform to the FGFR2-IIIc isoform is associated with increased cell growth, migration, and invasion. The techniques herein analyzed TCGA RNA-seq data from these samples and found that MS indels in ESRP1 were associated with a significant decrease in ESRP1 expression (FIG. 4; P<1.5×10- Mann-Whitney). Consistent with its role in controlling FGFR2 splicing, the techniques herein also observe a significant increase in the ratio of isoform IIIc to IIIb in ESRP1 mutant cases (FIG. 4; P<9×10$^{-7}$ Mann-Whitney).

The finding that JAK1 harbors the frameshift mutation p.N860fs in 21% (33/158) of endometrial tumors (Table C) was somewhat unexpected given JAK1's known role as an oncogene in the JAK-STAT signaling pathway[49]. Park et al[25] found that the JAK1 p.N860fs indel is associated with repression of transcript levels of JAK1 downstream targets, and a recent study[50] suggested that truncated JAK1 modulates the IFNγ signaling pathway and enables the cell to evade immune surveillance. The techniques herein compared expression of an IFNγ-mediated gene signature[51] in tumors with or without the JAK1 p.N860fs indel and found a significant reduction in expression in 21 of 27 IFNγ-related genes in tumors with the p.N860fs indel. Therefore, JAK1 loss may promote tumor survival by inhibiting an IFNγ-mediated antitumor immune response.

Finally, DOCK3 encodes the protein Dedicator of cytokinesis 3 and carries the MS indel mutation p.T1850fs in 40% of colon tumors (16/40) and 23% of endometrial tumors (33/145) (Table C), DOCK3 (also known as MOCA) is an exchange factor for Rac GTPases and was recently implicated as an inhibitor of the WNT signaling pathway[52]. CTNNB1, a core member of the WNT pathway, is mutated in approximately 30% of endometrial tumors, and DOCK3 mutations are mutually exclusive with CTNNB1 mutations (P<0.015, hypergeometric test in UCEC MSI cases; P<0.005 among all UCEC cases).

Microsatellites are abundant in the human genome and are characterized by high indel mutation rates resulting from gain or loss of MS motif repeats. However, accurately detecting somatic alterations in microsatellites across cancer genomes presents a major challenge because the repetitive nature of MS loci increases the risk of sequencing-related errors, making it difficult to differentiate real from artifactual indels. Here, the techniques herein introduce MSMuTect, a tool for accurately identifying somatic indels in MS loci, and MSMutSig, a tool for identifying candidate cancer genes with significantly enriched MS indel events.

MSMuTect has several important differences from other methods that have been used to characterize the MS landscape in cancer. MSMuTect relies on careful realignment of MS-containing reads to MS loci and uses a principled statistical test to identify somatic events by applying an empirical noise profile based on motif and repeat length. Given the wide variation in background mutation rates across MS loci, this approach is important to reduce the rate of false positive MS indel calls. An alternate method for detecting somatic MS indels was recently reported by Hause et al[13] and nominates a somatic MS indel if even a single tumor read supports a different number of motif repeats than the normal sample. This approach for calling MS indels results in a large number of apparent MS indels, with an average of ~1,200 MS indels per MSS sample—approximately 10 times the average number of SNVs in those samples. In contrast, MSMuTect nominated <10 MS indels in MSS cases.

MSMuTect infers the true allele in both the tumor as well as the normal (germline) sample, and MS indels are nominated only when the observed MS repeat lengths in the tumor are better fit by the tumor allele than by the normal allele. A recent report by Kim et al[25] used the Kolmogov-Smirnov test to compare repeat length distributions in the tumor and normal sample at each MS locus for a limited set of endometrial and colon cancers. Although the total number of reported MS loci is comparable to the number identified by MSMuTect (median of ~150 for MSI-H cases and ~2 for MSS), the Kolmogorov-Smirnov test does not provide the actual (potentially multiple) alleles in the tumor and normal samples. In addition to reducing the risk of false-positive MS indel calls, identifying MS alleles in the normal sample has the potential to discover novel germline MS indels. Indeed, the techniques herein found that a small percentage of cases (5/6748, 0.075%) had a germline RNF43 allele that was identical to the most common somatic RNF43 mutant allele, raising the possibility of an inherited pathogenic RNF43 MS indel. Similarly, a study by Taupin et al identified that inherited RNF43 variants are a risk factor for the familial cancer syndrome serrated polyposis[53].

The techniques herein applied MSMuTect across 6,747 cases representing 20 tumor types from the TCGA dataset and identified nearly 175,000 MS indels. As expected, the tumor types with the highest rates of MS indels were those classically associated with the MSI phenotype—colon, rectal, stomach, and endometrial tumors. However, several other tumor types—including breast and cervical cancers— had a notable percentage of cases with high numbers of MS indels, suggesting that the MSI phenotype also occurs in these tumor types and that MSI testing may be warranted for these tumors in certain clinical settings, such as screening for enrollment on trials of immunotherapy agents[10,54,55].

In addition to identifying MS indels across the genome, the techniques herein sought specifically to identify MS indels in known cancer genes, as it was reasoned these may represent driver events. Using MSMuTect, the techniques herein identified 1470 MS indels across 727 cancer genes, of which only 89 had been previously identified by TCGA. Notably, more than 1100 of the identified MS indels occurred in tumors that lacked another MS indel or a non-synonymous SNV in the affected gene, thus raising the possibility that loss-of-function of these genes may be contributing to the tumor phenotype. To validate these findings, the techniques herein analyzed RNA-seq data for evidence of MS indels. In 87% of MS loci that had ≥4 RNA-seq reads, the RNA sequence reflected the MS indel predicted by MSMuTect. In addition, the techniques herein were able to observe all non-reference alleles in the RNA-seq data from 4 of 5 cases in which MSMuTect detected more than one mutated allele, demonstrating another advantage of inferring exact alleles rather than simply detecting differences between tumor and normal samples.

In addition to profiling MS indels at the gene level, the techniques herein found that the density of MS indels across the genome is dependent on local genomic features that are distinct from the genomic features associated with SNV density. While late-replicated regions are associated with a dramatic increase in SNV mutation rate[14], MS indel mutation rates do not show such an increase. The factor that was most strongly associated with MS indel mutation rate was the number of repeated motifs, with mutation rate increasing markedly as the number of repeats increases (FIG. 3).

Tumor MSI status can have important prognostic and therapeutic implications, and clinical MSI designation has traditionally relied on immunohistochemical analysis of MMR proteins or on PCR-based measures of MS repeats at a defined set of MS loci[12]. PCR-based MSI testing was performed for the TCGA COAD, STAD, and UCEC cohorts, and tumors were categorized as MSI-H, MSI-L, or MSS. The techniques herein found a significant difference in MS indel frequency between MSI-H and both MSI-L and MSS tumors, but the difference between MSI-L and MSS tumors was less significant. Furthermore, there was significant variability in MS indel frequency within each MS subgroup, suggesting that tumors within each subgroup may actually have different degrees of MS instability. This variability was most notable for endometrial tumors. Given that the PCR-based MSI assay was developed and validated in colorectal cancer, the apparent increased variability in MS indel frequency in endometrial cancer may reflect differences in MS properties at the Bethesda loci across tumor types.

Many of the MSI-L tumors had MS indel frequencies similar to those of MSS tumors, suggesting that some were misclassified by the MSI assay. However, a subset of MSI-L tumors—particularly endometrial tumors—had MS indel frequencies that more closely resembled MSI-H tumors. In an attempt to understand the underlying mechanism of increased MS indels among these MSI-L tumors, the techniques herein investigated a potential interaction between somatic POLE mutations and MS indel frequency. Tumors harboring a point mutation in the exonuclease (proofreading) domain of POLE (or POLD1) have dramatically increased rates of SNVs, and the techniques herein found that many of the MSI-L (and MSS) tumors with highest MS indel counts had a somatic POLE exonuclease domain mutation and an SNV signature consistent with POLE-mediated mutagenesis (FIG. 3a). Based on the co-occurrence of an MSI-SNV signature, some of these endometrial tumors appeared to have concomitant POLE mutations and MSI while other MSI-L tumors had an SNV signature consistent with a POLE/MSS phenotype despite the relatively high number of MS indels. It is believed that this is the first description of an interaction between somatic POLE mutations and MS indels in cancer; however, a similar association between POLE mutations and increased frequency of MS indels has been reported in yeast[56]. The mechanism underlying this association requires further investigation, but it is possible that a dramatic increase in SNVs resulting from loss of POLE proofreading may saturate MMR capacity (which corrects both SNVs and indels) and indirectly results in an increased number of unrepaired MS indels.

Finally, the techniques herein noted that many of the MSI endometrial tumors with lowest MS indel frequencies lacked the MSI-SNV signature, suggesting that these tumors may have been mis-classified as MSI, again underscoring the apparent discrepancy between the PCR-based MSI assay and mutational data derived from whole exome sequencing. These results highlight the shortcomings of current clinical MSI assays and, given the recent identification of MSI as a biomarker of immunotherapy response, underscore the need for sensitive and reliable MSI assays[10,54].

Figure 18:
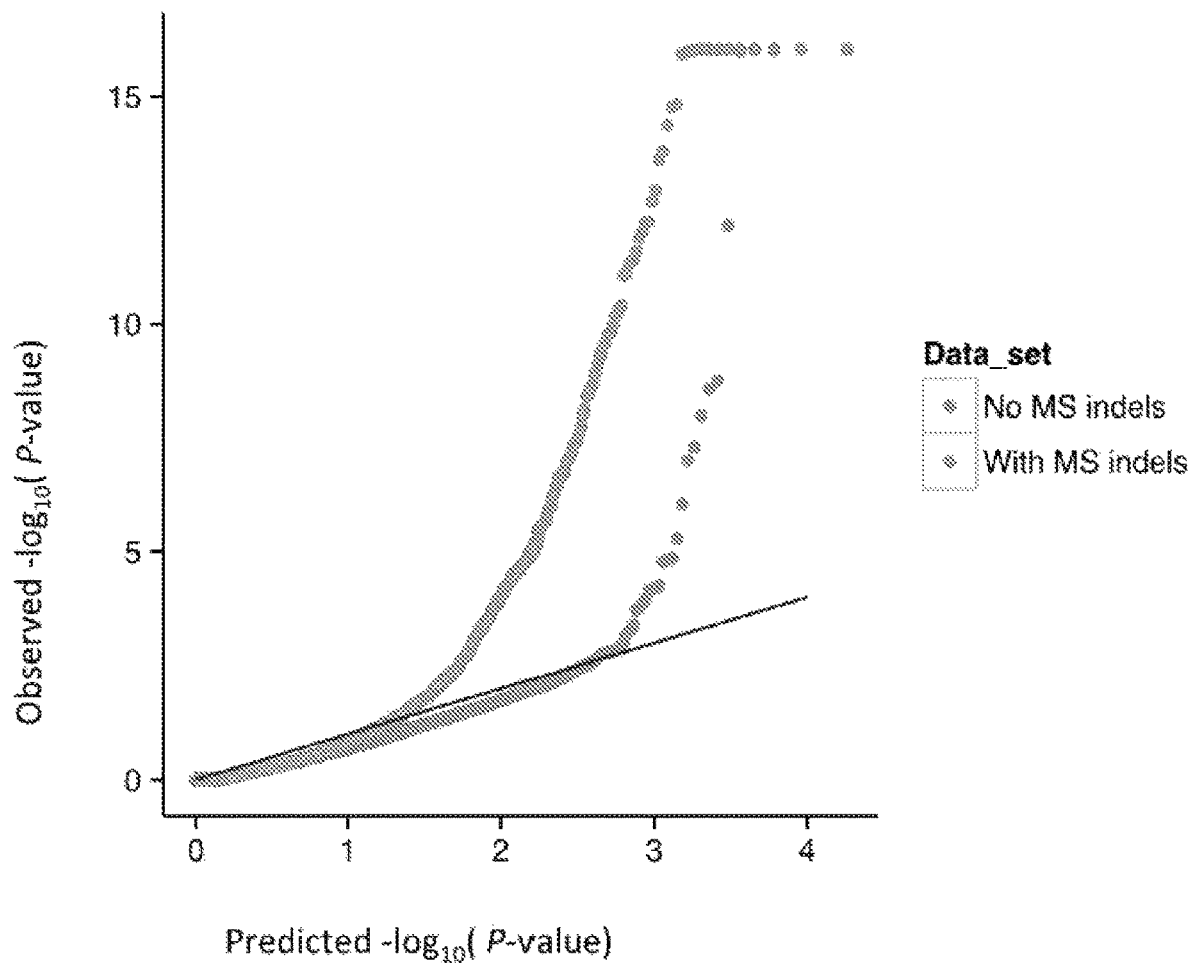
FIG. 18 shows a MutSig QQ plot for endometrial cancer (UCEC). Quantile-quantile plot of observed vs. expected P-values for MSI-H cases using only previously identified mutations (red) and using previously identified mutations and MS indels (green). Using MutSig for datasets with large numbers of MS indels leads to an inflation in the number of significantly mutated genes.

Based on the understanding of the features that influence the indel mutation rate at MS loci, the techniques herein were able to develop MSMutSig, a tool that searches for MS loci that are mutated more frequently than expected by chance. MutSig[15] was developed to handle SNVs and general indels (not necessarily within MSs), and its background mutation rate model does not fit the unique properties of MS indels; therefore, attempts to use MutSig to identify genes with recurrent MS indel events may over-estimate the number of significant genes. Indeed, applying MutSig to the MSI-H endometrial cohort using all mutations (SNVs and general indels identified by MuTect in addition to MS indels identified by MSMuTect) yielded 296 significant genes (q<0.1) and an inflated Q-Q plot, suggesting that it uses an inadequate null model (FIG. 18). However, when the techniques herein excluded the MS indels, MutSig yielded a well-calibrated Q-Q plot in which nearly all genes followed the null hypothesis, with only 21 significant genes (q<0.1), most of which are well-known cancer genes. Historically, many genes have been proposed to drive cancer based on a high frequency of MS indels[29]; however, the analysis suggests that most of these MS loci have a high indel mutation rate and therefore may be frequently mutated but not confer any fitness advantage to the cancer cells.

Applying MSMutSig across the cohort of 6,747 tumors, the techniques herein identified seven significantly recurrently mutated MS loci, three of which occurred in genes not previously nominated as cancer genes (ESRP1, PRDM2 and DOCK3). All seven recurrent MS indels result in frameshift mutations, and analysis of RNA-seq data confirms decreased expression in four of seven cases. The frameshift mutations in the other three genes (ACVR2A, RNF43 and DOCK3) occur near the 3' end of the gene and are thus less likely to result in nonsense-mediated decay, but nonetheless do not encode a full-length protein. Although the data strongly support a role for these MS indels as cancer drivers, direct experimental studies will be needed to further investigate the specific role of these mutations in cancer.

Here, the techniques herein use MSMuTect and MSMutSig to characterize MS indels across cancer and identify MS indel hotspots through a process of global realignment of MS reads and application of an empirically-derived noise model to determine the most likely set of alleles for both tumor and normal samples. Through rigorous false-positive and false-negative analysis, the techniques herein demonstrate that MSMuTect is robust across MS motif sequences and lengths. In the significance analyses, the techniques herein assumed that all MS indels in non-coding regions were not under selective pressure and thus could serve as an upper estimate of the indel mutation rate arising from technical factors (PCR errors, etc.). However, cancer driver mutations are known to exist in regulatory regions (e.g. in promoters)[57], and a deeper understanding of the covariates influencing MS indel rates across the genome may eventually enable us to adapt MSMutSig for accurate detection of significantly mutated MS loci in non-coding regions. Similarly, adapting MSMuTect for whole genome analysis and applying it across a large cohort of WGS samples may further improve the sensitivity of MSMuTect and MSMutSig by providing a more accurate noise model across loci of varying motif and repeat lengths. In addition, technical advances may also lead to improvements in MS indel calling. For example, sequencing technologies that produce longer read lengths will provide better coverage of long MS loci and enable more accurate mutation-calling for longer MS repeats. Finally, integrating MS indel calling tools such as MSMuTect with tools for identifying other recurrent genomic events such as SNVs or copy number alterations (CNAs) will provide a comprehensive view of cancer driving events.

MSI testing is advantageous for diagnostic testing and possesses utility in predicting an immunotherapeutic response especially in patients who have failed conventional therapy.

MSI status has been used to predict outcomes (reviewed by Dudley et al., Clin Cancer Res; 22(4); 813-20). MSI colorectal cancer is associated with a lower stage at diagnosis and improved stage-specific prognosis (though conflicting results have been observed in stage IV patients), the likely result of a significant immunologic response elicited by neoepitopes. Assessing for somatic mutations in BRAF in conjunction with MSI status is also prognostically valuable. The p.V600E mutation renders BRAF constitutively active, resulting in a worse prognosis. A recent study stratified colorectal cancer patients based on MSI and BRAF status into three prognostic groups: MSI/BRAF-wild type or mutant (best prognosis), MSS/BRAF-wild type (intermediate prognosis), and MSS/BRAF mutant (worst prognosis), though other studies have reached conflicting results, and no consensus exists to date on the best prognostic subgroupings.

The diagnostic tests are typically conducted on a biological sample selected from for example tumor biopsy samples, blood samples (isolation and enrichment of shed tumor cells), stool biopsies, sputum, chromosome analysis, pleural fluid, peritoneal fluid, buccal spears or biopsy or from urine.

The present disclosure also involves other methods for detecting the MS indels of the present disclosure. Whole genome or whole exome sequencing is preferred; however, other methods of sequencing and hybridization are also envisioned.

RNA sequencing (RNA-Seq) is a powerful tool for transcriptome profiling but is hampered by sequence-dependent bias and inaccuracy at low copy numbers intrinsic to exponential PCR amplification. To mitigate these complications to allow truly digital RNA-Seq, a large set of barcode sequences is added in excess, and nearly every cDNA molecule is uniquely labeled by random attachment of barcode sequences to both ends (Shiroguchi K. et al. Proc Natl Acad Sci USA. 2012 Jan. 24; 109(4):1347-52). After PCR, paired-end deep sequencing is applied to read the two barcodes and cDNA sequences. Rather than counting the number of reads, RNA abundance is measured based on the number of unique barcode sequences observed for a given cDNA sequence (Shiroguchi K, et al. Proc Natl Acad Sci USA. 2012 Jan. 24; 109(4):1347-52). The barcodes may be optimized to be unambiguously identifiable, even in the presence of multiple sequencing errors. This method allows counting with single-copy resolution despite sequence-dependent bias and PCR-amplification noise and is analogous to digital PCR but amendable to quantifying a whole transcriptome (Shiroguchi K, et al. Proc Natl Acad Sci U.S.A. 2012 Jan. 24; 109(4):1347-52).

Fixation of cells or tissue may involve the use of cross-linking agents, such as formaldehyde, and may involve embedding cells or tissue in a paraffin wax or polyacrylamide support matrix (Chung K, et al. Nature. 2013 May 16; 497(7449): 322-7).

Amplification may involve thermocycling or isothermal amplification (such as through the methods RPA or LAMP). Cross-linking may involve overlap-extension PCR or use of ligase to associate multiple amplification products with each other.

For purpose of this disclosure, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Sequencing may be performed on any high-throughput platform with read-length (either single- or paired-end) sufficient to cover both template and cross-linking event UID's. Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

The present disclosure may be applied to (1) single-cell transcriptomics: cDNA synthesized from mRNA is barcoded and cross-linked during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (molecular microscopy or VIPUR microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer immunoglobulins (by analyzing co-localization of B-cells and T-cells within affected tissue) for immunotherapy.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "variant" should be taken to mean the exhibition of qualities that differ, such as, but not limited to, genetic variations including SNPs, insertion deletion events, and the like.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this disclosure it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the disclosure, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin. U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, e.g., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Embodiments of the disclosure include sequences (both polynucleotide or polypeptide) which may comprise homologous substitution (substitution and replacement are both used herein to mean the interchange of an existing amino acid residue or nucleotide, with an alternative residue or nucleotide) that may occur e.g., like-for-like substitution in the case of amino acids such as basic for basic, acidic for acidic, polar for polar, etc. Non-homologous substitution may also occur e.g., from one class of residue to another or alternatively involving the inclusion of unnatural amino acids such as omithine (hereinafter referred to as Z), diaminobutyric acid ornithine (hereinafter referred to as B), norleucine omithine (hereinafter referred to as O), pyriyl-alanine, thienylalanine, naphthylalanine and phenylglycine.

The practice of the present disclosure employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Hybridization can be performed under conditions of various stringency. Suitable hybridization conditions for the practice of the present disclosure are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present disclosure include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, li-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5'''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red): N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700: IRD 800; La Jolta Blue; phthalo cyanine; and naphthalo cyanine The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terrylen. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten or peptide. An index sequence is a sequence which may comprise a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present disclosure also relates to a computer system involved in carrying out the methods of the disclosure relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present disclosure can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the disclosure. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the disclosure, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

The present disclosure also contemplates multiplex assays. The present disclosure is especially well suited for multiplex assays. For example, the disclosure encompasses use of a SureSelect$^{XT}$, SureSelect$^{XT2}$ and SureSelect$^{QXT}$ Target Enrichment System for Illumina Multiplexed Sequencing developed by Agilent Technologies (see for example the World Wide Web at (www)agilent.com/genomics/protocol videos), a SeqCap EZ kit developed by Roche NimbleGen, a TruSeq® Enrichment Kit developed by Illumina and other hybridization-based target enrichment methods and kits that add sample-specific sequence tags either before or after the enrichment step. as well as Illumina HiSeq, MiSeq and NexSeq, Life Technology Ion Torrent. Pacific Biosciences PacBio RSII, Oxford Nanopore Minion, Promethlon and Gridlon and other massively parallel Multiplexed Sequencing Platforms.

Usable methods for hybrid selection are described in Melnikov, et al., Genome Biology 12:R73, 2011; Geniez, et al., Symbiosis 58:201-207, 2012; and Matranga, et al., Genome Biology 15:519, 2014). Bait design and hybrid selection was done similarly to a previously published method (see, e.g., Gnirke, et al. Nature biotechnology 27:182-189, 2009, US Patent Publications No. US 2010/0029498, US 2013/0230857, US 2014/0200163, US 2014/0228223, and US 2015/0126377 and International Patent Publication No. WO 20091099602). Briefly, baits may be designed by first concatenating all consensus sequences (such as LASV) into two single bait sets (such as one for Nigerian clades and another for the Sierra Leone clade). Duplicate probes, defined as a DNA sequence with 0 mismatches, were removed. The baits sequences were tiled across the genome (such as LASV) creating a probe every 50 bases. Two sets of adapters were used for each bait set. Adapters alternated with each 50 base probe to improve the efficiency of PCR amplification of probes. The oligo array was synthesized on a CustomArray B3 Synthesizer, as recommended by the manufacturer. The oligonucleotides were cleaved-off the array and amplified by PCR with primers containing T7 RNA polymerase promoters. Biotinylated baits were then prepared through in vitro transcription (MEGAshortscript, Ambion). RNA baits for each clade were prepared separately and mixed at the equal RNA concentration prior to hybridization. Libraries of the genome (such as LASV) were added to the baits and hybridized over a 72 hrs. After capture and washing, libraries were amplified by PCR using the Illumina adapter sequences. Libraries were then pooled and sequenced on the MiSeq platform.

Methods of inhibiting and/or treating cancer and tumors in individuals with cancer or a predisposition for developing cancer as identified by methods of the disclosure are also contemplated.

The subject has been diagnosed with cancer or is at risk of developing cancer. The subject is a human, dog, cat, horse or any animal in which a tumor specific immune response is desired. The tumor is any solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas. In an advantageous embodiment, the cancer is an adrenal, breast, cervical, colon, endometrial, rectal or stomach cancer.

The therapeutic agent is for example, a chemotherapeutic agent, radiation, or immunotherapy. Any suitable therapeutic treatment for a particular cancer may be administered. Examples of chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, tamoxifen, taxol, topotecan hydrochloride, trastuzumab, vinblastine, vincristine and vinorelbine tartrate.

For therapeutic use, administration should begin at the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The disclosure provides compositions for parenteral administration which comprise a solution of the peptides and vaccine compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In an advantageous embodiment, the cancer therapeutic is an immunotherapeutic. The immunotherapeutic may be a cytokine therapeutic (such as an interferon or an interleukin), a dendritic cell therapeutic or an antibody therapeutic, such as a monoclonal antibody. In a particularly advantageous embodiment, the immunotherapeutic is a neoantigen (see, e.g., U.S. Pat. No. 9,115,402 and US Patent Publication Nos. 20110293637, 20160008447, 20160101170, 20160331822 and 20160339090).

In an advantageous embodiment, treatments for cancer caused by MSI mutations are contemplated. In particular, if the cancer caused by one or more MSI mutations overexpresses a programmed cell death protein 1 (PD-1) receptor ligand, a PD-1 receptor ligand inhibitor may be contemplated as a treatment. Advantageously, the PD-1 receptor ligand is PD-L1. One example of a PD-L1 receptor ligand inhibitor is pembrolizumab (formerly MK-3475 and lambrolizumab, trade name Keytruda) which is known to be efficacious for MSI cancers. The present disclosure encompasses identifying whether a patient has an MSI cancer in order to know whether pembrolizumab would be a good choice for treatment for that patient, e.g., as a companion diagnostic. In particular, identifying of one or more of the mutations in any one of Tables 1, A or B in a patient.

Without being bound by theory, pembrolizumab is a therapeutic antibody that binds to and blocks the PD-1, programmed cell death protein 1 located on lymphocytes. This receptor is generally responsible for preventing the immune system from attacking the body's own tissues; by acting as an immune checkpoint. Many cancers make proteins that bind to PD-1, thus shutting down the ability of the body to kill the cancer on its own. Inhibiting PD-1 on the lymphocytes prevents this, allowing the immune system to target and destroy cancer cells. Tumors that have mutations that cause DNA mismatch repair, which often results in microsatellite instability, tend to generate many mutated proteins that could serve as tumor antigens; pembrolizumab appears to facilitate clearance of any such tumor by the immune system, by preventing the self-checkpoint system from blocking the clearance.

In particular, treatments for adrenal, breast, cervical, colon, endometrial, rectal or stomach cancer are especially contemplated.

For adrenal cancer, surgery is recommended to remove the entire adrenal gland. Standard treatment options for adrenocortical carcinoma (ACC) include, but are not limited to, chemotherapy with mitotane, chemotherapy with mitotane plus streptozotocin or mitotane plus etoposide, doxorubicin, and cisplatin, radiation therapy to bone metastases and/or surgical removal of localized metastases, particularly those that are functioning.

For breast cancer, local therapies such as surgery and radiation are recommended. Breast cancer may also be treated systemically by chemotherapy, hormone therapy (such as, but not limited to, tamoxifen, toremifene, fulvestrant or aromatase inhibitors) or targeted therapy (such as, but not limited to, monoclonal antibodies or other therapeutics that target a HER2 protein, a mTor protein or cyclin-dependent kinases, or kinase inhibitors). If the breast cancer is a BRCA cancer, the cancer may be treated and/or prevented by a mastectomy, sapingo-oophorectomy or hormonal therapy medicines, such as selective estrogen receptor modulators or aromatase inhibitors. Hormonal therapy medicines include, but are not limited to, tamoxifen, raloxifene, exemestane or anastrozole.

Cervical cancer may be treated by surgery, radiation, chemotherapy or targeted therapy (such as an angiogenesis inhibitor). Cervical squamous cell carcinoma may be treated by cryosurgery, laser surgery, loop electrosurgical excision procedure (LEEP/LEETZ), cold knife conization or a simple hysterectomy (as the first treatment or if the cancer returns after other treatments). Endocervical adenocarcinoma (CESC) may be treated by surgery or radiation.

Colon cancer may be treated by surgery or chemotherapy. Some common regimens for treating colon cancer include, but are not limited to: OLFOX: leucovorin, 5-FU, and oxaliplatin (Eloxatin); FOLFIRI: leucovorin, 5-FU, and irinotecan (Camptosar); CapeOX: capecitabine (Xeloda) and oxaliplatin; FOLFOXIRI: leucovorin, 5-FU, oxaliplatin, and irinotecan; One of the above combinations plus either a drug that targets VEGF (bevacizumab [Avastin], ziv-aflibercept [Zaltrap], or ramucirumab [Cyramza]), or a drug that targets EGFR (cetuximab [Erbitux] or panitumumab [Vectibix]); 5-FU and leucovorin, with or without a targeted drug; Capecitabine, with or without a targeted drug; Irinotecan, with or without a targeted drug; Cetuximab alone; Panitumumab alone; Regorafenib (Stivarga) alone; and/or Trifluridine and tipiracil (Lonsurf).

Endometrial cancer may be treated by surgery, chemotherapy and radiation. Uterine corpus endometrial carcinoma (UCEC) is the most common type of endometrial cancer. Operative procedures used for managing endometrial cancer include the following: exploratory laparotomy, total abdominal hysterectomy, bilateral salpingo-oophorectomy, peritoneal cytology and pelvic and para-aortic lymphadenectomy. Chemotherapeutic medications such as cisplatin can be used in the management of endometrial carcinoma. Standard treatment options for uterine carcinosarcoma (UCS) include surgery (total abdominal hysterectomy, bilateral salpingo-oophorectomy, and pelvic and periaortic selective lymphadenectomy), surgery plus pelvic radiation therapy, surgery plus adjuvant chemotherapy or surgery plus adjuvant radiation therapy (EORTC-55874).

Rectal cancer may be treated by surgery, chemotherapy and radiation. Some common regimens for treating rectal cancer include, but are not limited to: FOLFOX: leucovorin, 5-FU, and oxaliplatin (Eloxatin); FOLFIRI: leucovorin, 5-FU, and irinotecan (Camptosar); CapeOX: capecitabine (Xeloda) and oxaliplatin; FOLFOXIRI: leucovorin, 5-FU, oxaliplatin, and irinotecan; One of the above combinations, plus either a drug that targets VEGF (bevacizumab [Avastin], ziv-aflibercept [Zaltrap], or ramucirumab [Cyramza]), or a drug that targets EGFR (cetuximab [Erbitux] or panitumumab [Vectibix]); 5-FU and leucovorin, with or without a targeted drug; Capecitabine, with or without a targeted drug; Irinotecan, with or without a targeted drug; Cetuximab alone; Panitumumab alone; Regorafenib (Stivarga) alone; and/or Trifluridine and tipiracil (Lonsurf).

Stomach cancer may be treated by surgery, radiation, chemotherapy or targeted therapy (such as a monoclonal antibody or other therapeutics that target a HER2 protein or a VEGF receptor). Drugs approved for stomach cancer include, but are not limited to, Capecitabine (Xeloda), Cisplatin (Platinol), Cyramza (Ramucirumab), Docetaxel, Doxorubicin Hydrochloride, 5-FU (Fluorouracil Injection), Fluorouracil Injection, Herceptin (Trastuzumab), Irinotecan Hydrochloride, Leucovorin Calcium, Mitomycin C, Mitozytrex (Mitomycin C), Mutamycin (Mitomycin C), Ramucirumab, Taxotere (Docetaxel) and Trastuzumab and may be administered individually or in a combination thereof.

The therapeutics of the present disclosure may be delivered in a particle and/or nanoparticle delivery system. Several types of particle and nanoparticle delivery systems and/or formulations are known to be useful in a diverse spectrum of biomedical applications; and particle and nanoparticle delivery systems in the practice of the instant disclosure can be as in WO 2014/093622 (PCT/US13/74667). In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present disclosure. A particle in accordance with the present disclosure is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm. 600 nm, 500 nm, 400 nm. 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the disclosure. In some embodiments, inventive particles have a greatest dimension ranging between 25 nm and 200 nm. Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo to provide particles of an optimal size for delivery for any in vitro, ex vivo and/or in vivo application of the present disclosure. In certain preferred embodiments, particle dimension (e.g., diameter) characterization is based on measurements using dynamic laser scattering (DLS). Particles delivery systems within the scope of the present disclosure may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present disclosure.

In general, a "nanoparticle" refers to any particle having a diameter of less than 1000 nm. In certain preferred embodiments, nanoparticles of the disclosure have a greatest dimension (e.g., diameter) of 500 nm or less. In other preferred embodiments, nanoparticles of the disclosure have a greatest dimension ranging between 25 nm and 200 nm. In other preferred embodiments, nanoparticles of the disclosure have a greatest dimension of 100 nm or less. In other preferred embodiments, nanoparticles of the disclosure have a greatest dimension ranging between 35 nm and 60 nm. Nanoparticles encompassed in the present disclosure may be provided in different forms. e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semi-conducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present disclosure.

Semi-solid and soft nanoparticles have been manufactured and are within the scope of the present disclosure. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. Doses of about 5 mg/kg are contemplated, with single or multiple doses, depending on the target tissue. It is mentioned herein experiments involving mice involve 20 g mammals and that dosing can be scaled up to a 70 kg human. With regard to nanoparticles that can deliver RNA, see, e.g., Alabi et al., Proc Natl Acad Sci USA. 2013 Aug. 6; 110 (32):12881-6; Zhang et al., Adv Mater. 2013 Sep. 6; 25(33): 4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93. Lipid Nanoparticles, Spherical Nucleic Acid (SNA™) constructs, nanoplexes and other nanoparticles (particularly gold nanoparticles) are also contemplate as a means for delivery A recent publication, entitled "In vivo endothelial siRNA delivery using polymeric nanoparticles with low molecular weight" by James E. Dahlman and Carmen Barnes et al. Nature Nanotechnology (2014) published online 11 May 2014, doi:10.1038/nnano.2014.84, incorporated herein in its entirety, showed that polymeric nanoparticles made of low-molecular-weight polyamines and lipids can deliver siRNA to endothelial cells with high efficiency, thereby facilitating the simultaneous silencing of multiple endothelial genes in vivo. The authors reported that unlike lipid or lipid-like nanoparticles, the nanoparticle formulation they used (termed 7C1), differed from traditional lipid-based nanoparticle formulations because it can deliver siRNA to lung endothelial cells at low doses without substantially reducing gene expression in pulmonary immune cells, hepatocytes or peritoneal immune cells.

MSI Cancers

Colorectal Cancer (CRC)

CRC is the third most common cancer type in which about 1.4 million new cases are diagnosed each year. Additionally, CRC results in about 700,000 deaths per year. Unfortunately, the frequency of CRC appears to be increasing throughout the developed world, presumably due to increased risk of CRC associated with alcohol consumption, smoking, obesity, diabetes, the consumption of large amounts of meat, and little physical activity.

About 15% are associated with microsatellite instability (MSI), which can be defined as somatic changes in the length of microsatellites. Based on microsatellite status (e.g., MSI versus MSS), colorectal tumors can be divided into 3 the categories: 1. tumors with high levels of microsatellite instability (MSI-H), 2 tumors with low levels of microsatellite instability (MSI-L), and tumors that are microsatellite stable (MSS).

Lynch syndrome is a hereditary form of autosomal dominant colon cancer that results from inherited mismatch repair gene defects and is characterized by high levels of microsatellite instability and constitutes about 20% of MSI-H CRCs. Lynch Syndrome patients typically display initial cancer onset in their mid-forties, which is in sharp contrast to patients with sporadic MSI-H cancers where the average age is over seventy.

Sporadic MSI-H tumors are usually caused by the epigenetic silencing of MLH1 caused by promoter methylation. Traditionally, Lynch Syndrome tumors are thought to arise from adenomas, while sporadic MSI-H CRCs are believed to arise from serrated polyps. Approximately 80% of MSI-H tumors are sporadic tumors. Sporadic MSI-H tumors are generally predisposed to present in the proximal colon and are more common in women than men.

With respect to CRC, it is therefore clear that the ability to accurately assess MSI status is important because it can define hereditary forms of CRC and inform clinical care. Additionally, identifying patients with Lynch Syndrome is important because they and their relatives have a high risk of developing second primary cancers. Early detection of these cancers has a significant impact upon prognosis, and it has been estimated that more than 60% of Lynch Syndrome cancer deaths could be prevented with proper follow up.

Other exemplary MSI cancers include, but are not limited to, adenocarcinoma (COAD), stomach adenocarcinoma (STAD), and uterine corpus endometrial carcinoma (UCEC).

MSI Classification

The methods and compositions described herein relate to identification of a new and clinically useful classifier for MSI, the development of which is based upon an assessment of low pass (e.g., about 0.01×) WGS data for a neoplasia or tumor sample. Specific components of the instant MSI classifier include the following.

Reference Sequences

In certain aspects, the instant disclosure provides methods and kits that involve and/or allow for assessment of the presence or absence of one or more sequence variants and/or mutations in a test subject, tissue, cell or sample, as compared to a corresponding reference sequence. In particular embodiments, a subject, tissue, cell and/or sample is assessed for one or more variants and/or sites of copy number variation within the sequences/sequence locations (e.g., motif A as defined below).

Amplification and Sequencing Oligonucleotides

In some aspects, WGS or exome sequencing may be performed upon a test sample for purpose of detecting variants and/or copy number variation as described herein and identifying MSI classification and selecting a therapy. In certain embodiments, assessment of candidate and/or test MSI neoplasia or tumor samples can be performed using one or more amplification and/or sequencing oligonucleotides flanking the above-referenced variant sequence and/or copy number variation regions. Design and use of such amplification and sequencing oligonucleotides, and/or copy number detection probes/oligonucleotides, can be performed by one of ordinary skill in the art.

As will be appreciated by one of ordinary skill in the art, any such amplification sequencing and/or copy number detection oligonucleotides can be modified by any of a number of art-recognized moieties and/or exogenous sequences, e.g., to enhance the processes of amplification, sequencing reactions and/or detection. Exemplary oligonucleotide modifications that are expressly contemplated for use with the oligonucleotides of the instant disclosure include, e.g., fluorescent and/or radioactive label modifications; labeling one or more oligonucleotides with a universal amplification sequence (optionally of exogenous origin) and/or labeling one or more oligonucleotides of the instant disclosure with a unique identification sequence (e.g., a "bar-code" sequence, optionally of exogenous origin), as well as other modifications known in the art and suitable for use with oligonucleotides.

Neural Network Classification

In certain exemplified aspects, a neural network classifier may also be used may be used to define MSI classification groups. As would be appreciated by one of ordinary skill in the art, other forms of classifier (e.g., nearest-neighbor and various others) can be applied to variant and/or copy number data, to perform such test sample classification.

A neural network consists of units (neurons), arranged in layers, which convert an input vector into some output. Each unit takes an input, applies a function (e.g., a nonlinear function) to it and then passes the output on to the next layer. Generally the networks are defined to be feed-forward: a unit feeds its output to all the units on the next layer, but there is no feedback to the previous layer. Weightings are applied to the signals passing from one unit to another, and it is these weightings which are tuned in the training phase to adapt a neural network to the particular problem at hand. This is the learning phase.

Neural networks have found application in a wide variety of problems. These range from function representation to pattern recognition, with pattern recognition being the focus of use of neural net classifiers of the instant disclosure.

Clinical Classifier Scoring Algorithm

The techniques herein provide a classifier algorithm to identify neoplasia or tumor samples as either MSI or MSS. The classifier algorithm herein is based, in part, on using high throughput NGS systems to generate sequencing data for as many loci as possible within the neoplasia or tumor, aggregating the WGS data, and applying a weighting system for analysis. For example, if a particular MS locus has 11-15 repeats of the A motif, it may receive a weight score of 1; however, if that particular MS locus does not have 11-15 repeats of the A motif, it will receive a weight score of 0. In this regard, the techniques herein allow generation of indel signature patterns characteristic of either MSI or MSS.

Without being bound by theory, the techniques herein have identified approximately 600,000 loci having 11-15 repeats of the A motif, which means that even if the WGS data for a particular neoplasia or tumor sample has a very low pass coverage of the genome (e.g., 90%-95% of the loci are not covered at all), it will still be sufficient to accurately identify an MSI indel signature pattern and be able to assess the neoplasia or tumor sample as being either MSI or MSS.

It is expressly contemplated that a classifier of the instant disclosure can be used to link discrete genetic signatures, clinical outcome and specific targeted therapy in clinical trials and in practice. Specifically, it is contemplated that neoplasia or tumors of patients with MSI can be analyzed prospectively with an exemplified classifier or other classifier within the scope of the instant disclosure. The resulting cluster identifications are predictive of the likelihood of response to standard combination chemotherapy and suggest rational targeted therapies based on cluster-specific biology. Additionally, the resulting identifications can determine whether or not a patient is eligible for anti-PDL or anti-PDL1 treatment. It is further expressly contemplated that a classifier of the instant disclosure can also be applied retrospectively to archival tissue from patients on specific clinical trials or therapies.

Treatment Selection

The methods described herein can be used for selecting, and then optionally administering, an optimal treatment for a subject. Thus the methods described herein include methods for the treatment of cancer, particularly neoplasia or tumors associated with MSI. Generally, the methods include administering a therapeutically effective amount of a treatment as described herein, to a subject who is in need of, or who has been determined to be in need of, such treatment.

As used in this context, to "treat" means to ameliorate at least one symptom of the cancer. For example, a treatment can result in a reduction in tumor size, tumor growth, cancer cell number, cancer cell growth, or metastasis or risk of metastasis.

For example, the methods can include selecting and/or administering a treatment that includes a therapeutically effective amount of an immune checkpoint blocker such as, for example, cytotoxic T-lymphocyte antigen-4 (CTLA-4) and programmed death-1 (PD-1), to a subject having a select MSI tumor or cancer/tumor.

Therapeutic agents specifically implicated for administration in using the instant MSI classifier include inhibitors of the following genetic targets:

PD-1

The PD-1 receptor-ligand interaction is a major pathway hijacked by tumors to suppress immune control. PD-1, which is expressed on the cell surface of activated T-cells under healthy conditions, normally functions to down-modulate unwanted or excessive immune responses, including autoimmune reactions. The ligands for PD-1 (PD-L1 and PD-L2) are constitutively expressed or can be induced in various tumors. Binding of either PD-L1 or PD-L2 to PD-1 inhibits T-cell activation triggered through the T-cell receptor.

PD-L1 is expressed at low levels on various non-hematopoietic tissues, most notably on vascular endothelium, whereas PD-L2 protein is only detectably expressed on antigen-presenting cells found in lymphoid tissue or chronic inflammatory environments. PD-L2 is thought to control immune T-cell activation in lymphoid organs, whereas PD-L1 serves to dampen unwarranted T-cell function in peripheral tissues. Although healthy organs express little (if any) PD-L1, a variety of cancers were demonstrated to express abundant levels of this T-cell inhibitor. High expression of PD-L1 on tumor cells (and to a lesser extent of PD-L2) has been found to correlate with poor prognosis and survival in various cancer types, including renal cell carcinoma (RCC), pancreatic carcinoma, hepatocellular carcinoma, ovarian carcinoma and non-small cell lung cancer (NSCLC). Furthermore, PD-1 has been suggested to regulate tumor-specific T cell expansion in patients with malignant MEL. The observed correlation of clinical prognosis with PD-L1 expression in multiple cancers suggests that the PD-1/PD-L1 pathway plays a critical role in tumor immune evasion and should be considered as an attractive target for therapeutic intervention.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Combination Treatments

The compositions and methods of the present disclosure may be used in the context of a number of therapeutic or prophylactic applications. In order to increase the effectiveness of a treatment with the compositions of the present disclosure, e.g., a PD-1/PD-L1 inhibitor selected and/or administered as a single agent, or to augment the protection of another therapy (second therapy), it may be desirable to combine these compositions and methods with one another, or with other agents and methods effective in the treatment, amelioration, or prevention of diseases and pathologic conditions, for example, neoplasia or tumors identified as MSI.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing a MSI tumor or cancer with, for example, PD-1/PD-L1 inhibitors) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

For example, MSI neoplasia or tumors described herein may be treated with therapeutic agents such as, for example, immunotherapeutic agents that act by effectively stimulating the immune response, e.g., PD-1/PD-L1 inhibitors (e.g., Pembrolizumab). Pembrolizumab is a humanized monoclonal antibody that blocks the interaction between PD-1 and its ligands, PD-L1 and PD-L2. Pembrolizumab is an IgG4 kappa immunoglobulin with an approximate molecular weight of 149 kDa. Pembrolizumab is believed to have a mechanism of action in which binding of the PD-1 ligands, PD-L1 and PD-L2, to the PD-1 receptor found on T cells, inhibits T cell proliferation and cytokine production. Upregulation of PD-1 ligands occurs in some tumors and signaling through this pathway can contribute to inhibition of active T-cell immune surveillance of tumors. Pembrolizumab binds to the PD-1 receptor and blocks its interaction with PD-L1 and PD-L2, releasing PD-1 pathway-mediated inhibition of the immune response, including the anti-tumor immune response. In syngeneic mouse tumor models, blocking PD-1 activity resulted in decreased tumor growth.

Programmed cell death 1 (PD-1) and programmed death ligand 1 (PD-L1) blockade as a potential form of cancer immunotherapy are based on the fact that activation of the PD-1/PD-L1 axis serves as a mechanism for tumor evasion of host tumor antigen-specific T-cell immunity. Accordingly, inhibition of PD-1/PDL-1 interaction (and corresponding downstream signaling events) strengthen tumor antigen-specific T-cell responses and corresponding tumor antigen-specific T-cell immunity. Other FDA approved PD-1/PD-L1 immunotherapeutic inhibitors include Nivolumab, which like Pembrolizumab, is a PD-1 inhibitor antibody, and Atezolizumab, Durvalumba, and Avelumab, which are all PD-L1 inhibitor antibodies.

In addition to immunotherapeutic treatments, the invention includes treatment with additional agents, either alone or in combination with the immunotherapeutic treatment (such as the anti-PD-1/PDL-1 therapeutic agent). Examples of such agents include chemotherapeutic agents including chemotherapeutic alkylating agents such as Cyclophosphamide. Mechlorethamine, Chlorambucil, Melphalan, Monofunctional alkylators, Dacarbazine, nitrosoureas, and Temozolomide (Oral dacarbazine), anthracyclines such as Daunorubicin, Doxorubicin, Epirubicin, Idarubicin, Mitoxantrone, Valrubicin, cytoskeletal disruptor agents (taxanes) such as Paclitaxel, Docetaxel, Abraxane and Taxotere; Epothilones; Histone deacetylase inhibitors such as Vorinostat and Romidepsin; topoisomerase I inhibitors such as Irinotecan and Topotecan; topoisomerase II inhibitors such as Etoposide, Teniposide, and Tafluposide; Kinase inhibitors such as Bortezomib, Erlotinib, Gefitinib, Imatinib, Vemurafenib, and Vismodegib; nucleotide analogs and precursor analog agents such as Azacitidine, Azathioprine, Capecitabine, Cytarabine, Doxiflundine, Fluorouracil, Gemcitabine, Hydroxyurea, Mercaptopurine, Methotrexate, and Troguanine (formerly Thioguanine); peptide antibiotics such as Bleomycin and Actinomycin; Platinum-based agents such as Carboplatin, Cisplatin, Oxaliplatin: Retinoids such as Retnoids, Tretinoin, Alitretinoin, Bexarotene; Vinca alkaloids and derivatives such as Vinblastine, Vincristine, Vindesine and Vinorelbine; as well as other chemotherapeutic agents including all-trans retinoic acid, Docetaxel, Doxifluridine, Epothilone, Fluorouracil, Methotrexate, and Pemetrexed.

A chemotherapeutic agents drugs for use with the invention include any chemical compound used in the treatment of a proliferative disorder. Chemotherapeutic agents include, but are not limited to, RAF inhibitors (e.g., BRAF inhibitors), MEK inhibitors, PI3K inhibitors and AKT inhibitors. Other chemotherapeutic agents include, without being limited to, the following classes of agents: nitrogen mustards, e.g., cyclophosphamide, trofosfamide, ifosfamide and chlorambucil; nitroso ureas. e.g., carmustine (BCNU), lomustine (CCNU), semustine (methyl CCNU) and nimustine (ACNU); ethylene imines and methyl-melamines, e.g., thiotepa, Colic acid analogs, e.g., methotrexate: pyrimidine analogs, e.g., 5-fluorouracil and cytarabine; purine analogs, e.g., mercaptopurine and azathioprine; vinca alkaloids. e.g., vinblastine, vincristine and vindesine; epipodophyllotoxins, e.g., etoposide and teniposide; antibiotics, e.g., dactinomycin, daunorubicin, doxorubicin, epirubicin, bleonycin a2, mitomycin c and mitoxantrone, estrogens, e.g., diethyl stilbestrol, gonadotropin-releasing hormone analogs, e.g., leuprolide, buserelin and goserelin; antiestrogens, e.g., tamoxifen and aminoglutethimide; androgens, e.g., testolactone and drostanolonpropnonate; platinates, e.g., cisplatin and carboplatin, and interferons, including interferon-alpha, beta and gamma.

Chemotherapeutic agents include, for example, RAF inhibitors (e.g. Vemurafenib or Dabrafenib), MEK inhibitors, PI3K inhibitors, or AKT inhibitors The RAF inhibitor is, for example, a BRAF inhibitor. The chemotherapeutic agents can be administered alone or in combination (e.g., RAF inhibitors with MEK inhibitors). The cancer is any cancer in which the tumor has a B-RAF activating mutation. For example the cancer is melanoma, colon cancer, lung cancer, brain cancer, hematologic cancers or thyroid cancer.

In addition, these modulatory agents can also be administered in combination therapy with, e.g., chemotherapeutic agents, hormones, antiangiogens, radiolabeled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy.

The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer (e.g., a hematological cancer, such as DLBCL), being treated, the combined use of immunotherapeutic agent (e.g., anti-PD1/PDL1), the extent of the disease and other factors familiar to the physician of skill in the art and can be determined by the physician.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the compounds (e.g., FDA-approved compounds) of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, e.g. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with a PD-1/PD-L1 inhibitor, etc.) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 sg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span®) 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., a BCL2 inhibitor, PI3K inhibitor, BCR/TLR signaling inhibitor, JAK/STAT inhibitor, etc.) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions.

Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

FDA-approved drugs provided herein are typically formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., a PD-1/PD-L1 inhibitor, etc.) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

The FDA-approved drug or other therapy is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., a PD-1/PD-L1 inhibitor, etc.) described herein. In certain embodiments, a dose described herein includes independently between 1 mg and 3 mg, inclusive, of an agent (e.g., a PD-1/PD-L1 inhibitor, etc.) described herein. In certain embodiments, a dose described herein includes independently between 3 mg and 10 mg, inclusive, of an agent (e.g., a PD-1/PD-L1 inhibitor, etc.) described herein. In certain embodiments, a dose described herein includes independently between 10 mg and 30 mg, inclusive, of an agent (e.g., a PD-1/PD-L1 inhibitor, etc.) described herein. In certain embodiments, a dose described herein includes independently between 30 mg and 100 mg, inclusive, of an agent (e.g., a PD-1/PD-L1 inhibitor, etc.) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., a PD-1/PD-L1 inhibitor, etc.) or composition, as described herein, can be administered in combination with one or more additional pharmaceutical agents (e.g., therapeutically and/or prophylactically active agents), which are different from the agent or composition and may be useful as, e.g., combination therapies. The agents or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk of developing a disease in a subject in need thereof, in inhibiting the replication of a virus, in killing a virus, etc. in a subject or cell. In certain embodiments, a pharmaceutical composition described herein including an agent (e.g., a PD-1/PD-L1 inhibitor, etc.) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an antioxidant, an anti-inflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, chemotherapeutic agents, other epigenetic modifier inhibitors, etc., other anti-cancer agents, immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., a PD-1/PD-L1 inhibitor, etc.) of this disclosure and/or may contain agents (e.g., oligonucleotide primers, probes, etc.) for identifying a cancer or subject as possessing one or more variant sequences. In some embodiments, the kits further include instructions for use in accordance with the methods of this disclosure. In some embodiments, these instructions comprise a description of administration of the agent to treat or diagnose, e.g., a neoplasia or tumor having MSI, according to any of the methods of this disclosure. In some embodiments, the instructions comprise a description of how to detect a MSI class of cancer, for example in an individual, in a tissue sample, or in a cell.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a class of MSI cancer, in a subject Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is a PD-1/PD-L1 inhibitor, an epigenetic modifier, an epigenetic modifier inhibitor, etc. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Microsatellite (MS) Display Significant Rates of Somatic Indels

The present disclosure provides the ability to classify neoplasia or tumors as microsatellite instable (MSI) or microsatellite stable (MSS) based on obtaining and analyzing low coverage whole genome sequencing data from the neoplasia or tumors. Initially, a training set of about 1,000 30× whole genome sequencing (WGS) samples from the TCGA was used and tested on 223 low pass WGS samples.

MSMuTect4 (Maruvka et al. (2017) Analysis of somatic microsatellite indels identifies driver events in human tumors. Nat Biotechnol 35(10):951-959) was used to detect somatic MS indels from sequencing data from about 1,000 WGS tumor normal pairs from colon adenocarcinoma (COAD), stomach adenocarcinoma (STAD), and uterine corpus endometrial carcinoma (UCEC), which had their MSI status classified by the Bethesda protocol. This analysis identified somatic indels in the approximately 23,000,000 extent MS loci in the whole genome (Supplementary Table S5). Even tumors with a very low indel rate were found to have about a few hundred (e.g., 100-200, 100-300, 100-400, 100-500, 100-600, 100-700, 100-800, 100-900, and the like) indels.

Example 2: MS Indel Signatures Accurately Identify Neoplasia or Tumors Having MS Instability (MSI)

Figure 20:
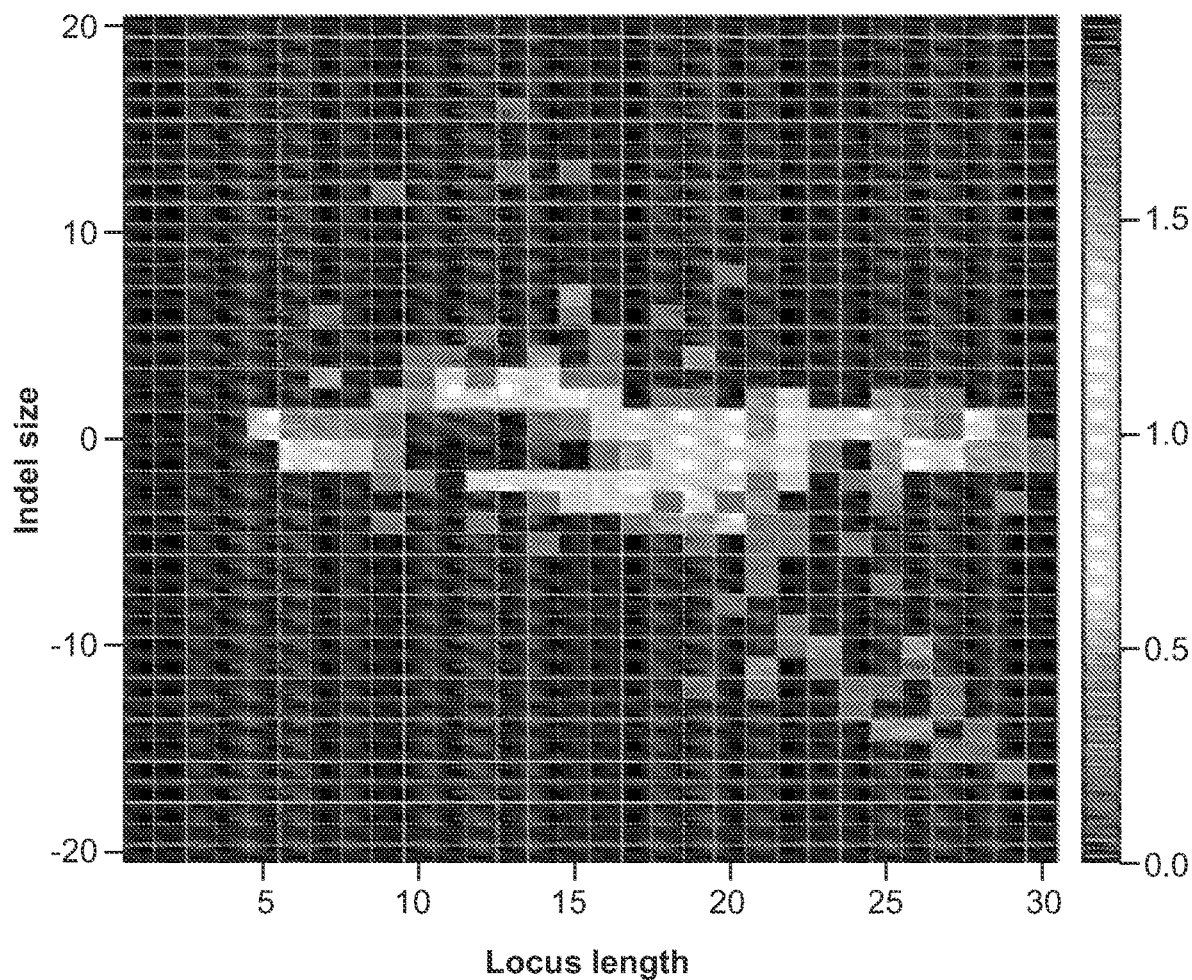
FIG. 20 is a plot showing a typical distribution of microsatellite (MS) indels in a microsatellite stable (MSS) sample. X-axis presents the length of the MS locus (i.e. the number of repeats), and the y-axis present the size of the indel, positive for insertions and negative for deletions. The color of each box is the log 10 scale of the number of MS indels in that group (loci length of indel size).
Figure 21:
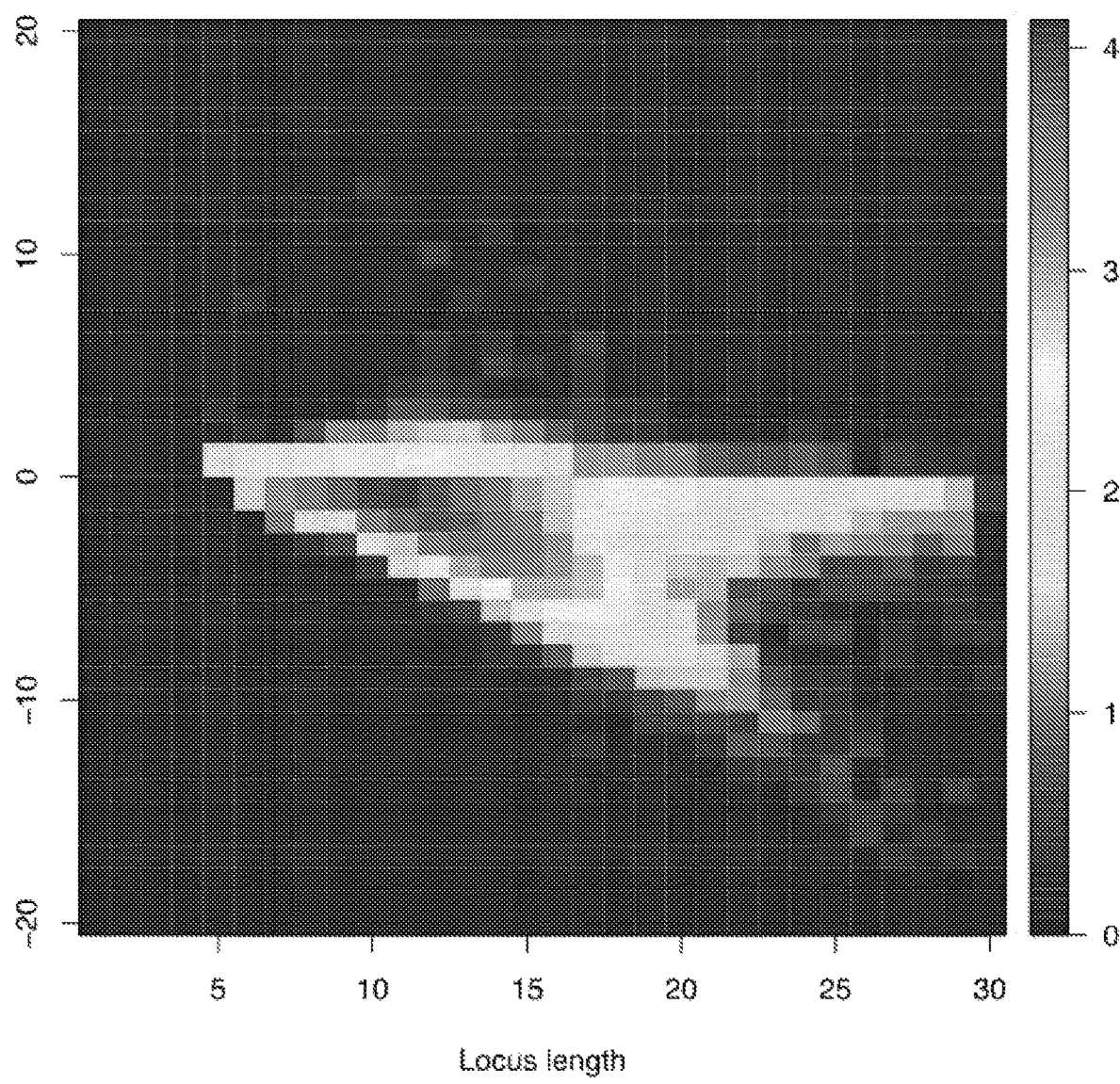
FIG. 21 is a plot showing a typical distribution of MS indels in a microsatellite instability (MSI) sample. X-axis presents the length of the MS locus (i.e. the number of repeats), and the y-axis present the size of the indel, positive for insertions and negative for deletions. The color of each box is the log 10 scale of the number of MS indels in that group (loci length of indel size).

The MSMuTect4 analysis revealed that MSS neoplasia or tumors have a strong tendency for the relative number of deletions to be approximately the same as the relative number of insertions, as shown in FIG. 20. Surprisingly, it was discovered that MSI neoplasia or tumors have a strong tendency for the relative number of deletions to be higher than the relative number of insertions, as shown in FIG. 21. In this regard, the present disclosure provides MS indel signatures that accurately classify neoplasia or tumor as MSI or MSS.

MS indel signature is a better measure for MSI than just the raw count of MS indels. Without being bound by theory, it is believed that the reason for this is that other processes (e.g., homologous recombination repair) may also generate many indels, some of which are likely to fall in MS loci. Based on that observation, the present disclosure developed a score that recapitulates the tendency towards deletion without the need to call indels in any specific MS locus.

Example 3: Methods and Materials

For each of the 23,000,000 MS loci, the number of sequence reads that supports less repeats than the references and the number of sequence reads that support more repeats than the reference was counted. All the reads that differ from the reference in the same amount together with a different weight to different loci were then aggregated. A score was then defined for each sample as the ratio between the number of reads that were two or more bases shorter than the reference sequence and the number of reads that were two or more bases longer than the reference. The threshold between MSI and MSS was log 10(score)=0.3.

Figure 22:
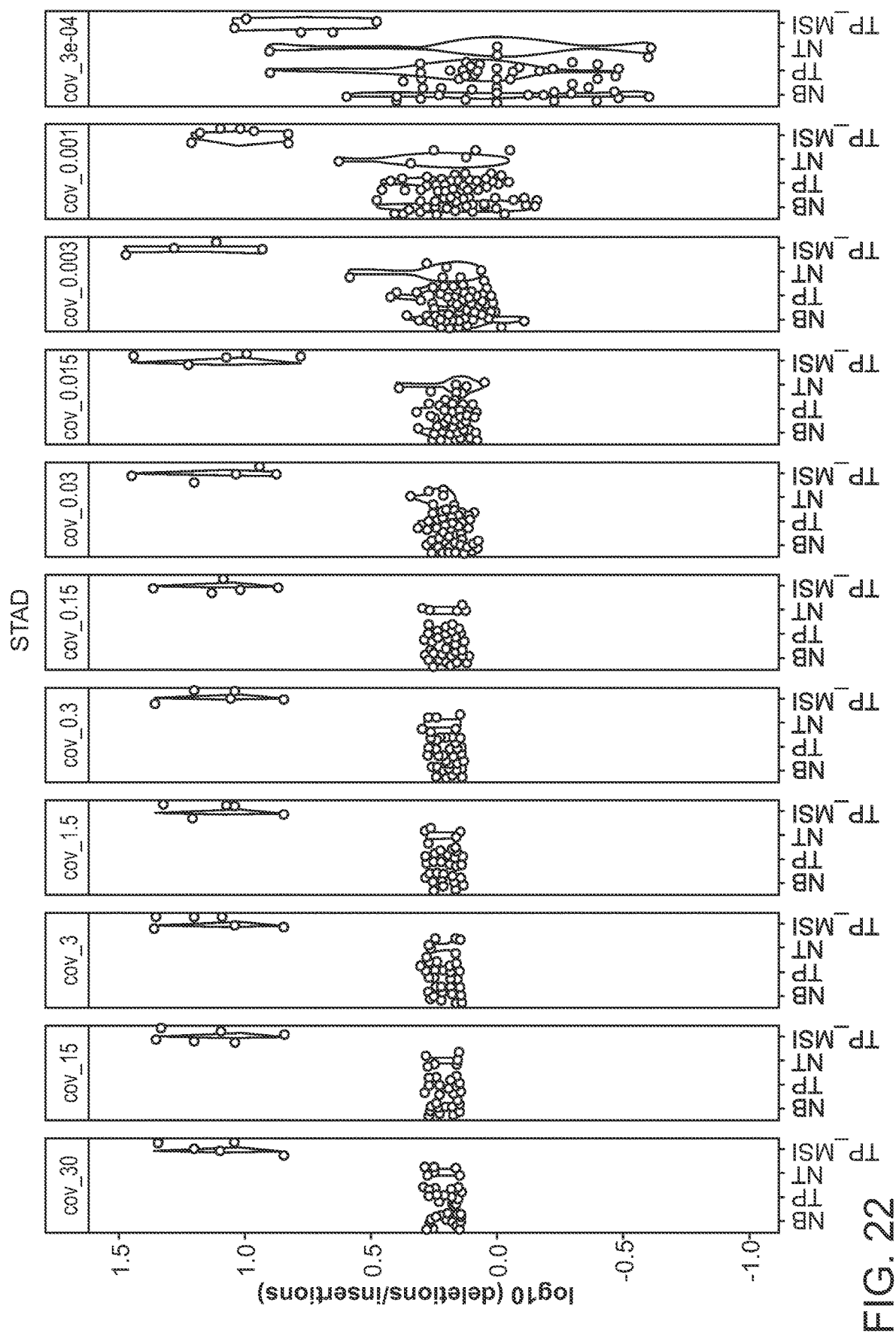
FIG. 22 shows a series of panels depicting MSIClass score for STAD TCGA WGS samples for different coverage. The samples are classified as NB—normal blood, NT—normal tissue, TP—tumor primary, and TP—MSI tumor primary MSI. The y-axis is the log 10 of the MSIness score. Each panel was generated by a different coverage as noted on top of it.
Figure 23:
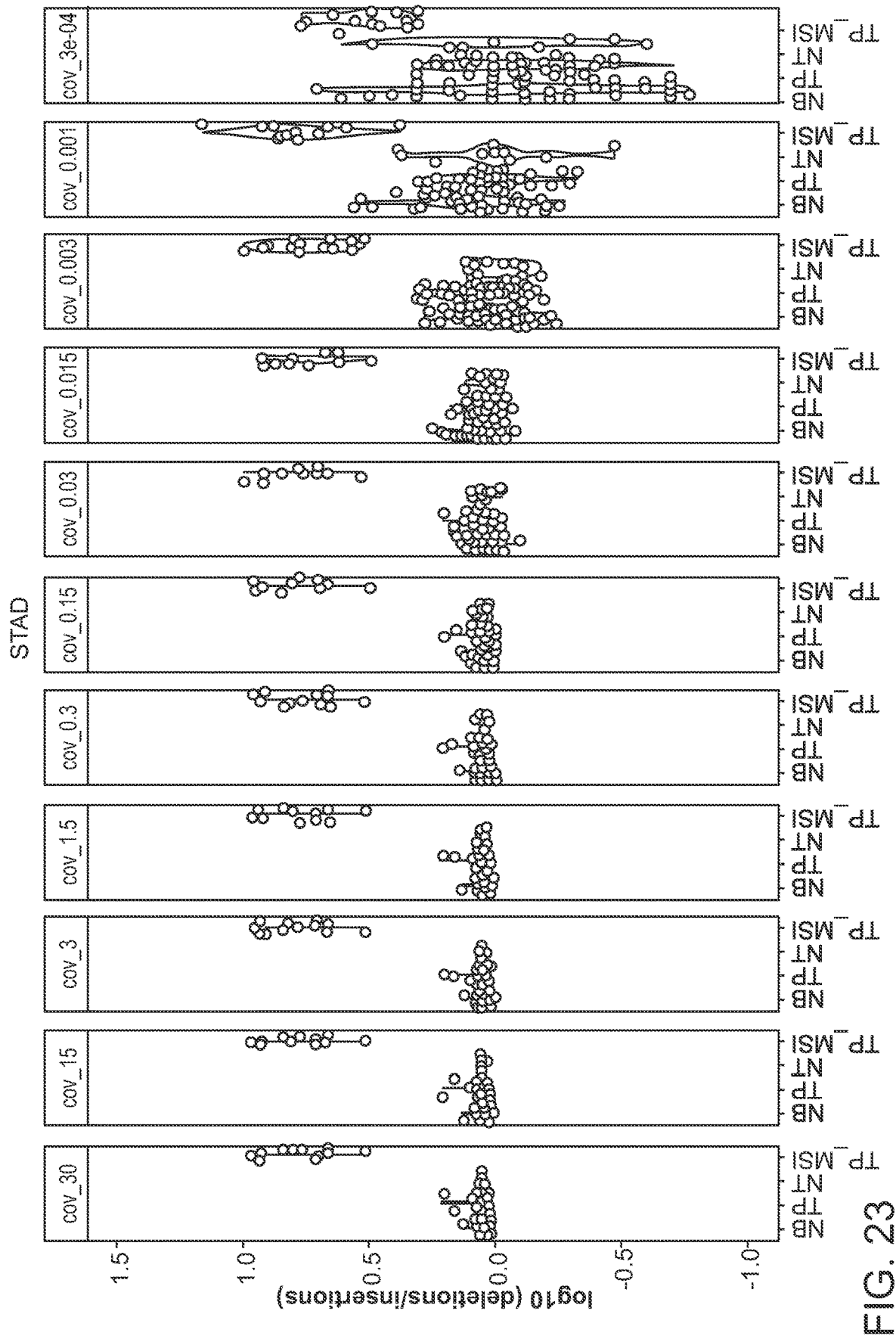
FIG. 23 shows a series of panels depicting MSIClass score for COAD TCGA WGS samples for different coverage. The legend is the same as that for FIG. 22.
Figure 24:
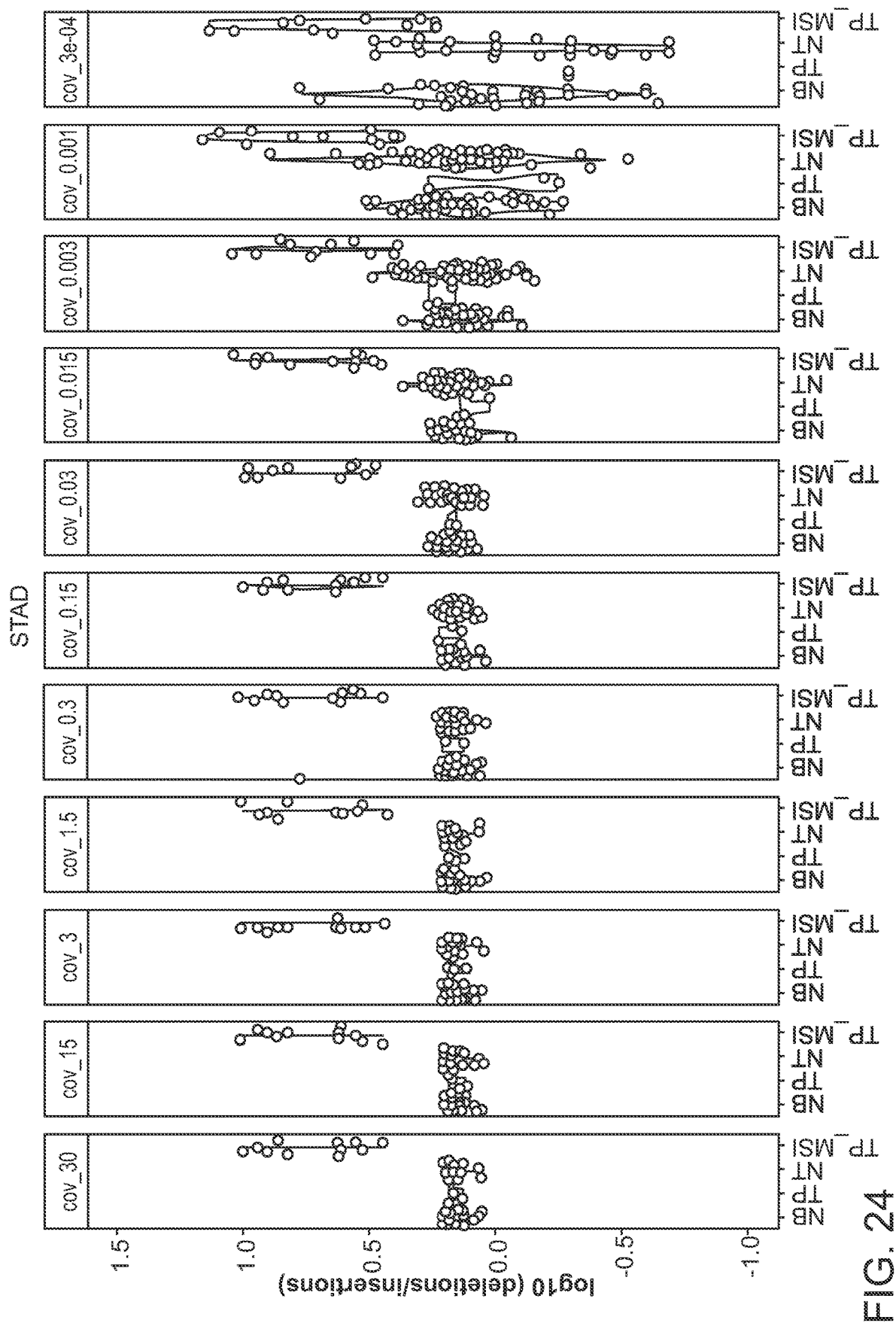
FIG. 24 shows a series of panels depicting MSIClass scores for STAD TCGA WGS samples for different coverage. The legend is the same as that for FIG. 22.

By analyzing approximately 1,000 TCGA WGS samples, it was found that the score value perfectly classified the 48 MSI tumors as MSI, which is more than the 7 Bethesda protocols loci. As shown in FIGS. 22-24, even with sub-sampling reads and WGS coverage of only about 0.01×, the techniques herein perfectly classified tumors as MSI.

TCGA low PASS whole genome: As part of the TCGA, about 20% of the samples were sequenced by WGS 5× coverage. The techniques herein were applied to those samples and it was found that the score value perfectly classified MSI tumors within the TCGA low pass WGS.

MSI-wide loci classification algorithm: For every repeat motif (e.g., A, C, AC, AG, GCT, etc.), the sequencing reads were aggregated from loci with the same number of repeats into a single combined histogram, as follows. For all reads, the difference in the number of repeated motifs between a given read and its counterpart within a reference genome (difference in repeated motifs ranged from −10 to +10, with each number within this range considered a separate event) was first determined. For example, a read containing a deletion of two repeated motifs was assigned a value of "−2," a read containing an insertion of one motif was assigned a value of "1," and a read without any insertions or deletions was assigned a value of "0." This data was then aggregated by counting the total number of reads that supported each repeated-motif event. This procedure generated a set of histograms for every patient: one for every motif and every number of repeats in the reference genome. It is important to note that these histograms contain all three types of events (germline variability, somatic MS indels, and noise) that may contribute to detecting a difference from the reference genome.

As discussed herein, the somatic MS indels detected in MSI cases have the unique feature of being biased towards deletion events. Therefore, a scoring method was defined that captured this unique behavior:

$$S = \log_{10}\left(\left|\frac{\alpha_i \cdot N_i^{del\_j}}{N_i^{ref}}\right|\right)$$

where S is the score, i is the MS length, del_j is the size of the deletion, and N_i the number of reads of the specific motif length.

Figure 25:
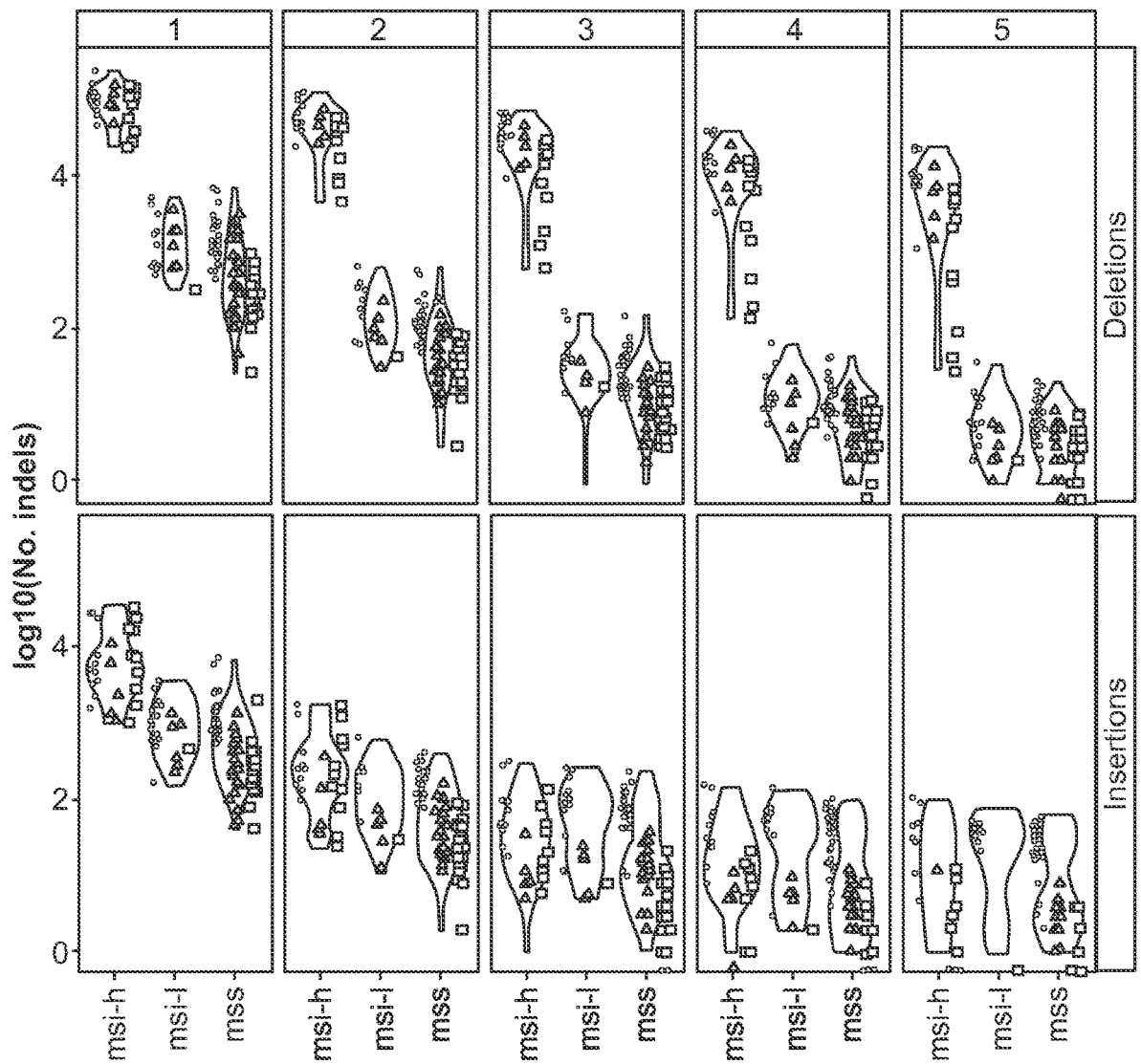
FIG. 25 shows a series of panes depicting Number of MS indels for each case divided by event type (deletions vs insertions) and size of the change (1-5 bases) for the A motif.

According to the techniques herein, it was found that the fraction of reads with 2-bp deletions within 8-13-bp-long loci was the best classifier of MSI vs MSS samples (see e.g., FIG. 25). Therefore, in exemplary embodiments the following variable values are used: α_i=1 for 8≤i≤13, and α_i=0 otherwise. In exemplary embodiments, a value of S>−2.2 was determined to be the threshold for MSI cases.

One of skill in the art will appreciate that each sequencing platform may have its own level of background noise and thus contribute different fractions of reads presenting non-reference numbers of reads compared to other platforms. Therefore, the baseline score may differ among the different platforms, and the exact value of the threshold should be determined by the user. That said, tests of a few different facilities and a few different Illumina sequencing machines indicated that the differences in baseline score were minor and affected only small fraction (~1-2%) of cases.

Residual data from whole exome sequencing and whole panel sequencing: On of skill in the art will appreciate that there are many applications of whole exome and whole panel sequencing that generate significant amounts of unused residual sequence data. For example, there are many clinical institutions that sequence only a subset of genes in what is called clinical panel. The technology that targets these specific regions of the genome is not perfect and still some of the sequenced reads come from outside of the desired enriched genes. Due to the fact that typically the clinical panels sequence to a larger depth >500× coverage, there are many residual reads that come from all around the genome. These residual reads can replace the whole genome low pass sequencing as the data needed for the MSI classification. While there may be some bias in the residual reads and the genome will not be covered equally, this data may still hold similar information for use in detecting MSI.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

REFERENCES

1. Ellegren, H. Microsatellites: simple sequences with complex evolution. Nat. Rev. Genet. 5, 435-445 (2004).
2. Sun, J. X. et al. A direct characterization of human mutation based on microsatellites. Nat. Genet 44, 1161-1165 (2012).
3. Pearson, C. E., Edamura, K. N. & Cleary, J. D. Repeat instability: mechanisms of dynamic mutations. Nat. Rev. Genet. 6, 729-742(2005).
4. Kennedy, L. et al. Dramatic tissue-specific mutation length increases are an early molecular event in Huntington disease pathogenesis. Hum. Mol. Genet. 12, 3359-3367 (2003).
5. Willemsen, R., Levenga, J. & Oostra, B. A. CGG repeat in the FMR1 gene: size matters. Clin. Genet. 80, 214-225 (2011).
6. Nik-Zainal, S. et al. Landscape of somatic mutations in 560 breast cancer whole-genome sequences. Nature 534, 47-54 (2016).
7. Giannakis, M. et al. RNF43 is frequently mutated in colorectal and endometrial cancers. Nat. Genet 46, 1264-1266 (2014).
8. Vilar, E. & Gruber, S. B. Microsatellite instability in colorectal cancer—the stable evidence. Nat. Rev. Clin. Oncol. 7, 153-162 (2010).
9. Stadler, Z. K. Diagnosis and management of DNA mismatch repair-deficient colorectal cancer. Hematol. Oncol. Clin. North Am. 29, 29-41 (2015).
10. Le, D. T. et al. PD-1 Blockade in Tumors with Mismatch-Repair Deficiency. N. Engl. J. Med. 372, 2509-2520 (2015).
11. Watkins, J. C. et al. Universal Screening for Mismatch-Repair Deficiency in Endometrial Cancers to Identify Patients With Lynch Syndrome and Lynch-like Syndrome. Int. J. Gynecol. Pathol. Off. J. Int. Soc. Gynecol. Pathol. (2016). doi:10.1097/PGP.0000000000000312
12. Umar, A. et al. Revised Bethesda Guidelines for Hereditary Nonpolyposis Colorectal Cancer (Lynch Syndrome) and Microsatellite Instability. J. Natl. Cancer Inst. 96, 261-268 (2004).
13. Hause, R. J., Pritchard, C. C., Shendure, J. & Salipante, S. J. Classification and characterization of microsatellite instability across 18 cancer types. Nat. Med. 22, 1342-1350 (2016).
14. Lawrence, M. S. et al. Mutational heterogeneity in cancer and the search for new cancer-associated genes. Nature 499, 214-218 (2013).
15. Lawrence, M. S. et al. Discovery and saturation analysis of cancer genes across 21 tumour types. Nature 505, 495-501 (2014).
16. Mayer, C., Leese, F. & Tollrian, R. Genome-wide analysis of tandem repeats in *Daphnia pulex*—a comparative approach. BMC Genomics 11, 277 (2010).
17. Cibulskis, K. et al. Sensitive detection of somatic point mutations in impure and heterogeneous cancer samples. Nat. Biotechnol. 31, 213-219 (2013).
18. The 1000 Genomes Project Consortium. A global reference for human genetic variation. Nature 526, 68-74 (2015).

19. Tokunaga, E. et al. Frequency of microsatellite instability in Breast cancer determined by high-resolution fluorescent microsatellite analysis. Oncology 59, 44-49 (2000).
20. Larson, A. A. et al. Analysis of replication error (RER+) phenotypes in cervical carcinoma. Cancer Res. 56, 1426-1431 (1996).
21. Taylor, N. P. et al. Defective DNA mismatch repair and XRCC2 mutation in uterine carcinosarcomas. Gynecol. Oncol. 100, 107-110 (2006).
22. Medina-Arana, V. et al. Adrenocortical carcinoma, an unusual extracolonic tumor associated with Lynch II syndrome. Fam. Cancer 10, 265-271 (2011).
23. Supek, F. & Lehner, B. Differential DNA mismatch repair underlies mutation rate variation across the human genome. Nature 521, 81-84 (2015).43094
24. Liu, L., De, S. & Michor, F. DNA replication timing and higher-order nuclear organization determine single-nucleotide substitution patterns in cancer genomes. Nat. Commun. 4, 1502 (2013).
25. Kim, T.-M., Laird, P. W. & Park, P. J. The landscape of microsatellite instability in colorectal and endometrial cancer genomes. Cell 155, 858-868 (2013).
26. Knudson, A. G. Mutation and Cancer Statistical Study of Retinoblastoma. Proc. Natl. Acad. Sci. 68, 820-823 (1971).
27. Vogelstein, B. et al. Cancer Genome Landscapes. Science 339, 1546-1558 (2013).
28. Network, T. C. G. A. Comprehensive molecular characterization of human colon and rectal cancer. Nature 487, 330-337 (2012).
29. Cederquist, K. Genetic and epidemiological studies of hereditary colorectal cancer. (2005).
30. Biswas, S. et al. Mutational inactivation of TGFBR2 in microsatellite unstable colon cancer arises from the cooperation of genomic instability and the clonal outgrowth of transforming growth factor 0 resistant cells. Genes. Chromosomes Cancer 47, 95-106 (2008).
31. Network, T. C. G. A. R. Integrated genomic characterization of endometrial carcinoma.
Nature 497, 67-73 (2013).
32. Maquat, L. E. Nonsense-mediated mRNA decay: splicing, translation and mRNP dynamics. Nat. Rev. Mol. Cell Biol. 5, 89-99 (2004).
33. Lewis, B. P., Green, R. E. & Brenner, S. E. Evidence for the widespread coupling of alternative splicing and nonsense-mediated mRNA decay in humans. Proc. Natl. Acad. Sci. 100, 189-192 (2003).
34. Zhang, J., Sun, X., Qian, Y. & Maquat, L. E. Intron function in the nonsense-mediated decay of beta-globin mRNA: indications that pre-mRNA splicing in the nucleus can influence mRNA translation in the cytoplasm. RNA N. Y. N 4, 801-815 (1998).
35. Silva, A. L. et al. The canonical UPF1-dependent nonsense-mediated mRNA decay is inhibited in transcripts carrying a short open reading frame independent of sequence context.
RNA 12, 2160-2170 (2006).
36. Deacu, E. et al. Activin Type II Receptor Restoration in ACVR2-Deficient Colon Cancer Cells Induces Transforming Growth Factor-0 Response Pathway Genes. Cancer Res. 64, 7690-7696 (2004).
37. Ballikaya, S. Activin Receptor Type 2 A (ACVR2A)-dependent Proteomic and Glycomic Alterations in a Microsatellite Unstable (MSI) Colorectal Cancer Cell Line Model System. (2014).
38. Niu, L. et al. RNF43 Inhibits Cancer Cell Proliferation and Could be a Potential Prognostic Factor for Human Gastric Carcinoma. Cell. Physiol. Biochem. Int. J. Exp. Cell. Physiol. Biochem. Pharmacol. 36, 1835-1846 (2015).
39. The Cancer Genome Atlas Research Network. Comprehensive molecular characterization of gastric adenocarcinoma. Nature 513, 202-209 (2014).
40. Jo, Y. S. et al. Frequent frameshift mutations in 2 mononucleotide repeats of RNF43 gene and its regional heterogeneity in gastric and colorectal cancers. Hum. Pathol. 46, 1640-1646 (2015).
41. Duraturo, F. et al. Association of low-risk MSH3 and MSH2 variant alleles with Lynch syndrome: probability of synergistic effects. Int. J. Cancer 129, 1643-1650 (2011).
42. Wind, N. de et al. HNPCC-like cancer predisposition in mice through simultaneous loss of Msh3 and Msh6 mismatch-repair protein functions. Nat. Genet. 23, 359-362 (1999).
43. Mzoughi, S., Tan, Y. X., Low, D. & Guccione, E. The role of PRDMs in cancer: one family, two sides. Curr. Opin. Genet. Dev. 36, 83-91 (2016).
44. Ge. P., Yu, X., Wang, Z.-C. & Lin, J. Aberrant Methylation of the lp36 Tumor Suppressor Gene RIZ1 in Renal Cell Carcinoma. Asian Pac. J. Cancer Prev. 16, 4071-4075 (2015).
45. Dong, S.-W. et al., Alteration in gene expression profile and oncogenicity of esophageal squamous cell carcinoma by RIZ1 upregulation. World J Gastroenterol 19, 6170-7 (2013).
46. Liu, Z. Y. et al. Retinoblastoma protein-interacting zinc-finger gene 1 (RIZ1) dysregulation in human malignant meningiomas. Oncogene 32, 1216-1222 (2013).
47. Warzecha, C. C., Sato, T. K., Nabet, B., Hogenesch, J. B. & Carstens, R. P. ESRP1 and ESRP2 are epithelial cell-type-specific regulators of FGFR2 splicing. Mol. Cell 33, 591-601 (2009).
48. Ueda, J. et al. Epithelial splicing regulatory protein 1 is a favorable prognostic factor in pancreatic cancer that attenuates pancreatic metastases. Oncogene 33, 4485-4495 (2014).
49. Gordon, G. M., Lambert, Q. T., Daniel, K. G. & Reuther, G. W. Transforming JAK1 mutations exhibit differential signalling, FERM domain requirements and growth responses to interferon-γ. Biochem. J. 432, 255-265 (2010).
50. Ren, Y. et al. JAK1 truncating mutations in gynecologic cancer define new role of cancer-associated protein tyrosine kinase aberrations. Sci. Rep. 3, (2013).
51. Einav, U. et al. Gene expression analysis reveals a strong signature of an interferon-induced pathway in childhood lymphoblastic leukemia as well as in breast and ovarian cancer. Oncogene 24, 6367-6375 (2005).
52. Caspi, E. & Rosin-Arbesfeld, R. A novel functional screen in human cells identifies MOCA as a negative regulator of Wnt signaling. Mol. Biol. Cell 19, 4660-4674 (2008).
53. Taupin, D. et al. A deleterious RNF43 germline mutation in a severely affected serrated polyposis kindred. Hum. Genome Var. 2, 15013 (2015).
54. Howitt, B. E. et al. Association of Polymerase e-Mutated and Microsatellite-Instable Endometrial Cancers With Neoantigen Load, Number of Tumor-Infiltrating Lymphocytes, and Expression of PD-1 and PD-L1. JAMA Oncol. 1, 1319-1323 (2015).

55. Lee, V., Murphy, A., Le, D. T. & Diaz, L. A. Mismatch Repair Deficiency and Response to Immune Checkpoint Blockade. The Oncologist 21, 1200-1211 (2016).
56. Lujan, S. A., Clark, A. B. & Kunkel, T. A. Differences in genome-wide repeat sequence instability conferred by proofreading and mismatch repair defects. Nucleic Acids Res. 43, 4067-4074 (2015).
57. Vinagre, J. et al. Frequency of TERT promoter mutations in human cancers. Nat. Commun. 4, 2185 (2013).
58. The Cancer Genome Atlas—Data Portal. Available at: https://tcga-data.nci.nih.gov/docs/publications/tcgai. (Accessed: 10th October 2016)
59. Ramos, A. H. et al. Oncotator: cancer variant annotation tool. Hum. Mutat. 36, E2423-E2429 (2015).
60. Gymrek, M., Golan, D., Rosset, S. & Erlich, Y. lobSTR: a short tandem repeat profiler for personal genomes. Genome Res. 22, 1154-1162 (2012).
61. Langmead, B. & Salzberg, S. L. Fast gapped-read alignment with Bowtie 2. Nat. Methods 9, 357-359 (2012).
62. Cibulskis, K. et al. Sensitive detection of somatic point mutations in impure and heterogeneous cancer samples. Nat. Biotechnol. 31, 213-219 (2013).
63. Alexandrov, L. B. et al. Signatures of mutational processes in human cancer. Nature 500, 415-421 (2013).
64. Futreal, P. A. et al. A census of human cancer genes. Nat. Rev. Cancer 4, 177-183 (2004).

Having thus described in detail preferred embodiments of the present disclosure, it is to be understood that the disclosure defined by the above paragraphs is not to be limited to particular details set forth in the above description as many apparent variations thereof are possible without departing from the spirit or scope of the present disclosure.

What is claimed is:
1. A method for selecting a treatment for a subject having or at risk of having a microsatellite instable (MSI) cancer, comprising:
(a) procuring a neoplasia or tumor sample from the subject having or at risk of having MSI cancer;
(b) obtaining whole genome sequence (WGS) data from the neoplasia or tumor sample;
(c) identifying a plurality of microsatellite (MS) loci within the WGS data;
(d) identifying, for each of the plurality of MS loci, one or more aberrant MS loci containing two or more deleted base pairs relative to one or more reference sequences corresponding to the one or more aberrant MS loci;
(e) counting a number of the one or more identified aberrant MS loci to create a sample size count variable;
(f) counting a number of times each of the one or more aberrant MS loci contain two or more deleted base pairs that are identical to create a deletion count variable;
(g) calculating a score for the neoplasia or tumor sample based on the ratio of the deletion count variable to the sample size count variable;
(h) classifying the neoplasia or tumor sample as MSI when the score is greater than a threshold value; and
(i) selecting, based on the score being greater than the threshold value, a treatment for the subject comprising a therapeutic agent appropriate for the treatment of a MSI neoplasia or tumor.
2. The method of claim 1, wherein:
obtaining step (a) further comprises preparing genomic DNA from the neoplasia or tumor sample;
the obtaining step (b) comprises sequencing 1 ng-1 mg of prepared genomic DNA;
the obtaining step (b) comprises sequencing at least 10 ng-1 mg of prepared genomic DNA;

SEQUENCE LISTING

<160> NUMBER OF SEQ ID NOS: 3

<210> SEQ ID NO 1
<211> LENGTH: 10
<212> TYPE: DNA
<213> ORGANISM: Homo sapiens

<400> SEQUENCE: 1
acacacacac                                                         10

<210> SEQ ID NO 2
<211> LENGTH: 25
<212> TYPE: DNA
<213> ORGANISM: Homo sapiens

<400> SEQUENCE: 2
gtcaaaaaaa acaaaaaaaa aatcc                                        25

<210> SEQ ID NO 3
<211> LENGTH: 10
<212> TYPE: DNA
<213> ORGANISM: Homo sapiens

<400> SEQUENCE: 3 cccccccccc                                                         10 the WGS data is residual sequence data, optionally wherein the residual sequence data is whole exome sequencing data or whole panel sequencing data;

the predetermined length is about 5 to about 20 base pairs;

the predetermined length is about 5 to about 15 base pairs;

the predetermined length is about 8 to about 13 base pairs;

the two or more deleted base pairs are selected from the group consisting of A, C, AC, AG, and GCT;

the one or more reference sequences are obtained from non-neoplasia or non-tumor samples from the subject;

calculating step (g) or (f) is based on the following algorithm:

$$S = \log_{10}\left(\left|\frac{a_i \cdot N_i^{del\_j}}{N_i^{ref}}\right|\right),$$

wherein S is the score, i is the MS length, del_j is the size of the deletion, and N_i the number of MS loci of the predetermined length;

obtaining step (b) comprises use of a technology selected from the group consisting of targeted hybrid capture, an amplicon-based sequencing technology, a non-targeted sequencing technology, and a next-generation sequencing (NGS) technology; and/or the classifying step does not require comparing the neoplasia or tumor sample from the subject to a type matched normal sample.

3. The method of claim 1, wherein:

the WGS data or WGS dataset is obtained at about 60× to about 0.001× coverage;

the WGS data or WGS dataset is obtained at about 5× to about 0.01× coverage;

the WGS data or WGS dataset is obtained at about 1× to about 0.01× coverage;

the WGS data or WGS dataset is obtained at about 0.001× coverage;

the WGS data or WGS dataset is obtained at about 0.01×, 0.015×, 0.02×, 0.025×, 0.03×, 0.035×, 0.04×, 0.045×, 0.05×, 0.055×, 0.06×, 0.065×, 0.07×, 0.075×, 0.08×, 0.085×, 0.09×, or 0.1× coverage; and/or the WGS data or WGS dataset is obtained at about 0.1×, 0.2×, 0.3×, 0.4×, 0.5×, 0.6×, 0.7×, 0.8×, 0.9×, or 1.0× coverage.

4. A method selected from the group consisting of:

A method for treating a subject having or at risk of having a microsatellite instable (MSI) cancer, comprising:

(a) procuring a neoplasia or tumor sample from the subject having or at risk of having MSI cancer;

(b) obtaining whole genome sequence (WGS) data from the neoplasia or tumor sample;

(c) identifying a plurality of microsatellite (MS) loci within the WGS data;

(d) identifying, for each of the plurality of MS loci, one or more aberrant MS loci containing two or more deleted base pairs relative to one or more reference sequences corresponding to the one or more aberrant MS loci;

(e) counting a number of the one or more identified aberrant MS loci to create a sample size count variable;

(f) counting a number of times each of the one or more aberrant MS loci contain two or more deleted base pairs that are identical to create a deletion count variable;

(g) calculating a score for the neoplasia or tumor sample based on the ratio of the deletion count variable to the sample size count variable;

(h) classifying the neoplasia or tumor sample as MSI when the score is greater than a threshold value; and (i) administering, based on the score being greater than the threshold value, a therapeutic agent appropriate for the treatment of a MSI neoplasia or tumor;

A method for identifying a subject as having a microsatellite instable (MSI) cancer, comprising:

(a) procuring a neoplasia or tumor sample from the subject having or at risk of having MSI cancer;

(b) obtaining whole genome sequence (WGS) data from the neoplasia or tumor sample;

(c) identifying a plurality of microsatellite (MS) loci within the WGS data;

(d) identifying, for each of the plurality of MS loci, one or more aberrant MS loci containing two or more deleted base pairs relative to one or more reference sequences corresponding to the one or more aberrant MS loci;

(e) counting a number of the one or more identified aberrant MS loci to create a sample size count variable;

(f) counting a number of times each of the one or more aberrant MS loci contain two or more deleted base pairs that are identical to create a deletion count variable;

(g) calculating a score for the neoplasia or tumor sample based on the ratio of the deletion count variable to the sample size count variable;

(h) classifying the neoplasia or tumor sample as MSI when the score is greater than a threshold value; and (i) identifying, based on the score being greater than the threshold value, the subject as having a MSI neoplasia or tumor;

A method for treating a subject having or at risk of having a microsatellite instable (MSI) cancer, comprising:

(a) obtaining a neoplasia or tumor sample from the subject having or at risk of having MSI cancer;

(b) obtaining whole genome sequence (WGS) data from the neoplasia or tumor sample;

(c) detecting one or more sequence reads within the WGS data spanning a plurality of microsatellite (MS) loci of a predetermined length;

(d) identifying one or more aberrant sequence reads within the one or more sequence reads spanning the plurality of MS loci that contain deleted base pairs or inserted base pairs relative to a plurality of reference sequences corresponding to the one or more aberrant sequence reads;

(e) aggregating the identified one or more aberrant sequence reads for each the MS loci into groups that contain the same number of deleted base pairs or inserted base pairs for each of the plurality of MS loci;

(f) calculating a score for the neoplasia or tumor sample based on the ratio of deleted base pairs to inserted base pairs;

(g) classifying the neoplasia or tumor sample as MSI when the score is greater than a threshold value; and (h) administering, based on the score being greater than the threshold value, a therapeutic agent appropriate for the treatment of a MSI neoplasia or tumor;

A method for identifying a subject as having a microsatellite instable (MSI) cancer, comprising:

(a) obtaining a neoplasia or tumor sample from the subject having or at risk of having MSI cancer;

(b) obtaining whole genome sequence (WGS) data from the neoplasia or tumor sample;

(c) detecting one or more sequence reads within the WGS data spanning a plurality of microsatellite (MS) loci of a predetermined length;

(d) identifying one or more aberrant sequence reads within the one or more sequence reads spanning the plurality of MS loci that contain deleted base pairs or inserted base pairs relative to a plurality of reference sequences corresponding to the one or more aberrant sequence reads;

(e) aggregating the identified one or more aberrant sequence reads for each the MS loci into groups that contain the same number of deleted base pairs or inserted base pairs for each of the plurality of MS loci;

(f) calculating a score for the neoplasia or tumor sample based on the ratio of deleted base pairs to inserted base pairs;

(g) classifying the neoplasia or tumor sample as MSI when the score is greater than a threshold value; and (h) identifying, based on the score being greater than the threshold value, the subject as having a MSI neoplasia or tumor;

A method comprising:

identifying, at a processor of a computing device configured to analyze high throughput sequencing data, a plurality of microsatellite (MS) loci within a whole genome sequence (WGS) dataset from a neoplasia or a tumor;

identifying, at the processor, one or more aberrant MS loci within the plurality of MS loci that contain two or more deleted base pairs relative to one or more reference sequences corresponding to the one or more aberrant MS loci;

incrementing a sample size count variable for each of the identified one or more aberrant MS loci;

identifying, at the processor, one or more instances where the one or more aberrant MS loci contain two or more deleted base pairs that are identical;

incrementing a deletion count variable for each of the identified one or more instances;

calculating, at the processor, a score for the neoplasia or tumor sample based on the ratio of the deletion count variable to the sample size count variable; and classifying the neoplasia or tumor sample as MSI when the score is greater than a threshold value;

A method of identifying and selecting a subject with a cancer or tumor with high microsatellite instability (MSI-H) comprising detecting a limited plurality of not more than 40, 30, 20 or 10 microsatellite indels associated with the MSI-H cancer or tumor, but not a low microsatellite instability (MSI-L) cancer or tumor, in a nucleic acid sample from the subject's cancer or tumor, wherein the limited plurality of not more than 40, 30, 20 or 10 microsatellite indels that are highly mutated in MSI-H cancers, but have a low indel rate in an MSI-L or microsatellite stable (MSS) cancer or tumor, are identified by or are selected by MSMuTect, and wherein the subject has an MSI-H cancer or tumor if at least 39, 35, 30 or 20 of the limited plurality of MS indels is present in the nucleic acid sample from the subject's cancer or tumor; and A method comprising:

identifying, at a processor of a computing device configured to analyze high throughput sequencing data, a plurality of microsatellite (MS) loci within a whole genome sequence (WGS) dataset from a neoplasia or a tumor;

identifying, at the processor, one or more aberrant sequence reads within the plurality of MS loci that contain deleted base pairs or inserted base pairs relative to a plurality of reference sequences corresponding to the one or more aberrant sequence reads;

aggregating the identified one or more aberrant sequence reads for each the MS loci into groups that contain the same number of deleted base pairs or inserted base pairs for each of the plurality of MS loci;

calculating a score for the neoplasia or tumor sample based on the ratio of deleted base pairs to inserted base pairs; and classifying the neoplasia or tumor sample as MSI when the score is greater than a threshold value.

5. The method of claim 4, further comprising administering one or more selected treatments to the subject having or at risk of having MSI.

6. The method of claim 4, wherein calculating step (g) or (f) is based on the following algorithm:

$$S = \log_{10}\left(\left|\frac{a_i \cdot N_i^{del\_j}}{N_i^{ref}}\right|\right);$$

wherein S is the score, i is the MS length, del_j is the size of the deletion, and N_i the number of MS loci of the predetermined length, optionally wherein $\alpha\_i=1$ for $8 \leq i \leq 13$ and $\alpha\_i=0$ otherwise.

7. The method of claim 4, wherein calculating step (g) or (f) is based on the following algorithm:

$$S = \log_{10}\left(\left|\frac{a_i \cdot N_i^{del\_j}}{N_i^{ref}}\right|\right);$$

wherein S is the score, i is the MS length, del_j is the size of the deletion, and N_i the number of MS loci of the predetermined length.

8. The method of claim 4, wherein the cancer or tumor is colon adenocarcinoma (COAD), stomach adenocarcinoma (STAD), or uterine corpus endometrial carcinoma (UCEC).

9. The method of claim 4, wherein the cancer or tumor is other than colon adenocarcinoma (COAD), stomach adenocarcinoma (STAD), or uterine corpus endometrial carcinoma (UCEC), optionally wherein:

the cancer or tumor is colon adenocarcinoma (COAD) and the limited plurality of microsatellite indels detected comprises at least 5, at least 10 or at least 20 MS indels from the list of 20 COAD MS indels in Table A or Table B, optionally wherein the limited plurality of microsatellite indels detected comprises at least 5, at least 10 or at least 20 MS indels from the list of 20 such MS indels for cancers other than COAD, STAD, or UCEC in Table A or Table B;

the cancer or tumor is stomach adenocarcinoma (STAD) and the limited plurality of microsatellite indels detected comprises at least 5, at least 10 or at least 20 MS indels from the list of 20 STAD MS indels in Table A or Table B;

the cancer or tumor is uterine corpus endometrial carcinoma (UCEC) and the limited plurality of microsatellite indels detected comprises at least 5, at least 10 or at least MS indels from the list of 20 UCEC MS indels in Table A or Table B.

10. The method of claim 4, wherein the method includes identifying one or more somatic indels in a microsatellite (MS) locus (MS indels) in one or more genes that are identified by or are selected by MSMutSig, optionally wherein:

the one or more MS indels are in one or more of the ACVR2A, RNF43, DOCK3, MSH3, ESRP1, PRDM2 and/or JAK1 genes, optionally wherein the cancer or tumor is COAD, STAD or UCEC, and the MS indel is selected from the MS indels listed in Table C, Table A or Table B of significantly mutated MS loci for COAD, STAD and UCEC cancers or tumors; and/or the one or more MS indels are in one or more of the ESRP1, PRDM2, or DOCK3 JAK1 genes.

11. The method of claim 4, further comprising administering an immunotherapy to the subject having an MSI-H cancer or tumor, optionally wherein the immunotherapy is administrating of a programmed cell death protein 1 (PD-1) inhibitor, optionally wherein the PD-1 inhibitor is an antibody, optionally wherein the antibody is pembrolizumab.

12. The method of claim 4, wherein the indel is a deletion.

13. The method of claim 4, wherein the indel is an insertion.

14. A composition selected from the group consisting of:

An apparatus comprising:
one or more network interfaces to communicate in a computer network;
a processor coupled to the network interfaces and adapted to execute one or more processes; and
a memory configured to store a process executable by the processor, the process when executed operable to:
identify a plurality of microsatellite (MS) loci within a whole genome sequence (WGS) dataset from a neoplasia or a tumor;
identify one or more aberrant MS loci within the plurality of MS loci that contain two or more deleted base pairs relative to one or more reference sequences corresponding to the one or more aberrant MS loci;
increment a sample size count variable for each of the identified one or more aberrant MS loci;
identify one or more instances where the one or more aberrant MS loci contain two or more deleted base pairs that are identical;
increment a deletion count variable for each of the identified one or more instances;
calculate a score for the neoplasia or tumor sample based on the ratio of the deletion count variable to the sample size count variable; and
classify the neoplasia or tumor sample as MSI when the score is greater than a threshold value;

An apparatus comprising:
one or more network interfaces to communicate in a computer network;
a processor coupled to the network interfaces and adapted to execute one or more processes; and
a memory configured to store a process executable by the processor, the process when executed operable to:
identify a plurality of microsatellite (MS) loci within a whole genome sequence (WGS) dataset from a neoplasia or a tumor;
identify one or more aberrant sequence reads within the plurality of MS loci that contain deleted base pairs or inserted base pairs relative to a plurality of reference sequences corresponding to the one or more aberrant sequence reads;
aggregate the identified one or more aberrant sequence reads for each the MS loci into groups that contain the same number of deleted base pairs or inserted base pairs for each of the plurality of MS loci;
calculate a score for the neoplasia or tumor sample based on the ratio of deleted base pairs to inserted base pairs; and
classify the neoplasia or tumor sample as MSI when the score is greater than a threshold value; and A kit for identifying a neoplasia or tumor sample as MSI or MSS, wherein the kit comprises reagents for effecting the following steps:
(a) procuring a neoplasia or tumor sample from a subject having or at risk of having MSI cancer;
(b) obtaining whole genome sequence (WGS) data from the neoplasia or tumor sample; and
(c) identifying a plurality of microsatellite (MS) loci within the WGS data.

* * * * *